US007897778B2

(12) United States Patent
Gibson et al.

(10) Patent No.: US 7,897,778 B2
(45) Date of Patent: Mar. 1, 2011

(54) BENZAMIDE COMPOUNDS

(75) Inventors: Keith Hopkinson Gibson, Macclesfield (GB); Elaine Sophie Elizabeth Stokes, Macclesfield (GB); Michael James Waring, Macclesfield (GB); David Michael Andrews, Macclesfield (GB); Zbigniew Stanley Matusiak, Macclesfield (GB); Mark Andrew Graham, Macclesfield (GB)

(73) Assignee: AstraZeneca, Sodertalje (SE)

( * ) Notice: Subject to any disclaimer, the term of this patent is extended or adjusted under 35 U.S.C. 154(b) by 667 days.

(21) Appl. No.: 11/661,498

(22) PCT Filed: Aug. 31, 2005

(86) PCT No.: PCT/GB2005/003355

§ 371 (c)(1),
(2), (4) Date: Mar. 3, 2008

(87) PCT Pub. No.: WO2006/024841

PCT Pub. Date: Mar. 9, 2006

(65) Prior Publication Data

US 2008/0293687 A1 Nov. 27, 2008

(30) Foreign Application Priority Data

Sep. 3, 2004 (GB) .................................. 0419565.7
Feb. 8, 2005 (GB) .................................. 0502545.7
Mar. 29, 2005 (GB) .................................. 0506165.0

(51) Int. Cl.
C07D 401/00 (2006.01)
C07D 211/78 (2006.01)
(52) U.S. Cl. .................................. 546/286; 546/268.1
(58) Field of Classification Search .................. 546/286, 546/268.1
See application file for complete search history.

(56) References Cited

U.S. PATENT DOCUMENTS 4,482,437 A    11/1984   Toomey, Jr.
5,256,668 A    10/1993   Hsu et al.

FOREIGN PATENT DOCUMENTS

| WO | WO 03/024448 | 3/2003 |
| WO | WO 03024448 | 3/2003 |
| WO | WO 03/048164 | 6/2003 |
| WO | WO 03048164 | 6/2003 |
| WO | WO 03/087057 | 10/2003 |
| WO | WO 03/087057 A1 * | 10/2003 |
| WO | WO 03087057 * | 10/2003 |
| WO | WO 03/092686 | 11/2003 |
| WO | WO 2005/032493 | 4/2005 |
| WO | WO 2005032493 | 4/2005 |

OTHER PUBLICATIONS

David M. Andrews. Oral Small Molecule Anti-Cancer Lead Optimization: Lessons in Campaign Design, Synthesis and Testing, 236th ACS National Meeting, Philadelphia, PA, Aug. 17-21, 2008, (Lecture given on Aug. 21).
Andrews D.M. et al, "Design and Campaign Synthesis of Piperidine- and Thiazole-Based Histone Deacetylase Inhibitors", Bioorganic and Medicinal Chemistry Letters, 2008, 18, 2580-2584.
Andrews D.M. et al, "Design and Campaign Synthesis of Pyridine-Based Histone Deacetylase Inhibitors", Bioorganic and Medicinal Chemistry Letters, 2008, 18, 2525-2529.
Final rejection from US PTO for U.S. Appl. No. 10/509,941 (corresponds to WO 03/087057 A).
Beato, M. J. et al. "Chromatin structure and the regulation of gene expression: remodeling at the MMTV promoter" J. Med. Chem., 74(12), pp. 711-724 (1996).
Finnin, M. S. et al. "Structures of a histone deacetylase homologue bound to the TSA and SAHA inhibitors" Nature, 401(6749), pp. 188-193 (1999).
Gabbianelli, M. "Hemoglobin switching in unicellular erythroid culture of sibling erythroid burst-forming units: kit ligand induces a dose-dependent fetal hemoglobin reactivation potentiated by sodium butyrate" Blood, 95(11), pp. 3555-3561 (2000).
Li, S. et al. "Transcriptional repression of the cystic fibrosis transmembrane conductance regulator gene, mediated by CCAAT displacement protein/cut homolog, is associated with histone deacetylation." J. Bio. Chem., 274(12), pp. 7803-7815 (1999).
Marks, P. et al. "Histone deacetylases and cancer: causes and therapies" Nat. Rev. Cancer, 1(3), pp. 194-202 (2001).
Meinke, P. T. et al. "Histone deacetylase: a target for antiproliferative and antiprotozoal agents" Curr. Med. Chem., 8(2), pp. 211-235 (2001).
Miller, T. A. et al. "Histone deacetylase inhibitors" J. Med. Chem., 46(24), pp. 5097-5116 (2003).
Steffan, J. S. et al. "Histone deacetylase inhibitors arrest polyglutamine-dependent neurodegeneration in *Drosophila* " Nature, 413(6857), pp. 739-743 (2001).
Taylor, E. C. et al. "Synthesis and biological activity of L-5-deazafolic acid and L-5-deazaaminopterin: synthetic strategies to 5-deazapteridines" J. Org. Chem., 48(25), pp. 4852-4860 (1983).
Ukhov, S. V. et al. "Naphthyridines. 14. 2-methylquinoline-3-carboxanilides and the synthesis therefrom of 2-substituted 1-oxo-3-phenyl-1,2,3,4-tetrahydrobenzo[b-1,6]-naphthridines" Chemistry of Heterocyclic Compounds, 25(2), pp. 196-197 (1989).

(Continued)

*Primary Examiner*—Nizal S Chandrakumar

(57) ABSTRACT

The invention concerns benzamide compounds of Formula (I), wherein $R^{1a}$, $R^{1b}$, $R^{1c}$, $R^2$, $R^3$, $R^4$, m and n have any of the meanings defined in the description; processes for their preparation, pharmaceutical compositions containing them and their use in the manufacture of a medicament for use as an antiproliferative agent in the prevention or treatment of tumours or other proliferative conditions which are sensitive to the inhibition of histone deacetylase (HDAC).

14 Claims, No Drawings

OTHER PUBLICATIONS

Wolffe, A. P. et al. "Transcriptional control. Sinful repression" Nature, 387(6628), pp. 16-17, (1997).

Yoshida, M. et al. "Reversible arrest of proliferation of rat 3Y1 fibroblasts in both the G1 and G2 phases by trichostatin A" Exper. Cell Res., 177(1), pp. 122-131 (1988).

* cited by examiner

BENZAMIDE COMPOUNDS

This invention concerns certain novel benzamide compounds, or pharmaceutically acceptable salts or pro-drug forms thereof, which are potent inhibitors of the enzyme histone deacetylase (HDAC). The invention also concerns processes for the manufacture of these novel benzamide compounds, to pharmaceutical compositions containing them and to their use in therapeutic methods, for example in the manufacture of medicaments to inhibit HDAC in a warm-blooded animal, such as man.

HDAC activity has been associated with a number of disease states, such as cancer (Marks et al., *Nature Reviews*, 1, 194-202, (2001)), cystic fibrosis (Li, S. et al, *J. Biol. Chem.*, 274, 7803-7815, (1999)), Huntingdons chorea (Steffan, J. S. et al., *Nature*, 413, 739-743, (2001)) and sickle cell anaemia (Gabbianelli, M. et al., *Blood*, 95, 3555-3561, (2000)). Accordingly, the invention also extends to methods of treating any of the aforementioned diseases using the benzamide compounds of the present invention, as well as to the use of these benzamide compounds in the manufacture of a medicament for the treatment of such disease states.

In the eukaryotic cell, DNA is routinely compacted to prevent transcription factor accessibility. When the cell is activated this compacted DNA is made available to DNA-binding proteins, thereby allowing the induction of gene transcription (Beato, M., *J. Med. Chem.*, 74, 711-724 (1996); Wolffe, A. P., *Nature*, 387, 16-17 (1997)). Nuclear DNA is known to associate with proteins known as histones to form a complex that is known as chromatin. The core histones, termed H2A, H2B, H3 and H4, are surrounded by 146 base pairs of DNA to form the fundamental unit of chromatin, which is known as the nucleosome. The N-terminal tails of the core histones contain lysine residues that are sites for post-transcriptional acetylation. Acetylation of the terminal amino group on the lysine side chain neutralizes the potential of the side chain to form a positive charge, and is thought to impact on chromatin structure.

Histone Deacetylases (HDACs) are zinc-containing enzymes which catalyse the removal of acetyl groups from the ε-amino termini of lysine residues clustered near the amino terminus of nucleosomal histones. HDACs may be divided into two classes, the first (HDAC 1, 2, 3 and 8) represented by yeast Rpd3-like proteins, and the second (HDAC 4, 5, 6, 7, 9 and 10) represented by yeast Hda1-like proteins. The reversible process of acetylation is known to be important in transcriptional regulation and cell-cycle progression. In addition, HDAC deregulation has been associated with several cancers and HDAC inhibitors, such as Trichostatin A (a natural product isolated from *Streptomyces hygroscopicus*), have been shown to exhibit significant cell growth inhibition and anti-tumour effects (Meinke, P. T., *Current Medicinal Chemistry*, 8, 211-235 (2001)). Yoshida et al, (*Exper. Cell Res.*, 177, 122-131 (1988)) teach that Trichostatin A causes the arrest of rat fibroblasts at the G1 and G2 phases of the cell cycle, thereby implicating the role of HDAC in the regulation of the cell cycle. Furthermore, Trichostatin A has been shown to induce terminal differentiation, inhibit cell growth, and prevent the formation of tumours in mice (Finnin et al., *Nature*, 401, 188-193 (1999)).

It is known from International Patent Publication Numbers WO 03/087057 and WO 03/092686, that certain benzamide derivatives are inhibitors of HDAC. One particular compound disclosed in WO 03/087057 is N-(2-aminophenyl)-4-pyridin-2-yl-benzamide.

However, there is no specific disclosure in either of these documents of benzamide derivatives, which possess a further substituted-pyridin-2-yl ring moiety at the 4-position of the benzamide ring. We have now found that certain benzamide derivatives possessing an optionally substituted 3-cyanopyridin-2-yl group in the 4-position of the benzamide ring are potent inhibitors of the HDAC enzyme.

According to the present invention there is provided a compound of formula (I):

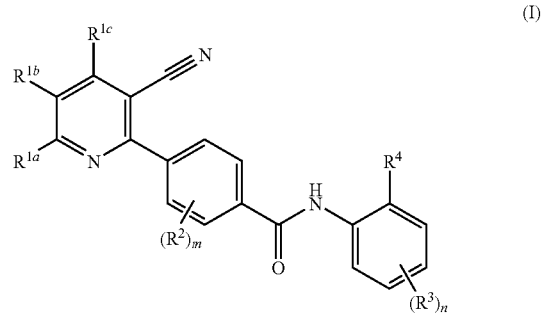

(I)

wherein:

$R^{1a}$ is selected from hydrogen, amino, nitro, (1-3C)alkyl, N-(1-3C)alkylamino, N,N-di-(1-3C)alkylamino, phenyl, or piperazinyl;

and wherein:

(i) if $R^{1a}$ is N-(1-3C)alkylamino or N,N-di-(1-3C)alkylamino group, the (1-3C)alkyl moiety is optionally substituted by hydroxy or (1-3C)alkoxy;

(ii) if $R^{1a}$ is phenyl, it is optionally substituted by halo, amino, N-(1-3)alkylamino, or N,N-di-(1-3C)alkylamino; and (iii) if $R^{1a}$ is piperazinyl, it is optionally substituted by halo, amino, (1-3C)alkyl, N-(1-3)alkylamino, or N,N-di-(1-3C)alkylamino;

$R^{1b}$ is selected from:

(i) hydrogen, halo, nitro, cyano, hydroxy, trifluoromethyl, trifluoromethoxy, amino, carboxy, carbamoyl, mercapto, sulphamoyl, (1-6C)alkyl, hydroxy(1-6C)alkyl, (2-6C)alkenyl, (2-6C)alkynyl, (3-6C)cycloalkyl, (3-6C)cycloalkyl(1-6C)alkyl, (3-6C)cycloalkenyl, (3-6C)cycloalkenyl(1-6C)alkyl, (1-6C)alkoxy, (1-6C)alkanoyloxy, N-(1-6C)alkylamino, N,N-di-[(1-6C)alkyl]amino, N-[(3-6C)cycloalkyl]amino, N,N-di-[(3-6C)cycloalkyl]amino, N-[(3-6C)cycloalkyl(1-6C)alkyl]amino, N,N-di-[(3-6C)cycloalkyl(1-6C)alkyl]amino, N-[(3-6C)cycloalkyl]-N-[(1-6C)alkyl]amino, N-[(3-6C)cycloalkyl(1-6C)alkyl]-N-[(1-6C)alkyl]amino, N-(1-6C)alkanoylamino, N,N-di-[(1-6C)alkanoyl]amino, N-[(1-6C)alkoxy(1-6C)alkyl]amino, N,N-di-[(1-6C)alkoxy(1-6C)alkyl]amino, N-[(1-6C)alkoxy(1-6C)alkyl]-N-[(1-6C)alkyl]amino, N-(1-6C)alkylcarbamoyl, N,N-di-[(1-6C)alkyl]carbamoyl, (1-6C)alkylthio, (1-6C)alkylsulphinyl, (1-6C)alkylsulphonyl, (1-6C)alkoxycarbonyl, N-(1-6C)alkylsulphamoyl, N,N-di-[(1-6C)alkyl]sulphamoyl, aryl, aryl-(1-6C)alkyl, a carbon linked heterocyclyl group, or a heterocyclyl-(1-6C)alkyl group wherein the heterocyclyl moiety is carbon-linked to the alkyl group; or (ii) a group of sub-formula II:

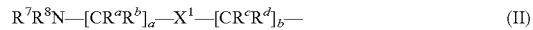

$R^7R^8N-[CR^aR^b]_a-X^1-[CR^cR^d]_b-$ (II)

wherein:

$X^1$ is selected from a direct bond, —O— or —C(O)—;

integer a is 0, 1, 2, 3 or 4, with the proviso that if $X^1$ is —O—, integer a is at least 1;

integer b is 0, 1, 2, 3 or 4;

each $R^a$, $R^b$, $R^c$ and $R^d$ group present is independently selected from hydrogen, halo, hydroxy or (1-4C)alkyl;

$R^7$ and $R^8$ are independently selected from hydrogen, (1-6C)alkyl, hydroxy(1-6C)alkyl, halo(1-6C)alkyl, (2-6C)alkenyl, (3-6C)cycloalkyl, (3-6C)cycloalkyl(1-6C)alkyl, (1-6C)alkoxy(1-6C)alkyl, (1-6C)alkanoyl, (3-6C)cycloalkenyl, (3-6C)cycloalkenyl(1-6C)alkyl, aryl, aryl(1-6C)alkyl, heterocyclyl;

a heterocyclyl-(1-6C)alkyl group wherein the heterocyclyl moiety is carbon-linked to the alkyl group and is either selected from a substituted or unsubstituted thienyl, pyrimidinyl, pyridazinyl, furanyl, tetrahydrofuranyl, pyranyl, tetrahydropyranyl, pyridinyl, pyrazinyl, thiazolyl, or indolyl group, or from one the following particular substituent groups: 1,3-dimethyl-1H-pyrazol-5-yl, 3,5-dimethyl-1H-pyrazol-4-yl, and 1-methyl-1H-imidazol-4-yl;

a group of sub-formula III:

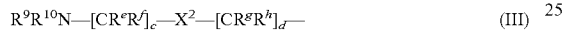   (III)

wherein:

$X^2$ is selected from a direct bond, —O— or —C(O)—;

integer c is 1, 2 or 3;

integer d is 0, 1, 2 or 3;

each $R^e$, $R^f$, $R^g$ and $R^h$ group present is independently selected from hydrogen, halo, hydroxy or (1-4C)alkyl;

$R^9$ and $R^{10}$ are independently selected from hydrogen, (1-6C)alkyl, hydroxy(1-6C)alkyl, halo(1-6C)alkyl, (3-6C)cycloalkyl, (3-6C)cycloalkyl(1-6C)alkyl, (1-6C)alkoxy(1-6C)alkyl, or $R^9$ and $R^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by hydroxy, halo, (1-4C)alkyl, carbamoyl, or —[CH$_2$]$_e$—NR$^{11}$R$^{12}$ (wherein integer e is 0, 1 or 2, and $R^{11}$ and $R^{12}$ are independently selected from hydrogen, (1-6C)alkyl, (3-6C)cycloalkyl or (3-6C)cycloalkyl(1-6C)alkyl);

or $R^7$ and $R^8$ are linked so that, together with the nitrogen atom to which they are attached, they form a 4 to 10-membered heterocyclic ring, said heterocyclic ring optionally comprising, in addition to the nitrogen atom to which $R^7$ and $R^8$ are attached, one or two further nitrogen atoms; or (iii) a group of the sub-formula IV:

   (IV)

wherein:

$Y^1$ is a direct bond or —[CR$^{13}$R$^{14}$]$_x$— where integer x is 1 to 4 and $R^{13}$ and $R^{14}$ are independently selected from hydrogen, halo and (1-4C)alkyl;

$X^3$ is selected from —O—, —S—, —SO—, —SO$_2$—, —C(O)—, —OC(O)— and —C(O)O—, with the proviso that $Y^1$ is not a direct bond if $X^3$ is —C(O)—;

$Q^1$ is selected from (1-6C)alkyl, (3-6C)cycloalkyl, (3-6C)cycloalkyl(1-6C)alkyl, (3-6C)cycloalkenyl, (3-6C)cycloalkenyl(1-6C)alkyl, aryl, aryl-(1-6C)alkyl, heterocyclyl, heterocyclyl-(1-6C)alkyl, or $R^{15}R^{16}$N-(1-6C)alkyl (wherein $R^{15}$ and $R^{16}$ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl);

and wherein any heterocyclyl ring within a $R^{1b}$ substituent group (apart from those for which particular substituents are expressly stated above, such as heterocyclyl rings formed when $R^9$ and $R^{10}$ are linked) is optionally substituted on carbon by one or more $Z^1$ substituent groups (for example 1, 2 or 3), which may be the same or different, selected from:

(a) halo, nitro, cyano, hydroxy, trifluoromethyl, trifluoromethoxy, amino, carboxy, carbamoyl, mercapto, sulphamoyl, (1-6C)alkyl, hydroxy(1-6C)alkyl, (2-6C)alkenyl, (2-6C)alkynyl, (1-6C)alkoxy, (1-6C)alkanoyl, (1-6C)alkanoyloxy, (1-6C)alkoxy-(1-6C)alkyl, (1-6C)alkoxycarbonyl, halo(1-6C)alkyl, N-[(1-6C)alkyl]amino, N,N-di-[(1-6C)alkyl]amino, N-(1-6C)alkylcarbamoyl, N,N-di-[(1-6C)alkyl]carbamoyl, (1-6C)alkylthio, (1-6C)alkylsulphinyl, (1-6C)alkylsulphonyl, N-(1-6C)alkylsulphamoyl, N,N-di-[(1-6C)alkyl]sulphamoyl, aryl, aryl-(1-6C)alkyl, heterocyclyl, heterocyclyl-(1-6C)alkyl, (b) a group of the sub-formula V:

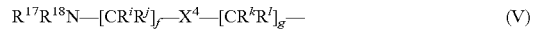   (V)

wherein $X^4$ is selected from a direct bond, —O— or —C(O)—;

integer f is 0, 1, 2 or 3, with the proviso that integer f is at least 1 if $X^4$ is —O—;

integer g is 0, 1 or 2;

each $R^i$, $R^j$, $R^k$ and $R^l$ group present is independently selected from hydrogen, halo, hydroxy or (1-4C)alkyl;

$R^{17}$ and $R^{18}$ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl; or (c) a group of the sub-formula VI:

   (VI)

wherein:

$Y^2$ is a direct bond or —[CR$^{19}$R$^{20}$]$_y$— wherein integer y is 1 to 4 and $R^{19}$ and $R^{20}$ are independently selected from hydrogen, halo and (1-4C)alkyl;

$X^5$ is selected from —O—, —S—, —SO—, —SO$_2$—, —C(O)—, —OC(O)— or —C(O)O—; and $Q^2$ is selected from (1-6C)alkyl, (3-6C)cycloalkyl, (3-6C)cycloalkyl(1-6C)alkyl, (3-6C)cycloalkenyl, (3-6C)cycloalkenyl(1-6C)alkyl, aryl, aryl-(1-6C)alkyl, heterocyclyl, heterocyclyl-(1-6C)alkyl, $R^{21}R^{22}$N-(1-6C)alkyl (wherein $R^{21}$ and $R^{22}$ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl);

and wherein if any heterocyclyl group within a $R^{1b}$ substituent group contains an unsubstituted nitrogen atom, then, unless any particular substituents are expressly stated in the definition above (e.g. such as when $R^9$ and $R^{10}$ are linked to form a heterocyclic ring together with the nitrogen atom to which they are attached), the nitrogen atom may be optionally substituted by one or more $Z^2$ substituent groups (for example 1, 2 or 3), which may be the same or different, selected from:

(a) trifluoromethyl, carboxy, carbamoyl, (1-6C)alkyl, hydroxy(1-6C)alkyl, (2-6C)alkenyl, (1-6C)alkanoyl, (1-6C)alkoxy-(1-6C)alkyl, (1-6C)alkoxycarbonyl, halo (1-6C)alkyl, N-(1-6C)alkylamino-(1-6C)alkyl, N,N-di-[(1-6C)alkyl]amino-(1-6C)alkyl, (1-6C)alkylsulphonyl, aryl, aryl-(1-6C)alkyl, heterocyclyl, heterocyclyl-(1-6C)alkyl; or (b) a group of the formula VII:

wherein
integer h is 0, 1, 2, or 3;
each $R'''$ and $R''$ group present is independently selected from hydrogen, halo, hydroxy or (1-4C)alkyl;
$R^{23}$ and $R^{24}$ are each independently selected from hydrogen, (1-6C)alkyl, (1-6C)alkoxy, (1-6C)alkoxy (1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl; or (c) a group of the formula VIII:

wherein $Y^3$ is a direct bond or $-[CR^{25}R^{26}]_z-$ wherein z is 1 to 4 and $R^{25}$ and $R^{26}$ are independently selected from hydrogen, halo and (1-4C)alkyl;
$X^6$ is selected from $-O-$, $-S-$, $-SO-$, $-SO_2-$, $-C(O)-$, $-OC(O)-$ or $-C(O)O-$ if $Y^3$ is $-[CR^{23}R^{24}]_z-$, and if $Y^3$ is a direct bond, $X^6$ is selected from $-S-$, $-SO-$, $-SO_2-$, $-C(O)-$, and $-OC(O)-$; and
$Q^3$ is selected from (1-6C)alkyl, (3-6C)cycloalkyl, (3-6C)cycloalkyl(1-6C)alkyl, aryl, aryl-(1-6C)alkyl, heterocyclyl, heterocyclyl-(1-6C)alkyl or $R^{27}R^{28}N-$(1-6C)alkyl (wherein $R^{27}$ and $R^{28}$ are each independently selected from hydrogen, (1-6C)alkyl, (1-6C) alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C) alkyl);

and wherein any heterocyclyl group within a $Z^1$ or $Z^2$ substituent group optionally bears one or more substituent groups (for example 1, 2 or 3), which may be the same or different, selected from halo, cyano, trifluoromethyl, amino, carboxy, carbamoyl, mercapto, sulphamoyl, (1-6C)alkyl, hydroxy(1-6C)alkyl, halo(1-6C)alkyl, (2-6C)alkenyl, (2-6C)alkynyl, (1-6C)alkoxy, (1-6C)alkanoyl, (1-6C)alkanoyloxy, N-[(1-6C)alkyl]amino, and N,N-di-[(1-6C)alkyl]amino;

and wherein any non-aromatic heterocyclyl group within a $R^{1b}$ substituent (including optional substituent groups $Z^1$ and $Z^2$) optionally bears 1 or 2 oxo substituents;

and wherein any alkyl, alkenyl, alkynyl, alkoxy, alkanoyl, alkanoyloxy, cycloalkyl, or cycloalkenyl group within a $R^{1b}$ substituent group (including optional substituent groups $Z^1$ and $Z^2$) is, unless particular substituents are expressly stated above, optionally substituted by one or more $Z^3$ substituent groups (for example 1, 2 or 3), which may be the same or different, selected from halo, cyano, mercapto, (1-6C)alkoxy, trifluoromethyl, or $-NR^{29}R^{30}$ wherein each of $R^{29}$ and $R^{30}$ is independently selected from hydrogen, (1-6C)alkyl, (1-6C) alkoxy, (3-6C)cycloalkyl, (3-6C)cycloalkyl(1-6C)alkyl;

and wherein any aryl group within a $R^{1b}$ substituent group (including optional substituent groups $Z^1$ and $Z^2$) is optionally substituted by one or more $Z^4$ substituent groups (for example 1, 2 or 3), which may be the same or different, selected from halo, nitro, cyano, hydroxy, amino, (1-6C) alkyl, hydroxy(1-6C)alkyl, halo(1-6C)alkyl, (1-6C)alkoxy, (1-6C)alkanoyl, N-[(1-6C)alkyl]amino, N,N-di-[(1-6C) alkyl]amino, carbamoyl, N-(1-6C)alkylcarbamoyl, N,N-di-[(1-6C)alkyl]carbamoyl;

$R^{1c}$ is selected from hydrogen, halo, nitro, cyano, hydroxy, trifluoromethyl, trifluoromethoxy, amino, carboxy, carbamoyl, mercapto, sulphamoyl, (1-3C)alkyl, (2-3C)alkenyl, (2-3C)alkynyl, (1-3C)alkoxy, (1-3C)alkanoyl, (1-3C)alkanoyloxy, N-(1-3C)alkylamino, N,N-di-[(1-3C)alkyl] amino, (1-3C)alkanoylamino, N-(1-3C)alkylcarbamoyl, N,N-di-(1-3C)alkylcarbamoyl, (1-3C) alkylthio, (1-3C) alkylsulphinyl, (1-3C)alkylsulphonyl, (1-3C)alkoxycarbonyl, N-(1-3C)alkylsulphamoyl, and N,N-di-(1-3C)alkylsulphamoyl;

with the proviso that at least one of $R^{1a}$, $R^{1b}$ and $R^{1c}$ is hydrogen;
m is 0, 1, 2, 3 or 4;
$R^2$ is halo;
n is 0, 1, 2, 3 or 4;
$R^3$ is selected from halo, nitro, cyano, hydroxy, trifluoromethyl, trifluoromethoxy, amino, carboxy, carbamoyl, mercapto, sulphamoyl, (1-3C)alkyl, (2-3C)alkenyl, (2-3C)alkynyl, (1-3C)alkoxy, (1-3C)alkanoyl, (1-3C)alkanoyloxy, N-(1-3C)alkylamino, N,N-di-[(1-3C)alkyl]amino, (1-3C)alkanoylamino, N-(1-3C)alkylcarbamoyl, N,N-Di(1-3C)alkylcarbamoyl, (1-3C) alkylthio, (1-3C)alkylsulphinyl, (1-3C) alkylsulphonyl, (1-3C)alkoxycarbonyl, N-(1-3C) alkylsulphamoyl, and N,N-di-(1-3C)alkylsulphamoyl; and
$R^4$ is amino or hydroxy;

or a pharmaceutically acceptable salt thereof.

It is to be understood that, insofar as certain of the compounds of Fulmula (I) defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula (I) defined above may exhibit the phenomenon of tautomerism. In particular, tautomerism may affect any heterocyclic groups that bear 1 or 2 oxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples.

Where optional substituents are selected from "one or more" substituent groups it is to be understood that this definition includes all substituents being chosen from one of the specified groups or the substituents being chosen from two or more of the specified groups.

Furthermore, where reference is made to a specified group within a $R^{1b}$ substituent group being optionally substituted by one or more specified substituent groups, then such a reference is to be understood as referring to the possibility of the specified group being optionally substituted if it forms the $R^{1b}$ substituent group per se or if it is present as a moiety within a $R^{1b}$ substituent group. For instance, the reference to any alkyl group within a $R^{1b}$ substituent group (including optional substituent groups $Z^1$ and $Z^2$) being optionally substituted by one or more $Z^3$ substituent groups is to be understood as including, for example, $R^{1b}$ being an alkyl group per se which is optionally substituted by one or more of the specified $Z^3$ substituent groups, as well as the possibility of an alkyl moiety of a group such as a N,N-di-[(1-6C)alkyl]amino optionally bearing one or more $Z^3$ substituent groups.

In this specification the generic term "(1-6C)alkyl" includes both straight-chain and branched-chain alkyl groups such as propyl, isopropyl and tert-butyl, and also (3-6C)cycloalkyl groups such as cyclopropyl, cyclobutyl, cyclopentyl, and cyclohexyl, and also cycloalkyl-alkyl groups having 4 to 6 carbon atoms, such as cyclopropylmethyl, 2-cyclopropylethyl, cyclobutylmethyl, 2-cyclobutylethyl, and cyclopentylmethyl. However, references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and cycloalkyl-alkoxy groups having 4 to 6 carbon atoms, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and N-(cycloalkylalkyl)amino groups having 4 to 6 carbon atoms, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and N,N-di-[(1-6Calkyl]amino includes N,N-di-[(3-6C)cycloalkyl]amino groups and N,N-di-[cycloalkylalkyl]amino groups in which the cycloalkylalkyl moiety has 4 to 6 carbon atoms, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

A person skilled in the art will appreciate that the terms "(1-4C)alkyl", "(1-3C)alkyl" and "(1-2C)alkyl" are used herein refer to any of the alkyl groups defined above that posses 1 to 4, 1 to 3 and 1 to 2 carbon atoms respectively. The same convention applies to other terms used herein, such as, for example, "(1-4C)alkoxy", "(1-3C)alkoxy" and "(1-2C) alkoxy".

The term "halo" refers to fluoro, chloro, bromo and iodo.

The term "heterocyclyl" refers to a saturated, partially saturated or unsaturated, mono or bicyclic ring containing 3-12 atoms of which at least one atom is chosen from nitrogen, sulphur or oxygen, and which may, unless otherwise specified, be carbon or nitrogen linked, and wherein a $CH_2$ group can optionally be replaced by a C(O), and wherein a ring sulphur atom may be optionally oxidised to form the S-oxide(s). Preferably a "heterocyclyl" is a saturated, partially saturated or unsaturated, monocyclic ring containing 4, 5 or 6 atoms, or a saturated, partially saturated or unsaturated, bicyclic ring containing 6, 7, 8, 9, or 10 atoms, wherein at least one atom of the ring is chosen from nitrogen, sulphur or oxygen, and the ring system may, unless otherwise specified, be carbon or nitrogen linked, and wherein a ring sulphur atom may be optionally oxidised to form S-oxide(s). Examples and suitable values of the term "heterocyclyl" are azetidinyl, thiazolidinyl, pyrrolidinyl, 1,3-benzodioxolyl, 1,2,4-oxadiazolyl, morpholinyl, tetrahydrofuranyl, furanyl, tetrahydropyranyl, piperidinyl, piperazinyl, thiomorpholinyl, 1,3-dioxolanyl, homopiperazinyl, thienyl, pyrrolyl, pyrazolyl, oxadiazolyl, tetrazolyl, oxazolyl, thienopyrimidinyl, thienopyridinyl, thieno[3,2-d]pyrimidinyl, 1,3,5-triazinyl, purinyl, 1,2,3,4-tetrahydroquinolinyl, benzimidazolyl, benzthiazolyl, benzoxazolyl, benzothienyl, benzofuranyl, indazolyl, quinazolinyl, cinnolinyl, phthalazinyl, quinoxalinyl, napthyridinyl, benzotriazolyl, pyrrolothienyl, imidazothienyl, isoxazolyl, imidazolyl, thiadiazolyl, isothiazolyl, 1,2,3-triazolyl, 1,2,4-triazolyl, pyranyl, indolyl, pyrimidyl, thiazolyl, pyrazinyl, pyridazinyl, pyridinyl, quinolyl, quinazolinyl, 1-isoquinolinyl, 2-azabicyclo[2.2.1]heptyl, 3-azabicyclo[3.1.0]hexyl, 7-azabicyclo[2.2.1]heptyl, 2-azabicyclo[2.2.2]octyl, and hexahydropyrrolo[3,4-c]pyrrolyl.

Particular examples of 4-, 5- or 6-membered monocyclic heterocyclyl groups include azetidinyl, pyrrolidinyl, piperidinyl, piperazinyl, morpholinyl, tetrahydrofuranyl, furanyl, tetrahydropyranyl, pyranyl, pyrrolyl, pyridinyl, pyrazinyl, pyrimidinyl, thienyl, pyridazinyl, and thiazolyl. Particular examples of bicyclic heterocyclic ring systems containing 6, 7, 8, 9, or 10 atoms include 3-azabicyclo[3.1.0]hexyl, hexahydropyrrolo[3,4-c]pyrrolyl, 7-azabicyclo[2.2.1]heptyl, 2-azabicyclo[2.2.2]octyl, especially 3-azabicyclo[3.1.0]hex-3-yl, hexahydropyrrolo[3,4-c]pyrrol-2-yl, 7-azabicyclo[2.2.1]hept-7-yl, and 2-azabicyclo[2.2.2]oct-2-yl.

Where a heterocyclyl group includes one or more nitrogen atoms, these may carry a hydrogen atom or a substituent group such as a (1-6C)alkyl group if required to fulfil the bonding requirements of nitrogen, or they may be linked to the rest of the structure by way of the nitrogen atom. A nitrogen atom within a heterocyclyl group may be oxidized to give the corresponding N oxide.

An "aryl" group is, for example, phenyl, indenyl, indanyl, naphthyl, tetrahydronaphthyl or fluorenyl, preferably phenyl.

Within this specification composite terms are used to describe groups comprising more that one functionality such as aryl(1-6C)alkyl and heterocyclyl(1-6C)alkyl. These composite terms are to be given their ordinary meanings and will be understood by a person skilled in the art. For example, the terms aryl(1-6C)alkyl and heterocyclyl-(1-6C)alkyl refer to substituent groups wherein the aryl and heterocyclyl moieties respectively are linked via a (1-6C)alkyl chain. For instance, such terms encompass substituent groups where the aryl and heterocyclyl moieties are linked via a methylene or ethylene linker. Suitable examples of such groups include [aryl]methyl, [heterocyclyl]methyl, 1-[aryl]ethyl, 1-[heterocyclyl] ethyl, 2-[aryl]ethyl, and 2-[heterocyclyl]ethyl. The same convention also applies to other composite terms used herein, such as (1-6C)alkoxy(1-6C)alkyl and (3-6C)cycloalkyl(1-6C)alkyl.

A suitable value for a carbon-linked heterocyclyl-alkyl group (i.e. a heterocyclyl-alkyl group wherein the heterocyclyl moiety is carbon-linked to the alkyl group) include a carbon-linked azetidinylalkyl, pyrrolidinylalkyl, piperidinylalkyl, piperazinylalkyl, morpholinylalkyl, homopiperazinylalkyl, homopiperidinylalkyl, pyrrolylalkyl, oxazolylalkyl, thiazolylalkyl, imidazolylalkyl, isoxazolylalkyl, isothiazolylalkyl, oxadiazolylalkyl, triazolylalkyl, pyridinylalkyl, pyridazinylalkyl, pyrimidinylalkyl, pyrazolylalkyl, pyrazinylalkyl, oxindolylalkyl, tetrahydrofuranylalkyl, furanylalkyl, tetrahydropyranylalkyl, pyranylalkyl, and indolylalkyl groups.

Suitable values for any of the groups $R^{1a}$, $R^{1c}$, or $R^3$, or groups within a $R^{1a}$, $R^{1c}$, or $R^3$ substituent group, are as follows:

| | |
|---|---|
| for (1-3C)alkyl: | methyl, ethyl, propyl, and isopropyl; |
| for (2-3C)alkenyl: | vinyl, isopropenyl, and allyl; |
| for (2-3C)alkynyl: | ethynyl, and 2-propynyl; |
| for (1-3C)alkanoyl: | acetyl and propionyl; |
| for (1-3C)alkanoyloxy: | acetoxy and propionyloxy; |
| for (1-3C)alkoxy: | methoxy, ethoxy, and propoxy; |
| for N-(1-3C)alkylamino: | methylamino, ethylamino, propylamino, and isopropylamino; |
| for N,N-di-[(1-3C)alkyl]amino: | dimethylamino, diethylamino, N-ethyl-N-methylamino and diisopropylamino; |
| for (1-3C)alkanoylamino: | acetamido and propionamido; |
| for N-(1-3C)alkylcarbamoyl: | N-methylcarbamoyl, N-ethylcarbamoyl and N-propylcarbamoyl; |
| for N,N-di-(1-3C)alkylcarbamoyl: | N,N-dimethylcarbamoyl, N-ethyl-N-methylcarbamoyl and N,N-diethylcarbamoyl; |
| for (1-3C)alkylthio: | methylthio, ethylthio and propylthio; |
| for (1-3C)alkylsulphinyl: | methylsulphinyl and ethylsulphinyl; |
| for (1-3C)alkylsulphonyl: | methylsulphonyl and ethylsulphonyl; |
| for (1-3C)alkoxycarbonyl: | methoxycarbonyl, ethoxycarbonyl, and propoxycarbonyl; |
| for N-(1-3C)alkylsulphamoyl: | N-methylsulphamoyl and N-ethylsulphamoyl; and |
| for N,N-di-(1-3C)alkylsulphamoyl: | N,N-dimethylsulphamoyl. |

Suitable values for $R^{1b}$, or optional substituents within a $R^{1b}$ substituent group, are as follows:

| | |
|---|---|
| for halogeno | fluoro, chloro, bromo and iodo; |
| for (1-6C)alkyl: | methyl, ethyl, propyl, isopropyl, tert-butyl, cyclobutyl, cyclohexyl, cyclopropylmethyl, cyclobutylmethyl and 2-cyclopropylethyl; |
| for (1-4C)alkyl: | methyl, ethyl, propyl, isopropyl, tert-butyl, and cyclobutyl; |
| for (1-2C)alkyl: | methyl and ethyl; |
| for (2-6C)alkenyl: | vinyl, isopropenyl, allyl and but-2-enyl; |
| for (2-6C)alkynyl: | ethynyl, 2-propynyl and but-2-ynyl; |
| for (3-6C)cycloalkyl: | cyclopropyl, cyclobutyl, cyclopentyl, and cyclohexyl; |
| for (3-6C)cycloalkyl-(1-6C)alkyl: | cyclopropylmethyl, cyclobutylmethyl, cyclopentylmethyl, 2-cyclopropylethyl and 2-cyclobutylpropyl; |
| for (3-6C)cycloalkenyl: | cyclopropenyl and cyclobutenyl; |
| for (3-6C)cycloalkenyl(1-6C)alkyl: | cyclopropenylmethyl and cyclobutenylmethyl; |
| for (1-6C)alkoxy: | methoxy, ethoxy, propoxy, isopropoxy and butoxy; |
| for (1-6C)alkoxy(1-6C)alkyl: | methoxymethyl, 2-methoxyethyl, 1-methoxyethyl, and 3-methoxypropyl; |
| for (1-6C)alkanoyloxy: | acetoxy and propionyloxy; |
| for halo(1-6C)alkyl: | chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl, 3,3,3-trifluoropropyl, and trifluoromethyl; |
| for hydroxy-(1-6C)alkyl group: | hydroxymethyl, 2-hydroxyethyl, 1-hydroxyethyl and 3-hydroxypropyl; |
| for N-(1-6C)alkylamino: | methylamino, ethylamino, propylamino, isopropylamino and butylamino; |
| for N,N-di-[(1-6C)alkyl]amino: | dimethylamino, diethylamino, N-ethyl-N-methylamino and diisopropylamino; |
| for N-[(3-6C)cycloalkyl]amino: | cyclopropylamino, cyclobutylamino and cyclopentylamino; |
| for N,N-di-[(3-6C)cycloalkyl]amino: | di-cyclopropylamino; |
| for N-[(3-6C)cycloalkyl-(1-6C)alkyl]amino: | cyclopropylmethylamino and cyclobutylmethylamino; |
| for N,N-di-[(3-6C)cycloalkyl-(1-6C)alkyl]amino: | dicyclopropylmethylamino; |
| for N-[(3-6C)cycloalkyl]-N-[(1-6C)alkyl]amino: | N-cyclopropyl-N-methylamino and N-cyclopropyl-N-butylamino; |
| for N-[(3-6C)cycloalkyl-(1-6C)alkyl]-N-[(1-6C)alkyl]amino: | N-cyclopropylmethyl-N-methylamino and N-cyclobutylmethyl-N-methylamino; |
| for N-(1-6C)alkanoylamino: | acetamido and propionamido; |
| for N,N-di-[(1-6C)alkanoyl]amino: | diacetylamino; |
| for N-[(1-6C)alkoxy(1-6C)alkyl]amino: | methoxymethylamino and 2-methoxyethylamino; |
| for N,N-di-[(1-6C)alkoxy(1-6C)alkyl]amino: | di-methoxymethylamino and di-(2-methoxyethyl)amino; |
| for N-[(1-6C)alkoxy(1-6C)alkyl]-N-[(1-6C)alkyl]amino: | N-(2-methoxyethyl)-N-methylamino, N-(2-methoxyethyl)-N-ethylamino and N-(2-methoxyethyl)-N-isopropylamino; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |

| | |
|---|---|
| for a hydroxy-substituted (1-6C)alkyl group: | hydroxymethyl, 2-hydroxyethyl, 1-hydroxyethyl and 3-hydroxypropyl; |
| for a halo-substituted (1-6C)alkyl group: | chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl, 3,3,3-trifluoropropyl, and trifluoromethyl; |
| for a mercapto-substituted (1-6C)alkyl group: | mercaptomethyl, 2-mercaptoethyl, 1-mercaptoethyl and 3-mercaptopropyl; |
| for a (1-6C)alkoxy-substituted (1-6C)alkyl group: | methoxymethyl, ethoxymethyl, 1-methoxyethyl, 2-methoxyethyl, 2-ethoxyethyl and 3-methoxypropyl; |
| for a cyano-substituted (1-6C)alkyl group: | cyanomethyl, 2-cyanoethyl, 1-cyanoethyl and 3-cyanopropyl; |
| for an amino-substituted (1-6C)alkyl: | aminomethyl, 2-aminoethyl, 1-aminoethyl, 3-aminopropyl, 1-aminopropyl and 5-aminopropyl; |
| for aryl: | phenyl; |
| for aryl-(1-6C)alkyl: | benzyl and 2-phenylethyl, 2-phenylpropyl and 3-phenylpropyl; |
| for heterocyclyl-(1-6C)alkyl: | azetidinylmethyl, pyrrolidinylmethyl, piperidinylmethyl, piperazinylmethyl, morpholinylmethyl, 1-azetidinylethyl, 1-pyrrolidinylethyl, 1-piperidinylethyl, 1-piperazinylethyl, 1-morpholinylethyl. |

Particular examples of $R^{1b}$ when it is a group of the sub-formula II:

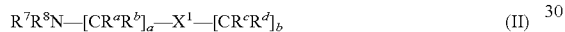

$$R^7R^8N-[CR^aR^b]_a-X^1-[CR^cR^d]_b \qquad (II)$$

include (methylamino)methyl, (ethylamino)methyl, 1-(ethylamino)ethyl, (propylamino)methyl, (isopropylamino)methyl, (cyclopropylamino)methyl, (butylamino)methyl, (cyclobutylamino)methyl, (cyclopentylamino)methyl, (1-methylpropylamino)methyl, (2-methylpropylamino)methyl, (allylamino)methyl, (di-ethylamino)methyl, [(ethyl)(methyl)amino]methyl, [(isopropyl)(methyl)amino]methyl, [(propyl)(methyl)amino]methyl, [(butyl)(methyl)amino]methyl, [(cyclopropylmethyl)amino]methyl, [(cyclobutylmethyl)(methyl)amino]methyl, [(2-methoxyethyl)(methyl)amino]methyl, [(isopropyl)(2-methoxyethyl)amino]methyl, [(2-methoxyethyl)amino]methyl, [(ethyl)(2-methoxyethyl)amino]methyl, [(2-methoxy-1-methylethyl)amino]methyl, [(3-methoxypropyl)amino]methyl, [(3-isopropoxypropyl)amino]methyl, [(2-ethoxyethyl)amino]methyl, [(2-isopropoxyethyl)amino]methyl, [(3-ethoxypropyl)amino]methyl, [(2-propoxyethyl)amino]methyl, [(2-methoxy-2-methylpropyl)amino]methyl, [bis(2-methoxyethyl)amino]methyl, [(2-hydroxyethyl)(ethyl)amino]methyl, [(2-hydroxyethyl)(methyl)amino]methyl, {[2-(di-methylamino)ethyl]amino}methyl, {[2-(di-ethylamino)ethyl]amino}methyl, {[2-(di-methylamino)ethyl][methyl]amino}methyl, {[2-(di-ethylamino)ethyl][methyl]amino}methyl, {[2-(di-methylamino)-1-(methyl)ethyl]amino}methyl, azetidinylmethyl, pyrrolidinylmethyl, piperidinylmethyl, 1-piperidinylethyl, piperazinylmethyl, 7-azabicyclo[2.2.1]heptylmethyl, 2-azabicyclo[2.2.2]octylmethyl, {[2-(pyrrolidin-1-yl)ethyl]amino}methyl, {[2-(piperidin-1-yl)ethyl]amino}methyl, (3-fluoropyrrolidin-1-yl)methyl, (4-fluoropiperidin-1-yl)methyl, (3-hydroxypyrrolidin-1-yl)methyl, (3-hydroxypiperidin-1-yl)methyl, (4-hydroxypiperidin-1-yl)methyl, (4-trifluoromethylpiperidin-1-yl)methyl, [2,5-dimethylpyrrolidin-1-yl]methyl, (4-methylpiperidin-1-yl)methyl, (4-hydroxymethylpiperidin-1-yl)methyl, (3,3-dimethylpiperidin-1-yl)methyl, [6-(hydroxymethyl)-3-azabicyclo[3.1.0]hex-3-yl]methyl, (3-methylaminopyrrolidin-1-yl)methyl, [3-(dimethylamino)pyrrolidin-1-yl]methyl, [3-(diethylamino)pyrrolidin-1-yl]methyl, (3-phenylpyrrolidin-1-yl)methyl, (3-phenylpiperidin-1-yl)methyl, (4-phenylpiperidin-1-yl)methyl, [3-(4-fluorophenyl)piperidin-1-yl]methyl, (3-pyridin-2-ylpyrrolidin-1-yl)methyl, (4-morpholin-4-ylpiperidin-1-yl)methyl, [4-(2-oxopyrrolidin-1-yl)piperidin-1-yl]methyl, (4-pyrrolidin-1-ylpiperidin-1-yl)methyl, (4-pyridin-4-ylpiperidin-1-yl)methyl, [(4-methylpiperazin-1-yl)piperidin-1-yl]methyl, [4-(morpholin-4-ylcarbonyl)piperidin-1-yl]methyl, (4-methylpiperazin-1-yl)methyl, (4-ethylpiperazin-1-yl)methyl, [4-(2-hydroxyethyl)piperazin-1-yl]methyl, (4-isopropylpiperazin-1-yl)methyl, {4-[2-(dimethylamino)ethyl]piperazin-1-yl}methyl, (4-allylpiperazin-1-yl)methyl, (4-acetylpiperazin-1-yl)methyl, (5-butyrylhexahydropyrrolo[3,4-c]pyrrol-2(1H)-yl)methyl, [4-(2-methoxyethyl)piperazin-1-yl]methyl, [4-(methylsulfonyl)piperazin-1-yl]methyl, [4-(ethylsulfonyl)piperazin-1-yl]methyl, [4-(2-cyanophenyl)piperazin-1-yl]methyl, [4-(pyridin-2-yl)piperazin-1-yl]methyl, [4-(3-cyanopyridin-2-yl)piperazin-1-yl]methyl, [4-(3-cyanopyrazin-2-yl)piperazin-1-yl]methyl, (4-pyrimidin-2-ylpiperazin-1-yl)methyl, (4-pyrazin-2-ylpiperazin-1-yl)methyl, [4-(2-oxo-2-pyrrolidin-1-ylethyl)piperazin-1-yl]methyl, [4-(cyclopropylcarbonyl)piperazin-1-yl]methyl, {[(1,3-dimethyl-1H-pyrazol-5-yl)methyl]amino}methyl, {[2-(3,5-dimethyl-1H-pyrazol-4-yl)ethyl]amino}methyl, [methyl(tetrahydrofuran-2-ylmethyl)amino]methyl, [(5-methylpyrazin-2-yl)methyl]amino}methyl, [6-(trifluoromethyl)pyridin-3-yl]methyl}amino)methyl, [(4-methyl-1,3-thiazol-2-yl)methyl]amino}methyl, [2-(1-methyl-1H-imidazol-4-yl)ethyl]amino}methyl, [(tetrahydrofuran-2-ylmethyl)amino]methyl, [(5-methyl-2-furyl)methyl]amino}methyl, (tetrahydro-2H-pyran-4-ylmethyl)amino]methyl, (tetrahydro-2H-pyran-4-ylamino)methyl, {[2-(2-methyl-1H-indol-3-yl)ethyl]amino}methyl, (2-methoxybenzyl)amino]methyl, [(3-methoxybenzyl)

amino]methyl, {[2-(isopropylamino)ethoxy]methyl, [2-(ethylamino)ethoxy]methyl, and [2-(methylamino)ethoxy]methyl.

Suitably, the —[$CR^aR^b$]$_a$—$X^1$—[$CR^cR^d$]$_b$— moiety of formula II is group selected from methylene, ethylene, methoxymethyl, and ethoxymethyl, particularly methylene and ethoxymethyl.

A suitable value for $X^1$ is selected from a direct bond, —O— or —C(O)—, particularly a direct bond or —O—.

A suitable value for integer a is 0, 1 or 2, with the proviso that if $X^1$ is —O— then integer a is at least 1. In particular, integer a is 1 or 2.

A suitable value for integer b is 0, 1, 2, 3 or 4, particularly 0 or 1.

A suitable value for each $R^a$, $R^b$, $R^c$ and $R^d$ group present is hydrogen, halo, hydroxy or (1-4C)alkyl, particularly hydrogen or (1-4C)alkyl, and especially hydrogen or methyl.

A suitable value for $X^2$ is a direct bond, —O— or —C(O)—, particularly a direct bond.

A suitable value for integer c is 1, 2 or 3, particularly 1 or 2, and especially 2.

A suitable value for integer d is 0, 1, 2 or 3, particularly 0.

A suitable value for each $R^e$, $R^f$, $R^g$ and $R^h$ group present is hydrogen, halo, hydroxy or (1-4C)alkyl, particularly hydrogen.

Suitable values for a heterocyclic ring formed when $R^9$ and $R^{10}$ are linked include an unsubstituted azetidin-1-yl, pyrrolidin-1-yl, piperidin-1-yl, piperazin-1-yl, or morpholin-4-yl ring, particularly an azetidin-1-yl, pyrrolidin-1-yl, piperidin-1-yl, or piperazin-1-yl ring, and especially a pyrrolidin-1-yl or piperidin-1-yl ring.

Suitable values for a heterocyclic ring formed when $R^7$ and $R^8$ are linked include a substituted or unsubstituted azetidin-1-yl, pyrrolidin-1-yl, piperidin-1-yl, piperazin-1-yl, 3-azabicyclo[3.1.0]hex-3-yl, hexahydropyrrolo[3,4-c]pyrrol-2-yl, 7-azabicyclo[2.2.1]hept-7-yl, or 2-azabicyclo[2.2.2]oct-2-yl ring.

When either of $R^7$ and $R^8$ is a carbon-linked heterocyclyl (1-6C)alkyl or heterocyclyl(1-2C)alkyl group (i.e. a heterocyclyl-alkyl group wherein the heterocyclyl moiety is carbon-linked to the alkyl group) then it is suitably selected from a substituted or unsubstituted thienylalkyl, pyrimidinylalkyl, pyridazinylalkyl, furanylalkyl, tetrahydrofuranylalkyl, pyranylalkyl, tetrahydropyranylalkyl, pyridinylalkyl, pyrazinylalkyl, thiazolylalkyl, or indolylalkyl group, or from one the following particular substituent groups: 1,3-dimethyl-1H-pyrazol-5-ylalkyl, 3,5-dimethyl-1H-pyrazol-4-ylalkyl, and 1-methyl-1H-imidazol-4-ylalkyl. Particular examples of either of $R^7$ and $R^8$ when they are a heterocyclyl-(1-6C)alkyl or heterocyclyl(1-2C)alkyl group wherein the heterocyclyl moiety is carbon-linked to the alkyl group include {[(1,3-dimethyl-1H-pyrazol-5-yl)methyl]amino}methyl, {[2-(3,5-dimethyl-1H-pyrazol-4-yl)ethyl]amino}methyl, [methyl(tetrahydrofuran-2-ylmethyl)amino]methyl, [(5-methylpyrazin-2-yl)methyl]amino}methyl, [6-(trifluoromethyl)pyridin-3-yl]methyl}amino)methyl, [(4-methyl-1,3-thiazol-2-yl)methyl]amino}methyl, [2-(1-methyl-1H-imidazol-4-yl)ethyl]amino}methyl, [(tetrahydrofuran-2-ylmethyl)amino]methyl, [(5-methyl-2-furyl)methyl]amino}methyl, (tetrahydro-2H-pyran-4-ylmethyl)amino]methyl.

Suitably, $Y^1$ is a direct bond or —[$CR^{13}R^{14}$]$_x$— where integer x is 1 to 2 and $R^{13}$ and $R^{14}$ are independently selected from hydrogen and (1-4C)alkyl, particularly hydrogen.

Suitably, $X^3$ is selected from —O— and —C(O)—.

Suitably, $Q^1$ is selected from (1-6C)alkyl, (3-6C)cycloalkyl, (3-6C)cycloalkyl(1-6C)alkyl, heterocyclyl and heterocyclyl-(1-6C)alkyl.

A suitable value for $X^4$ is a direct bond, —O— or —C(O)—, particularly a direct bond.

A suitable value for integer f is 0, 1, 2 or 3, particularly 0, 1 or 2.

A suitable value for integer g is 0, 1 or 2, particularly 0.

A suitable value for each $R^i$, $R^j$, $R^k$ and $R^l$ group present is hydrogen, halo, hydroxy or (1-4C)alkyl, particularly hydrogen.

Suitably $Y^2$ is a direct bond.

A suitable value for $X^5$ is —O—, —S—, —SO—, —SO$_2$—, —C(O)—, —OC(O)— or —C(O)O—, particularly —C(O)—; and Suitably $Q^2$ is selected from (1-6C)alkyl, (3-6C)cycloalkyl, (3-6C)cycloalkyl(1-6C)alkyl, heterocyclyl, or heterocyclyl-(1-6C)alkyl group, particularly a (1-6C)alkyl, (3-6C)cycloalkyl, or a heterocyclyl group.

A suitable value for integer h is 0, 1, 2, or 3, particularly 0, 1 or 2.

A suitable value for each $R^m$ and $R^l$ group present is hydrogen, halo, hydroxy or (1-4C)alkyl, particularly hydrogen.

Suitably $R^{23}$ and $R^{24}$ are each independently selected from hydrogen or (1-6C)alkyl.

Suitably, $Y^3$ is a direct bond or —[$CR^{25}R^{26}$]$_z$— wherein z is 1 to 2 and $R^{25}$ and $R^{26}$ are independently selected from hydrogen and (1-4C)alkyl, particularly hydrogen.

Suitably, $X^6$ is —C(O)— if $Y^3$ is —[$CR^{23}R^{24}$]—, and if $Y^3$ is a direct bond, $X^6$ is selected from —SO$_2$— and —C(O)—. A particularly suitable value for $X^6$ is —C(O)— or —SO$_2$—.

Suitably, $Q^3$ is selected from (1-6C)alkyl, (3-6C)cycloalkyl, (3-6C)cycloalkyl(1-6C)alkyl, heterocyclyl, or heterocyclyl-(1-6C)alkyl group, particularly a (1-6C)alkyl, (3-6C)cycloalkyl, or a heterocyclyl group A suitable value for m is 0, 1, 2 or 3, particularly 0.

A suitable value for $R^2$, when present, is fluoro or chloro, particularly fluoro.

A suitable value for n is 0, 1, 2 or 3, particularly 0.

A suitable value for $R^3$, when present, is hydroxy, fluoro or chloro, particularly fluoro.

A suitable value for $R^4$ is amino.

Particular novel compounds of the invention include, for example, benzamide derivatives of the Formula (I), or pharmaceutically-acceptable salts thereof, wherein, unless otherwise stated, each of $R^{1a}$, $R^{1b}$, $R^{1c}$, integer m, $R^2$, integer n, $R^3$, and $R^4$ has any of the meanings defined hereinbefore or in paragraphs (1) to (29) hereinafter:—

(1) $R^{1a}$ is selected from hydrogen, amino, nitro, (1-3C)alkyl, N-(1-3C)alkylamino, N,N-di-(1-3C)alkylamino, phenyl, or piperazinyl;
and wherein:
(i) if $R^{1a}$ is N-(1-3C)alkylamino or N,N-di-(1-3C)alkylamino group, the (1-3C)alkyl moiety is optionally substituted by hydroxy;
(ii) if $R^{1a}$ is phenyl, it is optionally substituted by halo; and
(iii) if $R^{1a}$ is piperazinyl, it is optionally substituted by (1-3C)alkyl;

(2) $R^{1a}$ is selected from hydrogen, amino, nitro, (1-3C)alkyl, N-(1-3C)alkylamino, phenyl, piperazinyl, wherein:
(i) if $R^{1a}$ is N-(1-3C)alkylamino, the (1-3C)alkyl moiety is optionally substituted by hydroxy;
(ii) if $R^{1a}$ is phenyl it is optionally substituted by halo; and
(iii) if $R^{1a}$ is piperazinyl it is optionally substituted by (1-3C)alkyl;

(3) $R^{1a}$ is selected from hydrogen, amino, nitro, (1-2C)alkyl, N-(1-2C)alkylamino, phenyl, or piperazinyl, wherein
(i) if $R^{1a}$ is N-(1-2C)alkylamino, the (1-2C)alkyl moiety is optically substituted by hydroxy;
(ii) if $R^{1a}$ is phenyl it is optionally substituted by fluoro; and (iii) if $R^{1a}$ is piperazinyl it is optionally substituted by (1-2C)alkyl;

(4) $R^{1a}$ is selected from hydrogen, amino, nitro, (1-2C)alkyl, or N-(1-2C)alkylamino, wherein if $R^{1a}$ is N-(1-2C)alkylamino, the (1-2C)alkyl moiety is substituted by hydroxy;

(5) $R^{1a}$ is selected from hydrogen, amino, methyl, 2-hydroxyethylamino, and 4-methylpiperazinyl;

(6) $R^{1a}$ is selected from hydrogen, methyl, or 2-hydroxyethylamino;

(7) $R^{1a}$ is hydrogen;

(8) $R^{1a}$ is methyl;

(9) $R^{1a}$ is 2-hydroxyethylamino;

(10) $R^{1b}$ is selected from:

(i) hydrogen, halo, nitro, cyano, hydroxy, trifluoromethyl, trifluoromethoxy, amino, carboxy, carbamoyl, mercapto, sulphamoyl, (1-4C)alkyl, hydroxy(1-4C)alkyl, (2-4C)alkenyl, (2-4C)alkynyl, (3-6C)cycloalkyl, (3-6C)cycloalkyl(1-2C)alkyl, (3-6C)cycloalkenyl, (3-6C)cycloalkenyl(1-2C)alkyl, (1-4C)alkoxy, (1-4C)alkanoyloxy, N-(1-4C)alkylamino, N,N-di-[(1-4C)alkyl]amino, N-[(3-6C)cycloalkyl]amino, N,N-di-[(3-6C)cycloalkyl]amino, N-[(3-6C)cycloalkyl(1-2C)alkyl] amino, N,N-di-[(3-6C)cycloalkyl(1-2C)alkyl]amino, N-[(3-6C)cycloalkyl]-N-[(1-2C)alkyl]amino, N-[(3-6C)cycloalkyl(1-2C)alkyl]-N-[(1-4C)alkyl]amino, N-(1-4C)alkanoylamino, N,N-di-[(1-4C)alkanoyl] amino, N-[(1-4C)alkoxy(1-4C)alkyl]amino, N,N-di-[(1-4C)alkoxy(1-4C)alkyl]amino, N-[(1-4C)alkoxy(1-4C)alkyl]-N-[(1-4C)alkyl]amino, N-(1-4C)alkylcarbamoyl, N,N-di-[(1-4C)alkyl]carbamoyl, (1-4C)alkylthio, (1-4C)alkylsulphinyl, (1-4C)alkylsulphonyl, (1-4C)alkoxycarbonyl, N-(1-4C)alkylsulphamoyl, N,N-di-[(1-4C)alkyl]sulphamoyl, aryl, aryl-(1-2C)alkyl, a carbon linked heterocyclyl group, or a heterocyclyl-(1-2C)alkyl group wherein the heterocyclyl moiety is carbon-linked to the alkyl group; or (ii) a group of sub-formula II:

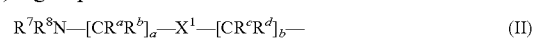

$$R^7R^8N\text{—}[CR^aR^b]_a\text{—}X^1\text{—}[CR^cR^d]_b\text{—} \quad \text{(II)}$$

wherein:

$X^1$ is selected from a direct bond, —O— or —C(O)—;

integer a is 1, 2, or 3;

integer b is 0, 1, or 2;

each $R^a$, $R^b$, $R^c$ and $R^d$ group present is independently selected from hydrogen, or (1-2C)alkyl;

$R^7$ and $R^8$ are independently selected from hydrogen, (1-6C)alkyl, hydroxy(1-4C)alkyl, halo(1-4C)alkyl, (2-4C)alkenyl, (3-6C)cycloalkyl, (3-6C)cycloalkyl(1-2C)alkyl, (1-4C)alkoxy(1-4C)alkyl, (1-4C)alkanoyl, (3-6C)cycloalkenyl, (3-6C)cycloalkenyl(1-2C)alkyl, aryl, aryl(1-2C)alkyl, heterocyclyl;

a heterocyclyl-(1-2C)alkyl group wherein the heterocyclyl moiety is carbon-linked to the alkyl group, and is either selected from a substituted or unsubstituted thienyl, pyrimidinyl, pyridazinyl, furanyl, tetrahydrofuranyl, pyranyl, tetrahydropyranyl, pyridinyl, pyrazinyl, thiazolyl, or indolyl group, or from one the following particular substituent groups: 1,3-dimethyl-1H-pyrazol-5-yl, 3,5-dimethyl-1H-pyrazol-4-yl, and 1-methyl-1H-imidazol-4-yl;

a group of sub-formula III:

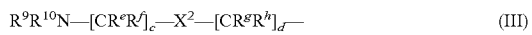

$$R^9R^{10}N\text{—}[CR^eR^f]_c\text{—}X^2\text{—}[CR^gR^h]_d\text{—} \quad \text{(III)}$$

wherein:

$X^2$ is selected from a direct bond, —O— or —C(O)—;

integer c is 1, 2 or 3;

integer d is 0, 1, or 2;

each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, hydroxy(1-4C)alkyl, halo(1-4C)alkyl, (3-6C)cycloalkyl, (3-6C)cycloalkyl(1-2C)alkyl, (1-4C)alkoxy(1-4C)alkyl, or $R^9$ and $R^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by hydroxy, halo, (1-4C)allyl, carbamoyl, or —[CH$_2$]$_e$—NR$^{11}$R$^{12}$ (wherein integer e is 0, 1 or 2, and $R^{11}$ and $R^{12}$ are independently selected from hydrogen, (1-4C)alkyl, (3-6C)cycloalkyl or (3-6C)cycloalkyl(1-2C)alkyl);

or $R^7$ and $R^8$ are linked so that, together with the nitrogen atom to which they are attached, they form a 4 to 10-membered heterocyclic ring, said heterocyclic ring optionally comprising, in addition to the nitrogen atom to which $R^7$ and $R^8$ are attached, one or two further nitrogen atoms; or (iii) a group of the sub-formula IV:

$$Q^1\text{-}X^3\text{—}Y^1\text{—} \quad \text{(IV)}$$

wherein:

$Y^1$ is a direct bond or —[CR$^{13}$R$^{14}$]$_x$— where integer x is 1 to 4 and $R^{13}$ and $R^{14}$ are independently selected from hydrogen, halo and (1-4C)alkyl;

$X^3$ is selected from —O—, —S—, —SO—, —SO$_2$—, —C(O)—, —OC(O)— and —C(O)O—, with the proviso that $Y^1$ is not a direct bond if $X^3$ is —C(O)—; and $Q^1$ is selected from (1-4C)alkyl, (3-6C)cycloalkyl, (3-6C)cycloalkyl(1-4C)alkyl, (3-6C)cycloalkenyl, (3-6C)cycloalkenyl(1-2C)alkyl, aryl, aryl-(1-2C)alkyl, heterocyclyl, heterocyclyl-(1-2C)alkyl, or $R^{15}R^{16}$N-(1-2C)alkyl (wherein $R^{15}$ and $R^{16}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C) alkyl, (3-6C)cycloalkenyl, or (3-6C)cycloalkenyl(1-2C)alkyl);

and wherein any heterocyclyl ring within a $R^{1b}$ substituent group (apart from those for which particular substituents are expressly stated above, such as heterocyclyl rings formed when $R^9$ and $R^{10}$ are linked) is optionally substituted on carbon by one or more $Z^1$ substituent groups (for example 1, 2 or 3), which may be the same or different, selected from:

(a) halo, nitro, cyano, hydroxy, trifluoromethyl, trifluoromethoxy, amino, carboxy, carbamoyl, mercapto, sulphamoyl, (1-4C)alkyl, hydroxy(1-4C)alkyl, (2-4C)alkenyl, (2-4C)alkynyl, (1-4C)alkoxy, (1-4C)alkanoyl, (1-4C)alkanoyloxy, (1-4C)alkoxy-(1-4C)alkyl, (1-4C)alkoxycarbonyl, halo(1-4C)alkyl, N-[(1-4C)alkyl] amino, N,N-di-[(1-4C)alkyl]amino, N-(1-4C)alkylcarbamoyl, N,N-di-[(1-4C)alkyl]carbamoyl, (1-4C)alkylthio, (1-4C)alkylsulphinyl, (1-4C)alkylsulphonyl, N-(1-4C)alkylsulphamoyl, N,N-di-[(1-4C)alkyl]sulphamoyl, aryl, aryl-(1-2C)alkyl, heterocyclyl, heterocyclyl-(1-2C)alkyl, (b) a group of the sub-formula V:

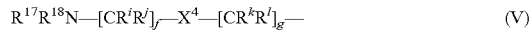

$$R^{17}R^{18}N\text{—}[CR^iR^j]_f\text{—}X^4\text{—}[CR^kR^l]_g\text{—} \quad \text{(V)}$$

wherein
X⁴ is selected from a direct bond, or —O—;
integer f is 0, 1, or 2, with the proviso that integer f is at least 1 if X⁴ is —O—;
integer g is 0, or 1;
each $R^i$, $R^j$, $R^k$ and $R^l$ group present is independently selected from hydrogen or (1-2C)alkyl;
$R^{17}$ and $R^{18}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl; or (c) a group of the sub-formula VI:

$$Q^2\text{-}X^5\text{—}Y^2\text{—} \quad \text{(VI)}$$

wherein:
$Y^2$ is a direct bond or —[CR¹⁹R²⁰]$_y$— wherein integer y is 1 or 2 and $R^{19}$ and $R^{20}$ are independently selected from hydrogen or (1-2C)alkyl;
$X^5$ is selected from —O— or —C(O)—; and
$Q^2$ is selected from (1-4C)alkyl, (3-6C)cycloalkyl, (3-6C)cycloalkyl(1-2C)alkyl, (3-6C)cycloalkenyl, (3-6C)cycloalkenyl(1-2C)alkyl, aryl, aryl-(1-2C)alkyl, heterocyclyl, heterocyclyl-(1-2C)alkyl, $R^{21}R^{22}$N-(1-2C)alkyl (wherein $R^{21}$ and $R^{22}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl);

and wherein if any heterocyclyl group within a $R^{1b}$ substituent group contains an unsubstituted nitrogen atom, then, unless any particular substituents are expressly stated in the definition above (e.g. such as when $R^9$ and $R^{10}$ are linked to form a heterocyclic ring together with the nitrogen atom to which they are attached), the nitrogen atom may be optionally substituted by one or more $Z^2$ substituent groups (for example 1, 2 or 3), which may be the same or different, selected from:

(a) trifluoromethyl, carboxy, carbamoyl, (1-4C)alkyl, hydroxy(1-4C)alkyl, (2-4C)alkenyl, (1-4C)alkanoyl, (1-4C)alkoxy-(1-4C)alkyl, (1-4C)alkoxycarbonyl, halo(1-4C)alkyl, N-(1-4C)alkylamino-(1-2C)alkyl, N,N-di-[(1-4C)alkyl]amino-(1-2C)alkyl, (1-4C)alkylsulphonyl, aryl, aryl-(1-2C)alkyl, heterocyclyl, heterocyclyl-(1-2C)alkyl; or (b) a group of the formula VII:

$$R^{23}R^{24}N\text{—}[CR^mR^n]_h\text{—} \quad \text{(VII)}$$

wherein
integer h is 0, 1, 2 or 3;
each $R^m$ and $R^n$ group present is independently selected from hydrogen, halo, hydroxy or (1-4C)alkyl;
$R^{23}$ and $R^{24}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl; or (c) a group of the formula VIII:

$$Q^3\text{-}X^6\text{—}Y^3\text{—} \quad \text{(VIII)}$$

wherein $Y^3$ is a direct bond or —[CR²⁵R²⁶]$_z$— wherein z is 1 to 3 and $R^{25}$ and $R^{26}$ are independently selected from hydrogen or (1-2C)alkyl;
$X^6$ is selected from —O— or —C(O)—, if $Y^3$ is —[CR²³R²⁴]$_z$—, and if $Y^3$ is a direct bond, $X^6$ is selected from —SO₂— or —C(O)—; and $Q^3$ is selected from (1-4C)alkyl, (3-6C)cycloalkyl, (3-6C)cycloalkyl(1-2C)alkyl, aryl, aryl-(1-2C)alkyl, heterocyclyl, heterocyclyl-(1-2C)alkyl or $R^{27}R^{28}$N-(1-2C)alkyl (wherein $R^{27}$ and $R^{28}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl);

and wherein any heterocyclyl group within a $Z^1$ or $Z^2$ substituent group optionally bears one or more substituent groups (for example 1, 2 or 3), which may be the same or different, selected from halo, cyano, trifluoromethyl, amino, carboxy, carbamoyl, mercapto, sulphamoyl, (1-4C)alkyl, hydroxy(1-4C)alkyl, halo(1-4C)alkyl, (2-4C)alkenyl, (2-4C)alkynyl, (1-4C)alkoxy, (1-4C)alkanoyl, (1-4C)alkanoyloxy, N-[(1-4C)alkyl]amino, and N,N-di-[(1-4C)alkyl]amino;

and wherein any non-aromatic heterocyclyl group within a $R^{1b}$ substituent (including optional substituent groups $Z^1$ and $Z^2$) optionally bears 1 or 2 oxo substituents;

and wherein any alkyl, alkenyl, alkynyl, alkoxy, alkanoyl, alkanoyloxy, cycloalkyl, or cycloalkenyl group within a $R^{1b}$ substituent group (including optional substituent groups $Z^1$ and $Z^2$) is, unless particular substituents are expressly stated above, optionally substituted by one or more $Z^3$ substituent groups (for example 1, 2 or 3), which may be the same or different, selected from halo, cyano, mercapto, (1-4C)alkoxy, trifluoromethyl, or —NR²⁹R³⁰ wherein each of $R^{29}$ and $R^{30}$ is independently selected from hydrogen, (1-4C)alkyl, (1-4C)alkoxy, (3-6C)cycloalkyl, (3-6C)cycloalkyl(1-2C)alkyl;

and wherein any aryl group within a $R^{1b}$ substituent group (including optional substituent groups $Z^1$ and $Z^2$) is optionally substituted by one or more $Z^4$ substituent groups (for example 1, 2 or 3), which may be the same or different, selected from halo, nitro, cyano, hydroxy, amino, (1-4C)alkyl, hydroxy(1-4C)alkyl, halo(1-4C)alkyl, (1-4C)alkoxy, (1-4C)alkanoyl, N-[(1-4C)alkyl]amino, N,N-di-[(1-4C)alkyl]amino, carbamoyl, N-(1-4C)alkylcarbamoyl, N,N-di-[(1-4C)alkyl]carbamoyl;

(11) $R^{1b}$ is selected from:
(i) hydrogen, halo, nitro, cyano, hydroxy, trifluoromethyl, trifluoromethoxy, amino, carboxy, carbamoyl, mercapto, sulphamoyl, (1-4C)alkyl, hydroxy(1-4C)alkyl, N-(1-4C)alkylamino, or N,N-di-[(1-4C)alkyl]amino; or
(ii) a group of sub-formula II:

$$R^7R^8N\text{—}[CR^aR^b]_a\text{—}X\text{—}[CR^cR^d]_b\text{—} \quad \text{(II)}$$

wherein:
$X^1$ is selected from a direct bond, —O— or —C(O)—;
integer a is 1, 2, or 3;
integer b is 0, 1, or 2;
each $R^a$, $R^b$, $R^c$ and $R^d$ group present is independently selected from hydrogen, or (1-2C)alkyl;
$R^7$ and $R^8$ are independently selected from hydrogen, (1-6C)alkyl, hydroxy(1-4C)alkyl, halo(1-4C)alkyl, (2-4C)alkenyl, (3-6C)cycloalkyl, (3-6C)cycloalkyl(1-2C)alkyl, (1-4C)alkoxy(1-4C)alkyl, (1-4C)alkanoyl, (3-6C)cycloalkenyl, (3-6C)cycloalkenyl(1-2C)alkyl, aryl, aryl(1-2C)alkyl, heterocyclyl;
a heterocyclyl-(1-2C)alkyl group wherein the heterocyclyl moiety is carbon-linked to the alkyl group and is either selected from a substituted or unsubstituted furanyl, tetrahydrofuranyl, pyranyl, tetrahydropyranyl, pyridinyl, pyrazinyl, thiazolyl, or indolyl group, or from one the following particular substituent groups: 1,3-dimethyl-1H-pyrazol-5-yl, 3,5-dimethyl-1H-pyrazol-4-yl, and 1-methyl-1H-imidazol-4-yl;

a group of sub-formula III:

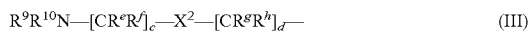

wherein:

$X^2$ is selected from a direct bond, —O— or —C(O)—;

integer c is 1, 2 or 3;

integer d is 0, 1, or 2;

each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, hydroxy(1-4C)alkyl, halo(1-4C)alkyl, (3-6C)cycloalkyl, (3-6C)cycloalkyl(1-2C)alkyl, (1-4C)alkoxy(1-4C)alkyl, or $R^9$ and $R^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by hydroxy, halo, (1-4C)alkyl, carbamoyl, or —[CH$_2$]$_e$— NR$^{11}$R$^{12}$ (wherein integer e is 0, 1 or 2, and $R^{11}$ and $R^{12}$ are independently selected from hydrogen, (1-4C)alkyl, (3-6C)cycloalkyl or (3-6C) cycloalkyl(1-2C)alkyl);

or $R^7$ and $R^8$ are linked so that, together with the nitrogen atom to which they are attached, they form a 4 to 10-membered heterocyclic ring, said heterocyclic ring optionally comprising, in addition to the nitrogen atom to which $R^7$ and $R^8$ are attached, one or two further nitrogen atoms; or and wherein any heterocyclyl ring within a $R^{1b}$ substituent group (apart from those for which particular substituents are expressly stated above, such as heterocyclyl rings formed when $R^9$ and $R^{10}$ are linked) is optionally substituted on carbon by one or more $Z^1$ substituent groups (for example 1, 2 or 3), which may be the same or different, selected from:

(a) halo, nitro, cyano, hydroxy, trifluoromethyl, trifluoromethoxy, amino, carboxy, carbamoyl, mercapto, sulphamoyl, (1-4C)alkyl, hydroxy(1-4C)alkyl, (2-4C)alkenyl, (2-4C)alkynyl, (1-4C)alkoxy, (1-4C)alkanoyl, (1-4C)alkanoyloxy, (1-4C)alkoxy-(1-4C)alkyl, (1-4C)alkoxycarbonyl, halo(1-4C)alkyl, N-[(1-4C)alkyl]amino, N,N-di-[(1-4C)alkyl]amino, N-(1-4C)alkylcarbamoyl, N,N-di-[(1-4C)alkyl]carbamoyl, (1-4C)alkylthio, (1-4C)alkylsulphinyl, (1-4C)alkylsulphonyl, N-(1-4C)alkylsulphamoyl, N,N-di-[(1-4C)alkyl]sulphamoyl, aryl, aryl-(1-2C)alkyl, heterocyclyl, heterocyclyl-(1-2C)alkyl, (b) a group of the sub-formula V:

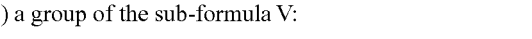

wherein $X^4$ is selected from a direct bond, or —O—;

integer f is 0, 1, or 2, with the proviso that integer f is at least 1 if $X^4$ is —O—;

integer g is 0, or 1;

each $R^i$, $R^j$, $R^k$ and $R^l$ group present is independently selected from hydrogen or (1-2C)alkyl;

$R^{17}$ and $R^{18}$ are each independently selected from hydrogen, (1-4C)alkyl, (1-4C)alkoxy, (1-4C)alkoxy (1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl; or (c) a group of the sub-formula VI:

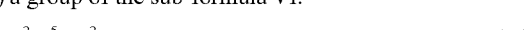

wherein:

$Y^2$ is a direct bond or —[CR$^{19}$R$^{20}$]$_y$— wherein integer y is 1 or 2 and $R^{19}$ and $R^{20}$ are independently selected from hydrogen or (1-2C)alkyl;

$X^5$ is selected from —O— or —C(O)—; and $Q^2$ is selected from (1-4C)alkyl, (3-6C)cycloalkyl, (3-6C)cycloalkyl(1-2C)alkyl, (3-6C)cycloalkenyl, (3-6C)cycloalkenyl(1-2C)alkyl, aryl, aryl-(1-2C)alkyl, heterocyclyl, heterocyclyl-(1-2C)alkyl, $R^{21}R^{22}$N-(1-2C)alkyl (wherein $R^{21}$ and $R^{22}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C) alkyl, (3-6C)cycloalkenyl, or (3-6C)cycloalkenyl(1-2C)alkyl);

and wherein if any heterocyclyl group within a $R^{1b}$ substituent group contains an unsubstituted nitrogen atom, then, unless any particular substituents are expressly stated in the definition above (e.g. such as when $R^9$ and $R^{10}$ are linked to form a heterocyclic ring together with the nitrogen atom to which they are attached), the nitrogen atom may be optionally substituted by one or more $Z^2$ substituent groups (for example 1, 2 or 3), which may be the same or different, selected from:

(a) trifluoromethyl, carboxy, carbamoyl, (1-4C)alkyl, hydroxy(1-4C)alkyl, (2-4C)alkenyl, (1-4C)alkanoyl, (1-4C)alkoxy-(1-4C)alkyl, (1-4C)alkoxycarbonyl, halo (1-4C)alkyl, N-(1-4C)alkylamino-(1-2C)alkyl, N,N-di-[(1-4C)alkyl]amino-(1-2C)alkyl, (1-4C)alkylsulphonyl, aryl, aryl-(1-2C)alkyl, heterocyclyl, heterocyclyl-(1-2C)alkyl; or (b) a group of the formula VII:

wherein integer h is 0, 1, or 2;

each $R^m$ and $R^n$ group present is independently selected from hydrogen or (1-2C)alkyl;

$R^{23}$ and $R^{24}$ are each independently selected from hydrogen, (1-4C)alkyl, (1-4C)alkoxy, (1-4C)alkoxy (1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl; or (c) a group of the formula VIII:

wherein $Y^3$ is a direct bond or —[CR$^{25}$R$^{26}$]$_z$— wherein z is 1 to 2 and $R^{25}$ and $R^{26}$ are independently selected from hydrogen or (1-2C)alkyl;

$X^6$ is selected from —O— or —C(O)—, if $Y^3$ is —[CR$^{23}$R$^{24}$], and if $Y^3$ is a direct bond, $X^6$ is selected from —SO$_2$— or —C(O)—; and $Q^3$ is selected from (1-4C)alkyl, (3-6C)cycloalkyl, (3-6C)cycloalkyl(1-2C)alkyl, aryl, aryl-(1-2C)alkyl, heterocyclyl, heterocyclyl-(1-2C)alkyl or $R^{27}R^{28}$N-(1-2C)alkyl (wherein $R^{27}$ and $R^{28}$ are each independently selected from hydrogen, (1-4C)alkyl, (1-4C) alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C) alkyl);

and wherein any heterocyclyl group within a $Z^1$ or $Z^2$ substituent group optionally bears one or more substituent groups (for example 1, 2 or 3), which may be the same or different, selected from halo, cyano, trifluoromethyl, amino, carboxy, carbamoyl, mercapto, sulphamoyl, (1-4C)alkyl, hydroxy(1-4C)alkyl, halo(1-4C)alkyl, (2-4C)alkenyl, (2-4C)

alkynyl, (1-4C)alkoxy, (1-4C)alkanoyl, (1-4C)alkanoyloxy, N-[(1-4C)alkyl]amino, and N,N-di-[(1-4C)alkyl]amino;

and wherein any non-aromatic heterocyclyl group within a $R^{1b}$ substituent (including optional substituent groups $Z^1$ and $Z^2$) optionally bears 1 or 2 oxo substituents;

and wherein any alkyl, alkenyl, alkynyl, alkoxy, alkanoyl, alkanoyloxy, cycloalkyl, or cycloalkenyl group within a $R^{1b}$ substituent group (including optional substituent groups $Z^1$ and $Z^2$) is, unless particular substituents are expressly stated above, optionally substituted by one or more $Z^3$ substituent groups (for example 1, 2 or 3), which may be the same or different, selected from halo, cyano, mercapto, (1-4C)alkoxy, trifluoromethyl, or —$NR^{29}R^{30}$ wherein each of $R^{29}$ and $R^{30}$ is independently selected from hydrogen, (1-4C)alkyl, (1-4C)alkoxy, (3-6C)cycloalkyl, (3-6C)cycloalkyl(1-2C)alkyl;

and wherein any aryl group within a $R^{1b}$ substituent group (including optional substituent groups $Z^1$ and $Z^2$) is optionally substituted by one or more $Z^4$ substituent groups (for example 1, 2 or 3), which may be the same or different, selected from halo, nitro, cyano, hydroxy, amino, (1-4C)alkyl, hydroxy(1-4C)alkyl, halo(1-4C)alkyl, (1-4C)alkoxy, (1-4C)alkanoyl, N-[(1-4C)alkyl]amino, N,N-di-[(1-4C)alkyl]amino, carbamoyl, N-(1-4C)alkylcarbamoyl, N,N-di-[(1-4C)alkyl]carbamoyl;

(12) $R^{1b}$ is selected from:
(i) hydrogen, halo, nitro, cyano, hydroxy, trifluoromethyl, trifluoromethoxy, 1 amino, carboxy, carbamoyl, mercapto, sulphamoyl, (1-4C)alkyl, hydroxy(1-4C)alkyl, N-(1-4C)alkylamino, or N,N-di-[(1-4C)alkyl]amino; or
(ii) a group of sub-formula II:

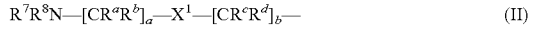
(II)

wherein:
$X^1$ is selected from a direct bond, —O— or —C(O)—;
integer a is 1, 2, or 3;
integer b is 0, 1, or 2;
each $R^a$, $R^b$, $R^c$ and $R^d$ group present is independently selected from hydrogen or (1-2C)alkyl;
$R^7$ and $R^8$ are independently selected from hydrogen, (1-6C)alkyl, hydroxy(1-4C)alkyl, halo(1-4C)alkyl, (2-4C)alkenyl, (3-6C)cycloalkyl, (3-6C)cycloalkyl(1-2C)alkyl, (1-4C)alkoxy(1-4C)alkyl;
an aryl group which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
an aryl(1-2C)alkyl group the aryl moiety of which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a heterocyclyl-(1-2C)alkyl group wherein the heterocyclyl moiety is carbon-linked to the alkyl group and is either selected from the group consisting of a furanyl, tetrahydrofuranyl, pyranyl, tetrahydropyranyl, pyridinyl, pyrazinyl, thiazolyl, indolyl group, each of which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

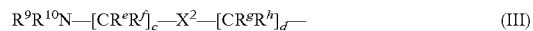
(III)

wherein:
$X^2$ is selected from a direct bond, —O— or —C(O)—;
integer c is 1, 2 or 3;
integer d is 0, 1, or 2;
each $R^e$, $R^f$, $R^g$ and $R^h$ group present is independently selected from hydrogen or (1-2C)alkyl;
$R^9$ and $R^{10}$ are independently selected from hydrogen, (1-4C)alkyl, hydroxy(1-4C)alkyl, halo(1-4C)alkyl, (3-6C)cycloalkyl, (3-6C)cycloalkyl(1-2C)alkyl, (1-4C)alkoxy(1-4C)alkyl, or $R^9$ and $R^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by one to three substituents selected from the group consisting of hydroxy, halo, (1-4C)alkyl, carbamoyl, or —$[CH_2]_e$—$NR^{11}R^{12}$ (wherein integer e is 0, 1 or 2, and $R^{11}$ and $R^{12}$ are independently selected from hydrogen, (1-4C)alkyl, (3-6C)cycloalkyl or (3-6C)cycloalkyl(1-2C)alkyl);

or $R^7$ and $R^9$ are linked so that, together with the nitrogen atom to which they are attached, they form a 4 to 10-membered heterocyclic ring, said heterocyclic ring optionally comprising, in addition to the nitrogen atom to which $R^7$ and $R^8$ are attached, one or two further nitrogen atoms, and wherein said heterocylic ring is optionally substituted on carbon by one to three substituents selected from:
(a) halo, nitro, cyano, hydroxy, trifluoromethyl, amino, carboxy, carbamoyl, mercapto, sulphamoyl, (1-4C)alkyl, hydroxy(1-4C)alkyl, (2-4C)alkenyl, (2-4C)alkynyl, (1-4C)alkoxy, (1-4C)alkanoyl, halo(1-4C)alkyl, N-[(1-4C)alkyl]amino, N,N-di-[(1-4C)alkyl]amino, an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy; or (b) a group of the sub-formula V:

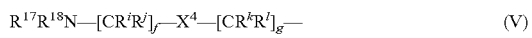
$$R^{17}R^{18}N-[CR^iR^j]_f-X^4-[CR^kR^l]_g- \quad (V)$$

wherein
X⁴ is selected from a direct bond, or —O—;
integer f is 0, 1, or 2, with the proviso that integer f is at least 1 if X⁴ is —O—;
integer g is 0, or 1;
each $R^i$, $R^j$, $R^k$ and $R^l$ group present is hydrogen;
$R^{17}$ and $R^{18}$ are each independently selected from hydrogen, (1-4C)alkyl, (1-4C)alkoxy, (1-4C)alkoxy(1-4C)alkyl, (1-4C)alkanoyl, (3-6C)cycloalkyl, (3-6C)cycloalkyl(1-2C)alkyl, (3-6C)cycloalkenyl, or (3-6C)cycloalkenyl(1-2C)alkyl; or (c) a group of the sub-formula VI:

$$Q^2-X^5-Y^2- \quad (VI)$$

wherein:
$Y^2$ is a direct bond or $-[CR^{19}R^{20}]_y-$ wherein integer y is 1 or 2 and $R^{19}$ and $R^{20}$ are independently selected from hydrogen or (1-2C)alkyl;
$X^5$ is selected from —O— or —C(O)—; and
$Q^2$ is selected from
an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
and, if said heterocyclic ring comprises a nitrogen atom then said nitrogen is optionally substituted by one or more substituent groups (for example 1, 2 or 3), which may be the same or different, selected from:
(a) (1-4C)alkyl, hydroxy(1-4C)alkyl, (2-4C)alkenyl, (1-4C)alkanoyl, (1-4C)alkoxy-(1-4C)alkyl, halo(1-4C)alkyl,
an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

(b) a group of the formula VII:

$$R^{23}R^{24}N-[CR^mR^n]_h- \quad (VII)$$

wherein
integer h is 0, 1, or 2;
each $R^m$ and $R^n$ group present is hydrogen;
$R^{23}$ and $R^{24}$ are each independently selected from hydrogen or (1-4C)alkyl; or (c) a group of the formula VIII:

$$Q^3-X^6-Y^3- \quad (VIII)$$

wherein $Y^3$ is a direct bond or $-[CR^{25}R^{26}]_z-$ wherein z is 1 to 2 and $R^{25}$ and $R^{26}$ are independently selected from hydrogen or (1-2C)alkyl;
$X^6$ is selected from —O— or C(O)—, if $Y^3$ is —[CR²³R²⁴], and if $Y^3$ is a direct bond, $X^6$ is selected from —S—, —SO—, —SO₂— or —C(O)—; and
$Q^3$ is selected from (1-4C)alkyl, (3-6C)cycloalkyl, (3-6C)cycloalkyl(1-2C)alkyl;
an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;
and wherein any non-aromatic heterocyclyl group within a $R^{1b}$ substituent group optionally bears 1 or 2 oxo substituents;
(13) $R^{1b}$ is selected from:
(i) hydrogen, halo, cyano, hydroxy, amino, (1-4C)alkyl, hydroxy(1-4C)alkyl, N-(1-4C)alkylamino, or N,N-di-[(1-4C)alkyl]amino; or
(ii) a group of sub-formula II:

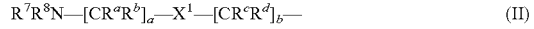
$$R^7R^8N-[CR^aR^b]_a-X^1-[CR^cR^d]_b- \quad (II)$$

wherein:
$X^1$ is selected from a direct bond, or —O—;
integer a is 1, 2 or 3;
integer b is 0, 1 or 2;
each $R^a$, $R^b$, $R^c$ and $R^d$ group present is independently selected from hydrogen or (1-2C)alkyl;
$R^7$ and $R^8$ are independently selected from hydrogen; (1-6C)alkyl; hydroxy(1-4C)alkyl; halo(1-4C)alkyl;

(2-4C)alkenyl; (3-6C)cycloalkyl; (3-6C)cycloalkyl(1-2C)alkyl; (1-4C)alkoxy(1-4C)alkyl;

an aryl group which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

an aryl(1-2C)alkyl group the aryl moiety of which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is carbon-linked to the alkyl group and is either selected from the group consisting of a furanyl, tetrahydrofuranyl, pyranyl, tetrahydropyranyl, pyridinyl, pyrazinyl, thiazolyl, indolyl group, each of which is unsubstituted or substituted with one to three substituents selected from the group consisting of halo, nitro, cyano, hydroxy, amino, (1-4C)alkyl, hydroxy(1-4C)alkyl, halo(1-4C)alkyl, (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

$$R^9R^{10}N-[CR^eR^f]_c-X^2-[CR^gR^h]_d-\qquad(III)$$

wherein:
$X^2$ is selected from a direct bond, —O— or —C(O)—;
integer c is 1, 2 or 3;
integer d is 0, 1 or 2;
each $R^e$, $R^f$, $R^g$ and $R^h$ group present is independently selected from hydrogen or (1-2C)alkyl;
$R^9$ and $R^{10}$ are independently selected from hydrogen, (1-4C)alkyl, hydroxy(1-4C)alkyl, halo(1-4C)alkyl, (3-6C)cycloalkyl, (3-6C)cycloalkyl(1-2C)alkyl, (1-4C)alkoxy(1-4C)alkyl, or $R^9$ and $R^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by one to three substituents selected from the group consisting of hydroxy, halo, or (1-4C)alkyl;

or $R^7$ and $R^8$ are linked so that, together with the nitrogen atom to which they are attached, they form a 4 to 10-membered heterocyclic ring, said heterocyclic ring optionally comprising, in addition to the nitrogen atom to which $R^7$ and $R^8$ are attached, one or two further nitrogen atoms, and wherein said heterocylic ring is optionally substituted on carbon by one to three substituents selected from:

(a) halo, nitro, cyano, hydroxy, trifluoromethyl, amino, carboxy, carbamoyl, mercapto, sulphamoyl, (1-4C)alkyl, hydroxy(1-4C)alkyl, (2-4C)alkenyl, (2-4C)alkynyl, (1-4C)alkoxy, (1-4C)alkanoyl, halo(1-4C)alkyl, N-[(1-4C)alkyl]amino, N,N-di-[(1-4C)alkyl]amino, an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

(b) a group of the sub-formula V:

$$R^{17}R^{18}N-[CR^iR^j]_f-X^4-[CR^kR^l]_g-\qquad(V)$$

wherein
$X^4$ is selected from a direct bond, or —O—;
integer f is 0, 1, or 2, with the proviso that integer f is at least 1 if $X^4$ is ~O—;
integer g is 0, or 1;
each $R^i$, $R^j$, $R^k$ and $R^l$ group present is hydrogen;
$R^{17}$ and $R^{18}$ are each independently selected from hydrogen, (1-4C)alkyl, (3-6C)cycloalkyl, or (3-6C)cycloalkyl(1-2C)alkyl; or (c) a group of the sub-formula VI:

$$Q^2-X^5-Y^2-\qquad(VI)$$

wherein:
$Y^2$ is a direct bond or —[CR^{19}R^{20}]_y— wherein integer y is 1 or 2 and $R^{19}$ and $R^{20}$ are independently selected from hydrogen or (1-2C)alkyl;
$X^5$ is selected from —O— or —C(O)—; and
$Q^2$ is selected from
a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

and, if said heterocyclic ring comprises a nitrogen atom then said nitrogen is optionally substituted by one or more substituent groups (for example 1, 2 or 3), which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl, halo(1-4C)alkyl;

an aryl group which is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

an aryl-(1-2C)alkyl wherein the aryl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

(b) a group of the formula VII:

$$R^{23}R^{24}N—[CR^mR^n]_h— \qquad (VII)$$

wherein
integer h is 0, 1, or 2;
each $R^m$ and $R^n$ group present is hydrogen;
$R^{23}$ and $R^{24}$ are each independently selected from hydrogen or (1-4C)alkyl; or (c) a group of the formula VIII:

$$Q^3—X^6—Y^3— \qquad (VIII)$$

wherein $Y^3$ is a direct bond or —$[CR^{25}R^{26}]_z$— wherein z is 1 to 2 and $R^{25}$ and $R^{26}$ are independently selected from hydrogen or (1-2C)alkyl;

$X^6$ is selected from —O— or —C(O)—, if $Y^3$ is —$[CR^{23}R^{24}]_z$—, and if $Y^3$ is a direct bond, $X^6$ is selected from —S—, —SO—, —SO$_2$— or —C(O)—; and $Q^3$ is selected from (1-4C)alkyl, (3-6C)cycloalkyl, (3-6C)cycloalkyl(1-2C)alkyl, a 4, 5, 6 or 7-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

and wherein any non-aromatic heterocyclyl group within a $R^{1b}$ substituent group optionally bears 1 or 2 oxo substituents;

(14) $R^{1b}$ is selected from:
(i) hydrogen, cyano, amino, (1-4C)alkyl, hydroxy(1-4C)alkyl; or
(ii) a group of sub-formula II:

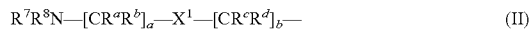

$$R^7R^8N—[CR^aR^b]_a—X^1—[CR^cR^d]_b— \qquad (II)$$

wherein:
$X^1$ is selected from a direct bond, or —O—;
integer a is 1, 2, or 3;
integer b is 0, 1, or 2;

each $R^a$, $R^b$, $R^c$ and $R^d$ group present is independently selected from hydrogen or (1-2C)alkyl;

$R^7$ and $R^8$ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;

an aryl(1-2C)alkyl group the aryl moiety of which is unsubstituted or substituted with one to three substituents selected from the group consisting of halo, cyano, hydroxy, amino, (1-4C)alkyl, or (1-4C)alkoxy;

a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C)alkoxy;

a heterocyclyl-(1-2C)alkyl group wherein the heterocyclyl moiety is carbon-linked to the alkyl group and is either selected from the group consisting of a furanyl, tetrahydrofuranyl, pyranyl, tetrahydropyranyl, pyridinyl, pyrazinyl, thiazolyl, indolyl group, each of which is unsubstituted or substituted with one to three substituents selected from the group consisting of halo, cyano, hydroxy, amino, (1-4C)alkyl, halo(1-4C)alkyl or (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

$$R^9R^{10}N—[CR^eR^f]_c—X^2—[CR^gR^h]_d— \qquad (III)$$

wherein:
$X^2$ is selected from a direct bond, or —O—;
integer c is 1, 2 or 3;
integer d is 0, 1, or 2;
each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, (3-6C)cycloalkyl, (3-6C)cycloalkyl(1-2C)alkyl, or $R^9$ and $R^{10}$ are linked so that, together with the nitrogen atom to which they are attached, they form a 4,5-, or 6-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by one to three substituents selected from the group consisting of hydroxy, halo, or (1-4C)alkyl;

or $R^7$ and $R^8$ are linked so that, together with the nitrogen atom to which they are attached, they form a 4 to 8-membered heterocyclic ring, said heterocyclic ring optionally comprising, in addition to the nitrogen atom to which $R^7$ and $R^9$ are attached, one or two further nitrogen atoms, and wherein said heterocyclylic ring is optionally substituted on carbon by one to three substituents selected from:

(a) halo, cyano, hydroxy, trifluoromethyl, amino, (1-4C)alkyl, hydroxy(1-4C)alkyl, halo(1-4C)alkyl, N-[(1-4C)alkyl]amino, N,N-di-[(1-4C)alkyl]amino, an aryl group which is optionally substituted with one to three substituents selected from the group consisting of halo, cyano, hydroxy, amino, (1-4C)alkyl, or (1-4C)alkoxy;

an aryl-(1-2C)alkyl wherein the aryl moiety is optionally substituted with one to three substituents selected from the group consisting of halo, cyano, hydroxy, amino, (1-4C)alkyl, or (1-4C)alkoxy;

a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C) alkyl, or (1-4C)alkoxy;

a heterocyclyl-(1-2C)alkyl group wherein the heterocyclyl moiety is a 4, 5, or 6-membered heterocyclyl group comprising up to three heteroatoms selected from N, O or S and is optionally substituted with one to three substituents selected from the group consisting of halo, cyano, hydroxy, amino, (1-4C) alkyl, or (1-4C)alkoxy;

(b) a group of the sub-formula VI:

Q²-X⁵—Y²— (VI)

wherein:

Y² is a direct bond or —[CR¹⁹R²⁰]_y— wherein integer y is 1 or 2 and R¹⁹ and R²⁰ are independently selected from hydrogen or (1-2C)alkyl;

X⁵ is selected from —O— or —C(O)—; and

Q² is selected from a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C) alkoxy;

a heterocyclyl-(1-2C)alkyl group wherein the heterocyclyl moiety is a 4, 5, or 6-membered heterocyclyl group comprising up to three heteroatoms selected from N, O or S, and is optionally substituted with one to three substituents selected from the group consisting of halo, cyano, hydroxy, amino, (1-4C)alkyl, or (1-4C)alkoxy;

and, if said heterocyclic ring comprises a nitrogen atom then said nitrogen is optionally substituted by one or more substituent groups (for example 1, 2 or 3), which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl;

an aryl group which is optionally substituted with one to three substituents selected from the group consisting of halo, cyano, hydroxy, amino, (1-4C)alkyl, or (1-4C)alkoxy;

an aryl-(1-2C)alkyl wherein the aryl moiety is optionally substituted with one to three substituents selected from the group consisting of halo, cyano, hydroxy, amino, (1-4C)alkyl, or (1-4C)alkoxy;

a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C) alkoxy;

a heterocyclyl-(1-2C)alkyl group wherein the heterocyclyl moiety is a 4, 5, or 6-membered heterocyclyl group comprising up to three heteroatoms selected from N, O or S, and is optionally substituted with one to three substituents selected from the group consisting of halo, cyano, hydroxy, amino, (1-4C)alkyl, or (1-4C)alkoxy;

(b) a group of the formula VII:

R²³R²⁴N—[CR^m R^n]_h— (VII)

wherein integer h is 0, 1, or 2;

each R^m and R^n group present is hydrogen;

R²³ and R²⁴ are each independently selected from hydrogen or (1-4C)alkyl; or (c) a group of the formula VIII:

Q³-X⁶—Y³— (VIII)

wherein Y³ is a direct bond or —[CR²⁵R²⁶]_z— wherein z is 1 to 2 and R²⁵ and R²⁶ are independently selected from hydrogen or (1-2C)alkyl;

X⁶ is selected from —O— or —C(O)—, if Y³ is —[CR²³R²⁴]_z—, and if Y³ is a direct bond, X⁶ is selected from —S—, —SO—, —SO₂— or —C(O)—; and Q³ is selected from (1-4C)alkyl, (3-6C)cycloalkyl, (3-6C)cycloalkyl(1-2C)alkyl, a 4, 5, or 6-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C) alkyl, halo(1-4C)alkyl, and (1-4C)alkoxy;

a heterocyclyl-(1-2C)alkyl group wherein the heterocyclyl moiety is a 4, 5, or 6-membered heterocyclyl group comprising up to three heteroatoms selected from N, O or S, and is optionally substituted with halo, nitro, cyano, hydroxy, amino, (1-4C)alkyl, hydroxy(1-4C)alkyl, halo (1-4C)alkyl, and (1-4C)alkoxy;

and wherein any non-aromatic heterocyclyl group within a R^{1b} substituent group optionally bears 1 or 2 oxo substituents;

(15) R^{1b} is selected from:

(i) hydrogen, amino, (1-4C)alkyl; or (ii) a group of sub-formula II:

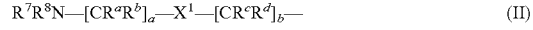

R⁷R⁸N—[CR^a R^b]_a—X¹—[CR^c R^d]_b— (II)

wherein:

X¹ is selected from a direct bond, or —O—;

integer a is 1, 2 or 3;

integer b is 0, 1 or 2;

each R^a, R^b, R^c and R^d group present is independently selected from hydrogen or (1-2C)alkyl;

R⁷ and R⁸ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;

a phenyl(1-2C)alkyl group, the phenyl moiety of which is unsubstituted or substituted with one to three substituents selected from the group consisting of halo, cyano, hydroxy, amino, (1-4C)alkyl, or (1-4C) alkoxy;

a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and wherein each heterocyclic group is unsubstituted or substituted with one to three substituents selected from the group consisting of halo, cyano, hydroxy, amino, (1-4C)alkyl, or (1-4C) alkoxy;

a heterocyclyl-(1-2C)alkyl group wherein the heterocyclyl moiety is carbon-linked to the alkyl group, and is either selected from the group consisting of a furanyl, tetrahydrofuranyl, pyranyl, tetrahydropyranyl, pyridinyl, pyrazinyl, thiazolyl, indolyl group, each of which is unsubstituted or substituted with one to three substituents selected from the group consisting of halo, cyano, hydroxy, amino, (1-4C)alkyl, halo(1-4C)

alkyl or (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

$$R^9R^{10}N-[CR^eR^f]_c-X^2-[CR^gR^h]_d- \quad \text{(III)}$$

wherein:

$X^2$ is selected from a direct bond, or —O—;

integer c is 1, 2 or 3;

integer d is 0, 1, or 2;

each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, (3-6C)cycloalkyl, (3-6C)cycloalkyl(1-2C)alkyl, or $R^9$ and $R^{10}$ are linked so that, together with the nitrogen atom to which they are attached, they form a 4,5-, or 6-membered non-aromatic heterocyclic ring, selected from the group consisting of azetidinyl, pyrrolidinyl, piperidinyl, piperazinyl, and morpholinyl, and wherein said heterocyclic ring is optionally substituted by hydroxy, halo, or (1-4C)alkyl;

or $R^7$ and $R^8$ are linked so that, together with the nitrogen atom to which they are attached, they form a 4 to 8-membered heterocyclic ring selected from the group consisting of azetidinyl, pyrrolidinyl, piperidinyl, piperazinyl, 3-azabicyclo[3.1.0]hexyl, hexahydropyrrolo[3,4-c]pyrrolyl, 7-azabicyclo[2.2.1]heptyl, and 2-azabicyclo[2.2.2]octyl, and wherein said heterocyclylic ring is optionally substituted on carbon by one to three substituents selected from:

(a) halo, cyano, hydroxy, trifluoromethyl, amino, (1-4C)alkyl, hydroxy(1-4C)alkyl, halo(1-4C)alkyl, N-[(1-4C)alkyl]amino, N,N-di-[(1-4C)alkyl]amino;

a phenyl group which is optionally substituted with one to three substituents selected from the group consisting of halo, cyano, hydroxy, amino, (1-4C)alkyl, or (1-4C)alkoxy;

a phenyl-(1-2C)alkyl wherein the phenyl moiety is optionally substituted with one to three substituents selected from the group consisting of halo, cyano, hydroxy, amino, (1-4C)alkyl, or (1-4C)alkoxy;

a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and which is unsubstituted or substituted with one to three substituents selected from the group consisting of halo, cyano, hydroxy, amino, (1-4C)alkyl, or (1-4C)alkoxy;

a heterocyclyl-(1-2C)alkyl group wherein the heterocyclyl moiety is selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and is optionally substituted with one to three substituents selected from the group consisting of halo, cyano, hydroxy, amino, (1-4C)alkyl, or (1-4C)alkoxy;

(b) a group of the sub-formula VI:

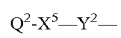
$$Q^2-X^5-Y^2- \quad \text{(VI)}$$

wherein:

$Y^2$ is a direct bond or $-[CR^{19}R^{20}]_y-$ wherein integer y is 1 or 2 and $R^{19}$ and $R^{20}$ are independently selected from hydrogen or (1-2C)alkyl;

$X^5$ is selected from —O— or —C(O)—; and $Q^2$ is selected from a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and which is unsubstituted or substituted with one to three substituents selected from the group consisting of halo, cyano, hydroxy, amino, (1-4C)alkyl, or (1-4C)alkoxy;

a heterocyclyl-(1-2C)alkyl group wherein the heterocyclyl moiety is selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and is optionally substituted with one to three substituents selected from the group consisting of halo, cyano, hydroxy, amino, (1-4C)alkyl, or (1-4C)alkoxy;

and, if said heterocyclic ring comprises a nitrogen atom then said nitrogen is optionally substituted by one or more substituent groups (for example 1, 2 or 3), which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl;

a phenyl group which is optionally substituted with one to three substituents selected from the group consisting of halo, cyano, hydroxy, amino, (1-4C)alkyl, or (1-4C)alkoxy;

a phenyl-(1-2C)alkyl wherein the aryl moiety is optionally substituted with one to three substituents selected from the group consisting of halo, cyano, hydroxy, amino, (1-4C)alkyl, or (1-4C)alkoxy;

a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, pyrazinyl, pyrimidinyl, imidazolyl, pyranyl, and pyridinyl, and wherein said heterocyclyl group is unsubstituted or substituted with one to three substituents selected from the group consisting of halo, cyano, hydroxy, amino, (1-4C)alkyl, or (1-4C)alkoxy;

a heterocyclyl-(1-2C)alkyl group wherein the heterocyclyl moiety is selected from azetidinyl, pyrrolidinyl, morpholinyl, tetrahydrofuranyl, furanyl, tetrahydropyranyl, piperidinyl, piperazinyl, pyrrolyl, pyrazolyl, pyrimidinyl, imidazolyl, pyranyl, and pyridinyl, and is optionally substituted with one to three substituents selected from the group consisting of halo, cyano, hydroxy, amino, (1-4C)alkyl, or (1-4C)alkoxy groups;

(b) a group of the formula VII:

$$R^{23}R^{24}N-[CR^mR^n]_h- \quad \text{(VII)}$$

wherein integer h is 0, 1, or 2;

each $R^m$ and $R^n$ group present is hydrogen;

$R^{23}$ and $R^{24}$ are each independently selected from hydrogen or (1-4C)alkyl; or (c) a group of the formula VIII:

$$Q^3-X^6-Y^3- \quad \text{(VIII)}$$

wherein Y³ is a direct bond or —[CR²⁵R²⁶]$_z$—
wherein z is 1 to 2 and R²⁵ and R²⁶ are independently selected from hydrogen or (1-2C)alkyl;

X⁶ is selected from —O— or —C(O)—, if Y³ is —[CR²³R²⁴]$_z$—, and if Y³ is a direct bond, X⁶ is selected from —SO₂— or —C(O)—; and Q³ is selected from (1-4C)alkyl, (3-6C)cycloalkyl,
a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, pyrimidinyl, imidazolyl, pyranyl, and pyridinyl, said heterocyclyl group being unsubstituted or substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

a heterocyclyl-(1-2C)alkyl group wherein the heterocyclyl moiety is selected from azetidinyl, pyrrolidinyl, morpholinyl, tetrahydrofuranyl, furanyl, tetrahydropyranyl, piperidinyl, piperazinyl, pyrrolyl, pyrazolyl, pyrimidinyl, imidazolyl, pyranyl, and pyridinyl, and is optionally substituted with one to three substituents selected from the group consisting of halo, nitro, cyano, hydroxy, amino, (1-4C)alkyl, hydroxy(1-4C)alkyl, halo(1-4C)alkyl, and (1-4C)alkoxy;

and wherein any non-aromatic heterocyclyl group within a R$^{1b}$ substituent group optionally bears 1 or 2 oxo substituents;

(16) R$^{1b}$ is selected from:
(i) hydrogen, amino, (1-4C)alkyl; or
(ii) a group of sub-formula II:

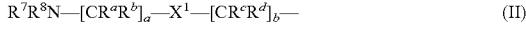

R⁷R⁸N—[CR$^a$R$^b$]$_a$—X¹—[CR$^c$R$^d$]$_b$— (II)

wherein:
X¹ is selected from a direct bond or —O—;
integer a is 1, or 2;
integer b is 0, 1, or 2;
each R$^a$, R$^b$, R$^c$ and R$^d$ group present is independently selected from hydrogen or (1-2C)alkyl;
R⁷ and R⁸ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;
a phenyl(1-2C)alkyl group, the phenyl moiety of which is unsubstituted or substituted with one to three substituents selected from the group consisting of halo, cyano, hydroxy, amino, (1-4C)alkyl, or (1-4C)alkoxy;
a 4, 5, or 6-membered heterocyclyl group selected from azetidinyl, pyrrolidinyl, morpholinyl, tetrahydrofuranyl, furanyl, tetrahydropyranyl, piperidinyl, piperazinyl, pyrrolyl, pyrazolyl, imidazolyl, pyranyl, and pyridinyl, and wherein each heterocyclic group is unsubstituted or substituted with one to three substituents selected from the group consisting of halo, cyano, hydroxy, amino, (1-4C)alkyl, or (1-4C)alkoxy;
a heterocyclyl-(1-2C)alkyl group wherein the heterocyclyl moiety is carbon-linked to the alkyl group and is either selected from the group consisting of a furanyl, tetrahydrofuranyl, tetrahydropyranyl, pyridinyl, pyrazinyl, thiazolyl, indolyl group, each of which is unsubstituted or substituted with one to three substituents selected from the group consisting of halo, cyano, hydroxy, amino, (1-4C)alkyl, halo(1-4C)alkyl or (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

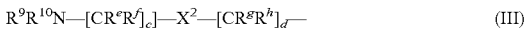

R⁹R¹⁰N—[CR$^e$R$^f$]$_c$—X²—[CR$^g$R$^h$]$_d$— (III)

wherein:
X² is selected from a direct bond;
integer c is 1, or 2;
integer d is 0, 1, or 2;
each R$^e$, R$^f$, R$^g$ and R$^h$ group present is independently selected from hydrogen or (1-2C)alkyl;
R⁹ and R¹⁰ are independently selected from hydrogen, (1-4C)alkyl, or R⁹ and R¹⁰ are linked so that, together with the nitrogen atom to which they are attached, they form a azetidinyl, pyrrolidinyl, piperidinyl, piperazinyl, or morpholinyl ring;
or R⁷ and R⁸ are linked so that, together with the nitrogen atom to which they are attached, they form a 4 to 8-membered heterocyclic ring selected from the group consisting of azetidinyl, pyrrolidinyl, piperidinyl, piperazinyl, 3-azabicyclo[3.1.0]hexyl, hexahydropyrrolo[3,4-c]pyrrolyl, 7-azabicyclo[2.2.1]heptyl, and 2-azabicyclo[2.2.2]octyl,
and wherein said heterocyclylic ring is optionally substituted on carbon by one to three substituents selected from:
(a) halo, cyano, hydroxy, trifluoromethyl, amino, (1-4C)alkyl, hydroxy(1-4C)alkyl, N-[(1-4C)alkyl]amino, N,N-di-[(1-4C)alkyl]amino;
a phenyl group which is optionally substituted with one or two substituents selected from the group consisting of halo, cyano, hydroxy, amino, (1-4C)alkyl, or (1-4C)alkoxy groups;
a pyrrolidinyl, morpholinyl, piperazinyl or pyridinyl ring, each of which is optionally substituted with one or two (1-4C)alkyl groups; or
(b) a group of the sub-formula VI:

Q²-X⁵—Y²— (VI)

wherein:
Y² is a direct bond or —[CR¹⁹R²⁰]$_y$— wherein integer y is 1 or 2 and R¹⁹ and R²⁰ are independently selected from hydrogen or (1-2C)alkyl;
X⁵ is selected from —C(O)—; and
Q² is morpholinyl;
and, if said heterocyclic ring comprises a nitrogen atom then said nitrogen is optionally substituted by one or more substituent groups (for example 1, 2 or 3), which may be the same or different, selected from:
(a) (1-4C)alkyl, hydroxy(1-4C)alkyl, (2-4C)alkenyl, (1-4C)alkanoyl, (1-4C)alkoxy-(1-4C)alkyl;
a phenyl group which is optionally substituted with one or two substituents selected from the group consisting of halo, cyano, hydroxy, amino, (1-4C)alkyl, or (1-4C)alkoxy;
a 4, 5, or 6-membered heterocyclyl group selected from pyrrolidinyl, piperidinyl, morpholinyl, piperazinyl, pyrazinyl, pyrimidinyl, and pyridinyl, and wherein said ring is unsubstituted or substituted with one or two substituents selected from the group consisting of halo, cyano, hydroxy, amino, (1-4C)alkyl, or (1-4C)alkoxy;
(b) a group of the formula VII:

R²³R²⁴N—[CR'''R'''']$_h$— (VII)

wherein integer h is 0, 1 or 2;

each $R^m$ and $R^n$ group present is hydrogen;

$R^{23}$ and $R^{24}$ are each independently selected from hydrogen or (1-4C)alkyl; or (c) a group of the formula VIII:

wherein $Y^3$ is a direct bond or —$[CR^{25}R^{26}]_z$— wherein z is 1 and $R^{25}$ and $R^{26}$ are both hydrogen;

$X^6$ is selected from —C(O)—, if $Y^3$ is —$[CR^{23}R^{24}]_z$—, and if $Y^3$ is a direct bond, $X^6$ is selected from —$SO_2$— or —C(O)—; and $Q^3$ is selected from (1-4C)alkyl, (3-6C)cycloalkyl or pyrrolidinyl, and wherein any non-aromatic heterocyclyl group within a $R^{1b}$ substituent group optionally bears 1 or 2 oxo substituents;

(17) $R^{1b}$ is selected from:

(i) hydrogen, amino, (1-4C)alkyl; or (ii) a group of sub-formula II:

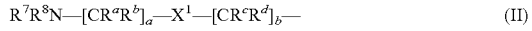

wherein:

$X^1$ is selected from a direct bond or —O—;

integer a is 1, or 2;

integer b is 0, 1, or 2;

each $R^a$, $R^b$, $R^c$ and $R^d$ group present is independently selected from hydrogen or (1-2C)alkyl;

$R^7$ and $R^8$ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;

a phenyl(1-2C)alkyl group, the phenyl moiety of which is optionally substituted with one or two (1-4C)alkoxy groups;

tetrahydropyranyl;

a heterocyclyl-(1-2C)alkyl group wherein the heterocyclyl moiety is carbon-linked to the alkyl group and is either selected from the group consisting of a furan-2-yl, tetrahydrofuran-2-yl, tetrahydropyran-4-yl, pyridin-2-yl, pyridin-3-yl, pyridin-4-yl, pyrazin-2-yl, thiazol-2-yl, and indol-3-yl, and wherein each of said heterocyclyl moieties is unsubstituted or substituted with one or two substituents selected from the group consisting of halo, (1-4C)alkyl, or halo(1-4C)alkyl, or the heterocyclyl moiety is selected from 1,3-dimethyl-1H-pyrazol-5-yl, 3,5-dimethyl-1H-pyrazol-4-yl, and 1-methyl-1H-imidazol-4-yl;

a group of sub-formula III:

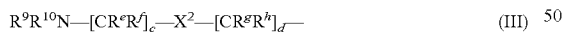

wherein:

$X^2$ is selected from a direct bond;

integer c is 1 or 2;

integer d is 0 or 1;

each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, or $R^9$ and $R^{10}$ are linked so that, together with the nitrogen atom to which they are attached, they form a pyrrolidinyl or piperidinyl ring;

or $R^7$ and $R^8$ are linked so that, together with the nitrogen atom to which they are attached, they form a 4 to 8-membered heterocyclic ring selected from the group consisting of azetidinyl, pyrrolidinyl, piperidinyl, piperazinyl, 3-azabicyclo[3.1.0]hexyl, hexahydropyrrolo[3,4-c]pyrrolyl, 7-azabicyclo[2.2.1]heptyl, and 2-azabicyclo[2.2.2]octyl, and wherein said heterocyclyic ring is optionally substituted on carbon by one or two substituents selected from:

(a) halo, hydroxy, trifluoromethyl, (1-4C)alkyl, hydroxy(1-4C)alkyl, N-[(1-4C)alkyl]amino, N,N-di-[(1-4C)alkyl]amino;

a phenyl group which is optionally substituted with one or two halo atoms;

a heterocyclyl group which is selected from pyrrolidinyl, morpholinyl, piperazinyl or pyridinyl, each of which is optionally substituted with one or two (1-4C)alkyl groups; or (b) a group of the sub-formula VI:

wherein:

$Y^2$ is a direct bond;

$X^5$ is selected from —C(O)—; and $Q^2$ is morpholinyl;

and, if said heterocyclic ring comprises a nitrogen atom then said nitrogen is optionally substituted by one or more substituent groups (for example 1, 2 or 3), which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl;

a phenyl group which is optionally substituted with one or two cyano groups;

a heterocyclyl group selected from pyrrolidinyl, pyrazinyl, pyrimidinyl and pyridinyl, and wherein said heterocyclyl group is unsubstituted or substituted with one or two cyano groups;

(b) a group of the formula VII:

wherein integer h is 0, 1 or 2;

each $R^m$ and $R^n$ group present is hydrogen;

$R^{23}$ and $R^{24}$ are each independently selected from hydrogen or (1-4C)alkyl; or (c) a group of the formula VIII:

wherein $Y^3$ is a direct bond or —$[CR^{25}R^{26}]_z$— wherein z is 1 and $R^{25}$ and $R^{26}$ are both hydrogen;

$X^6$ is —C(O)—, if $Y^3$ is —$[CR^{23}R^{24}]_z$—, and if $Y^3$ is a direct bond, $X^6$ is selected from —$SO_2$— or —C(O)—; and $Q^3$ is selected from (1-4C)alkyl, (3-6C)cycloalkyl or pyrrolidinyl, and wherein any non-aromatic heterocyclyl group within a $R^{1b}$ substituent group optionally bears 1 or 2 oxo substituents;

(18) $R^{1b}$ is selected from:

(i) hydrogen, amino, (1-4C)alkyl; or (ii) a group of sub-formula II:

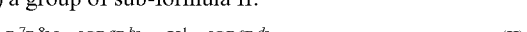

wherein:

$X^1$ is selected from a direct bond or —O—;

integer a is 1 or 2;

integer b is 0, 1 or 2;

each $R^a$, $R^b$, $R^c$ and $R^d$ group present is independently selected from hydrogen or (1-2C)alkyl;

$R^7$ and $R^8$ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;

a phenyl(1-2C)alkyl group, the phenyl moiety of which is optionally substituted with one or two (1-4C) alkoxy groups;

tetrahydropyranyl;

a heterocyclyl-(1-2C)alkyl group wherein the heterocyclyl moiety is carbon-linked to the alkyl group and is either selected from the group consisting of a furan-2-yl, tetrahydrofuran-2-yl, tetrahydropyran-4-yl, pyridin-3-yl, pyrazin-2-yl, thiazol-2-yl, indol-3-yl group, each of which is unsubstituted or substituted with one or two substituents selected from the group consisting of halo, (1-4C)alkyl or halo(1-4C)alkyl;

a group of sub-formula III:

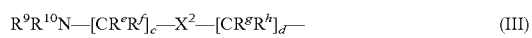

$$R^9R^{10}N-[CR^eR^f]_c-X^2-[CR^gR^h]_d- \quad (III)$$

wherein:

$X^2$ is selected from a direct bond;

integer c is 1, or 2;

integer d is 0, or 1;

each $R^e$, $R^f$, $R^g$ and $R^h$ group present is independently selected from hydrogen or (1-2C)alkyl;

$R^9$ and $R^{10}$ are independently selected from hydrogen, (1-4C)alkyl, or $R^9$ and $R^{10}$ are linked so that, together with the nitrogen atom to which they are attached, they form a pyrrolidinyl or piperidinyl ring;

or $R^7$ and $R^8$ are linked so that, together with the nitrogen atom to which they are attached, they form a 4 to 8-membered heterocyclic ring selected from the group consisting of azetidinyl, pyrrolidinyl, piperidinyl, piperazinyl, 3-azabicyclo[3.1.0]hexyl, hexahydropyrrolo[3,4-c]pyrrolyl, 7-azabicyclo[2.2.1]heptyl, and 2-azabicyclo[2.2.2]octyl, and wherein said heterocyclic ring is optionally substituted on carbon by one or two substituents selected from:

(a) halo, hydroxy, trifluoromethyl, (1-4C)alkyl, hydroxy(1-4C)alkyl, N-[(1-4C)alkyl]amino, N,N-di-[(1-4C)alkyl]amino;

a phenyl group which is optionally substituted with one or two halo atoms;

a pyrrolidinyl, morpholinyl, piperazinyl or pyridinyl, each of which is optionally substituted with one or two (1-4C)alkyl groups, (b) a group of the sub-formula VI:

$$Q^2-X^5-Y^2- \quad (VI)$$

wherein:

$Y^2$ is a direct bond;

$X^5$ is selected from —C(O)—; and $Q^2$ is morpholinyl;

and, if said hetero cyclic ring comprises a nitrogen atom then said nitrogen is optionally substituted by one or more substituent groups (for example 1, 2 or 3), which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl;

a phenyl group which is optionally substituted with one or two cyano groups;

a heterocyclyl group selected from pyrrolidinyl, pyrazinyl, pyrimidinyl and pyridinyl, and wherein said heterocyclyl group is unsubstituted or substituted with one or two cyano groups;

(b) a group of the formula VII:

$$R^{23}R^{24}N-[CR^mR^n]_h- \quad (VII)$$

wherein integer h is 0, 1, or 2;

each $R^m$ and $R^n$ group present is hydrogen;

$R^{23}$ and $R^{24}$ are each independently selected from hydrogen or (1-4C)alkyl; or (c) a group of the formula VIII:

$$Q^3-X^6-Y^3- \quad (VIII)$$

wherein $Y^3$ is a direct bond or —$[CR^{25}R^{26}]_z$— wherein z is 1 and $R^{25}$ and $R^{26}$ are both hydrogen;

$X^6$ is —C(O)—, if $Y^3$ is —$[CR^{23}R^{24}]_z$—, and if $Y^3$ is a direct bond, $X^6$ is selected from —SO$_2$— or —C(O)—; and $Q^3$ is selected from (1-4C)alkyl, (3-6C)cycloalkyl or pyrrolidinyl, and wherein any non-aromatic heterocyclyl group within a $R^{1b}$ substituent group optionally bears 1 or 2 oxo substituents;

(19) $R^{1b}$ is selected from hydrogen, cyano, amino, methyl, hydroxymethyl, 1-hydroxyethyl, (methylamino)methyl, (ethylamino)methyl, 1-(ethylamino)ethyl, (propylamino)methyl, (isopropylamino)methyl, (cyclopropylamino)methyl, (butylamino)methyl, (cyclobutylamino)methyl, (cyclopentylamino)methyl, (1-methylpropylamino)methyl, (2-methylpropylamino)methyl, (allylamino)methyl, (diethylamino)methyl, [(ethyl)(methyl)amino]methyl, [(isopropyl)(methyl)amino]methyl, [(propyl)(methyl)amino]methyl, [(butyl)(methyl)amino]methyl, [(cyclopropylmethyl)amino]methyl, [(cyclobutylmethyl)(methyl)amino]methyl, [(2-methoxyethyl)(methyl)amino]methyl, [(isopropyl)(2-methoxyethyl)amino]methyl, [(2-methoxyethyl)amino]methyl, [(ethyl)(2-methoxyethyl)amino]methyl, [(2-methoxy-1-methylethyl)amino]methyl, [(3-methoxypropyl)amino]methyl, [(3-isopropoxypropyl)amino]methyl, [(2-ethoxyethyl)amino]methyl, [(2-isopropoxyethyl)amino]methyl, [(3-ethoxypropyl)amino]methyl, [(2-propoxyethyl)amino]methyl, [(2-methoxy-2-methylpropyl)amino]methyl, [bis(2-methoxyethyl)amino]methyl, [(2-hydroxyethyl)(ethyl)amino]methyl, [(2-hydroxyethyl)(methyl)amino]methyl, {[2-(di-methylamino)ethyl]amino}methyl, {[2-(di-ethylamino)ethyl]amino}methyl, {[2-(di-methylamino)ethyl][methyl]amino}methyl, {[2-(di-ethylamino)ethyl][methyl]amino}methyl, {[2-(di-methylamino)-1-(methyl)ethyl]amino}methyl, azetidinylmethyl, pyrrolidinylmethyl, piperidinylmethyl, 1-piperidinylethyl, piperazinylmethyl, 7-azabicyclo[2.2.1]heptylmethyl, 2-azabicyclo[2.2.2]octylmethyl, {[2-(pyrrolidin-1-yl)ethyl]amino}methyl, {[2-(piperidin-1-yl)ethyl]amino}methyl, (3-fluoropyrrolidin-1-yl)methyl, (4-fluoropiperidin-1-yl)methyl, (3-hydroxypyrrolidin-1-yl)methyl, (3-hydroxypiperidin-1-yl)methyl, (4-hydroxypiperidin-1-yl)methyl, (4-trifluoromethylpiperidin-1-yl)methyl, [2,5-dimethylpyrrolidin-1-yl]methyl, (4-methylpiperidin-1-yl)methyl, (4-hydroxymethylpiperidin-1-yl)methyl, (3,3-dimethylpiperidin-1-yl)methyl, [6-(hydroxymethyl)-3-azabicyclo[3.1.0]hex-3-yl]methyl, (3-methylaminopyrrolidin-1-yl)methyl, [3-(dimethylamino)pyrrolidin-1-yl]methyl, [3-(diethylamino)pyrrolidin-1-yl]methyl, (3-phenylpyrrolidin-1-yl)methyl, (3-phenylpiperidin-1-yl)methyl, (4-phenylpiperidin-1-yl)methyl, [3-(4-fluorophenyl)piperidin-1-yl]methyl, (3-pyridin-2-ylpyrrolidin-1-yl)methyl, (4-morpholin-4-ylpiperidin-1-yl)methyl, [4-(2-oxopyrrolidin-1-yl)piperidin-1-yl]methyl, (4-pyrrolidin-1-ylpiperidin-1-yl)methyl, (4-pyridin-4-ylpiperidin-1-yl)methyl, [(4-methylpiperazin-1-yl)piperidin-1-yl]methyl, [4-(morpholin-4-ylcarbonyl)piperidin-1-yl]methyl, (4-methylpiperazin-1-yl)methyl, (4-ethylpiperazin-1-yl)methyl, [4-(2-hydroxyethyl)piperazin-1-yl]methyl, (4-isopropylpiperazin-1-yl)methyl, {4-[2-(dimethylamino)

ethyl]piperazin-1-yl}methyl, (4-allylpiperazin-1-yl)methyl, (4-acetylpiperazin-1-yl)methyl, (5-butyrylhexahydropyrrolo[3,4-c]pyrrol-2(1H)-yl)methyl, [4-(2-methoxyethyl)piperazin-1-yl]methyl, [4-(methylsulfonyl)piperazin-1-yl]methyl, [4-(ethylsulfonyl)piperazin-1-yl]methyl, [4-(2-cyanophenyl)piperazin-1-yl]methyl, [4-(pyridin-2-yl)piperazin-1-yl]methyl, [4-(3-cyanopyridin-2-yl)piperazin-1-yl]methyl, [4-(3-cyanopyrazin-2-yl)piperazin-1-yl]methyl, (4-pyrimidin-2-ylpiperazin-1-yl)methyl, (4-pyrazin-2-ylpiperazin-1-yl)methyl, [4-(2-oxo-2-pyrrolidin-1-ylethyl)piperazin-1-yl]methyl, [4-(cyclopropylcarbonyl)piperazin-1-yl]methyl, {[(1,3-dimethyl-1H-pyrazol-5-yl)methyl]amino}methyl, {[2-(3,5-dimethyl-1H-pyrazol-4-yl)ethyl]amino}methyl, [methyl(tetrahydrofuran-2-ylmethyl)amino]methyl, [(5-methylpyrazin-2-yl)methyl]amino}methyl, [6-(trifluoromethyl)pyridin-3-yl]methyl}amino)methyl, [(4-methyl-1,3-thiazol-2-yl)methyl]amino}methyl, [2-(1-methyl-1H-imidazol-4-yl)ethyl]amino}methyl, [(tetrahydrofuran-2-ylmethyl)amino]methyl, [(5-methyl-2-furyl)methyl]amino}methyl, (tetrahydro-2H-pyran-4-ylmethyl)amino]methyl, (tetrahydro-2H-pyran-4-ylamino)methyl, {[2-(2-methyl-1H-indol-3-yl)ethyl]amino}methyl, (2-methoxybenzyl)amino]methyl, [(3-methoxybenzyl)amino]methyl, {[2-(isopropylamino)ethoxy]methyl, [2-(ethylamino)ethoxy]methyl, and [2-(methylamino)ethoxy]methyl;

(20) $R^{1b}$ is selected from hydrogen, amino, methyl, azetidinylmethyl, pyrrolidinylmethyl, piperidinylmethyl, 1-piperidinylethyl, piperazinylmethyl, 7-azabicyclo[2.2.1]heptylmethyl, 2-azabicyclo[2.2.2]octylmethyl, (3-fluoropyrrolidin-1-yl)methyl, (4-hydroxypiperidin-1-yl)methyl, (4-trifluoromethylpiperidin-1-yl)methyl, [2,5-dimethylpyrrolidin-1-yl]methyl, (4-methylpiperidin-1-yl)methyl, (4-hydroxymethylpiperidin-1-yl)methyl, (3,3-dimethylpiperidin-1-yl)methyl, (3-methylaminopyrrolidin-1-yl)methyl, [3-(dimethylamino)pyrrolidin-1-yl]methyl, (3-phenylpyrrolidin-1-yl)methyl, (3-phenylpiperidin-1-yl)methyl, (4-phenylpiperidin-1-yl)methyl, [3-(4-fluorophenyl)piperidin-1-yl]methyl, (3-pyridin-2-ylpyrrolidin-1-yl)methyl, (4-morpholin-4-ylpiperidin-1-yl)methyl, [4-(2-oxopyrrolidin-1-yl)piperidin-1-yl]methyl, (4-pyrrolidin-1-ylpiperidin-1-yl)methyl, (4-pyridin-4-ylpiperidin-1-yl)methyl, [(4-methylpiperazin-1-yl)piperidin-1-yl]methyl, (4-methylpiperazin-1-yl)methyl, (4-ethylpiperazin-1-yl)methyl, [4-(2-hydroxyethyl)piperazin-1-yl]methyl, (4-isopropylpiperazin-1-yl)methyl, {4-[2-(dimethylamino)ethyl]piperazin-1-yl}methyl, (4-allylpiperazin-1-yl)methyl, (4-acetylpiperazin-1-yl)methyl, (5-butyrylhexahydropyrrolo[3,4-c]pyrrol-2(1H)-yl)methyl, [4-(2-methoxyethyl)piperazin-1-yl]methyl, [4-(methylsulfonyl)piperazin-1-yl]methyl, [4-(ethylsulfonyl)piperazin-1-yl]methyl, [4-(2-cyanophenyl)piperazin-1-yl]methyl, [4-(pyridin-2-yl)piperazin-1-yl]methyl, [4-(3-cyanopyridin-2-yl)piperazin-1-yl]methyl, [4-(3-cyanopyrazin-2-yl)piperazin-1-yl]methyl, (4-pyrimidin-2-ylpiperazin-1-yl)methyl, (4-pyrazin-2-ylpiperazin-1-yl)methyl, {[2-(2-methyl-1H-indol-3-yl)ethyl]amino}methyl, (methylamino)methyl, (ethylamino)methyl, 1-(ethylamino)ethyl, (propylamino)methyl, (isopropylamino)methyl, (cyclopropylamino)methyl, (butylamino)methyl, (cyclobutylamino)methyl, (cyclopentylamino)methyl, (1-methylpropylamino)methyl, (2-methylpropylamino)methyl, (allylamino)methyl, (di-ethylamino)methyl, [(ethyl)(methyl)amino]methyl, [(isopropyl)(methyl)amino]methyl, [(propyl)(methyl)amino]methyl, [(cyclopropylmethyl)amino]methyl, [(cyclobutylmethyl)(methyl)amino]methyl, [(2-methoxyethyl)(methyl)amino]methyl, [(isopropyl)(2-methoxyethyl)amino]methyl, [(2-methoxyethyl)amino]methyl, [(ethyl)(2-methoxyethyl)amino]methyl, {[2-(di-methylamino)ethyl]amino}methyl, {[2-(di-ethylamino)ethyl]amino}methyl, {[2-(di-methylamino)ethyl][methyl]amino}methyl, {[2-(di-ethylamino)ethyl][methyl]amino}methyl, {[2-(di-methylamino)-1-(methyl)ethyl]amino}methyl, [(1-methylpropyl)amino]methyl, {[2-(pyrrolidin-1-yl)ethyl]amino}methyl, {[2-(piperidin-1-yl)ethyl]amino}methyl, {[2-(isopropylamino)ethoxy]methyl, and [2-(ethylamino)ethoxy]methyl, [(butyl)(methyl)amino]methyl, [(2-methoxy-1-methylethyl)amino]methyl, [(3-methoxypropyl)amino]methyl, [(3-isopropoxypropyl)amino]methyl, [(2-ethoxyethyl)amino]methyl, [(2-isopropoxyethyl)amino]methyl, [(3-ethoxypropyl)amino]methyl, [(2-propoxyethyl)amino]methyl, [(2-methoxy-2-s methylpropyl)amino]methyl, [bis(2-methoxyethyl)amino]methyl, (2-methoxybenzyl)amino]methyl, [(3-methoxybenzyl)amino]methyl, [methyl(tetrahydrofuran-2-ylmethyl)amino]methyl, [(tetrahydrofuran-2-ylmethyl)amino]methyl, [(5-methyl-2-furyl)methyl]amino}methyl, (tetrahydro-2H-pyran-4-ylmethyl)amino]methyl, (tetrahydro-2H-pyran-4-ylamino)methyl, or [3-(diethylamino)pyrrolidin-1-yl]methyl.

(21) $R^{1c}$ is selected from hydrogen, amino, (1-3C)alkyl, N-(1-3C)alkylamino, and N,N-di-[(1-3C)alkyl]amino;

(22) $R^{1c}$ is selected from hydrogen, (1-3C)alkyl and N,N-di-[(1-3C)alkyl]amino;

(23) $R^{1c}$ is selected from hydrogen, (1-2C)alkyl and N,N-di-[(1-2C)alkyl]amino;

(24) $R^{1c}$ is selected from hydrogen, methyl and di-methylamino;

(25) $R^{1c}$ is di-methylamino;

(26) $R^{1c}$ is hydrogen;

(27) m is 0;

(28) n is 0;

(29) $R^4$ is amino.

A particularly preferred group of compounds of the invention have the general structural formula VIII below:

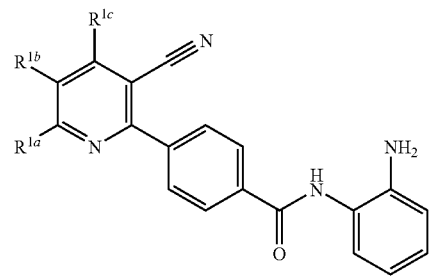

VIII wherein $R^{1a}$, $R^{1b}$ and $R^{1c}$ have any one of the definitions set out herein, with the proviso that at least one of $R^{1a}$, $R^{1b}$ and $R^{1c}$ is hydrogen.

In the compounds of formula VIII above, $R^{1a}$ is suitably as defined in any one of paragraphs (1) to (9) above, and is particularly as defined in any one of paragraphs (4) to (9) above. $R^{1b}$ is suitably as defined in any one of paragraphs (10) to (20) above, and is particularly as defined in any one of paragraphs (16) to (20) above. $R^{1c}$ is suitably as defined in any one of paragraphs (21) to (26) above, and is particularly as defined in any one of paragraphs (24) to (26) above.

A further particular sub group of preferred compounds of the present invention has the general formula IX shown below:

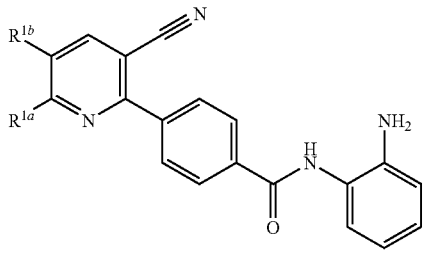

IX wherein $R^{1a}$ and $R^{1b}$ have any one of the definitions set out hereinbefore.

In the compounds of formula IX above, $R^{1a}$ is suitably as defined in any one of paragraphs (1) to (9) above. In particular, $R^{1a}$ is hydrogen or (1-3C)alkyl, especially hydrogen or methyl. $R^{1b}$ is suitably as defined in any one of paragraphs (10) to (20) above, and is particularly as defined in any one of paragraphs (16) to (20) above.

A further particular group of preferred compounds has the general formula X shown below:

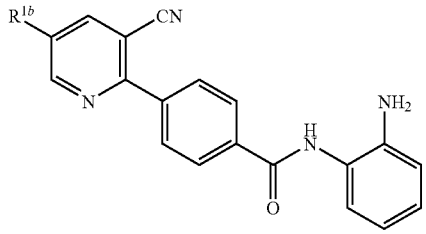

X wherein $R^{1b}$ is as hereinbefore defined.

Suitably $R^{1b}$ is as defined in any one of paragraphs (10) to (20) above, and is particularly as defined in any one of paragraphs (16) to (20) above.

Suitably $R^{1b}$ is a group of sub-formula II as defined in any one of paragraphs (10) to (18) above, and especially as defined in paragraphs (16) and (18) above.

A particular sub-group of compounds of formula X above has the general formula XI shown below

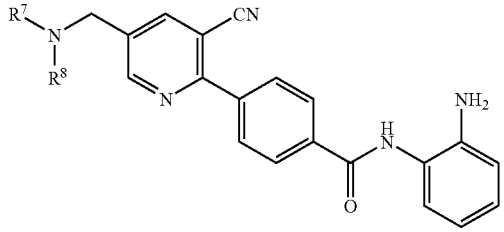

XI wherein $R^7$ and $R^8$ have any one of the definitions set out herein.

Suitably, $R^7$ and $R^8$ are as defined in anyone of paragraphs (10) to (18) above, and are particularly as defined in paragraphs (16) and (18) above.

A further particular sub-group of compounds of formula (X) above has the general formula (XII) shown below

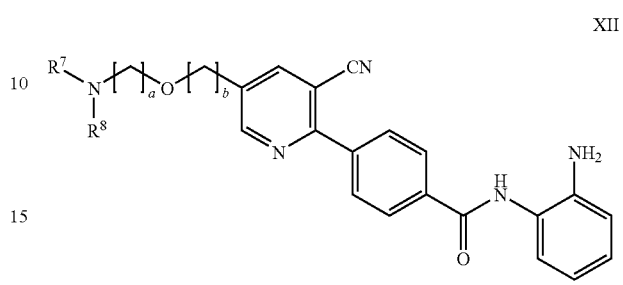

XII wherein $R^7$, $R^8$, integer a and integer b have any one of the definitions set out hereinbefore.

In the compounds of formula XII above, $R^7$ and $R^8$ are as defined in anyone of paragraphs (10) to (18) above. Suitably, $R^7$ and $R^8$ are selected from hydrogen or (1-6C)alkyl, and especially hydrogen or (1-4C)alkyl.

Integer a is preferably 1 or 2.

Integer b is preferably 1 or 2.

In a further preferred group of compounds formula (I), m is 0, n is 0, $R^4$ is amino, $R^{1b}$ is hydrogen, $R^{1c}$ is hydrogen and $R^{1a}$ has any one of the definitions set out herein (and, in particular, is as defined in any one of paragraphs (1) to (9) above).

In a further preferred group of compounds formula (I), m is 0, n is 0, $R^4$ is amino, $R^{1b}$ is hydrogen, $R^{1a}$ is selected from hydrogen or (1-3C)alkyl and $R^{1c}$ has any one of the definitions set out herein (and, in particular, is as defined in any one of paragraphs (21) to (26) above).

Particular novel compounds of the invention include any one of the following:

N-(2-aminophenyl)-4-(3-cyanopyridin-2-yl)benzamide;

N-(2-aminophenyl)-4-{3-cyano-6-[(2-hydroxyethyl) amino]-4-methylpyridin-2-yl}benzamide;

N-(2-aminophenyl)-4-[3-cyano-5-(piperidin-1-ylmethyl)pyridin-2-yl]benzamide;

N-(2-aminophenyl)-4-{3-cyano-5-[(4-methylpiperidin-1-yl)methyl]pyridin-2-yl}benzamide;

N-(2-aminophenyl)-4-{3-cyano-5-[(diethylamino)methyl] pyridin-2-yl}benzamide;

N-(2-aminophenyl)-4-[3-cyano-4-methyl-6-(4-methylpiperazin-1-yl)pyridin-2-yl]benzamide;

N-(2-aminophenyl)-4-[3-cyano-5-(pyrrolidin-1-ylmethyl) pyridin-2-yl]benzamide;

N-(2-aminophenyl)-4-{3-cyano-5-[(3-phenylpyrrolidin-1-yl)methyl]pyridin-2-yl}benzamide;

N-(2-aminophenyl)-4-{3-cyano-5-[(4-isopropylpiperazin-1-yl)methyl]pyridin-2-yl}benzamide;

N-(2-aminophenyl)-4-[3-cyano-5-(piperazin-1-ylmethyl) pyridin-2-yl]benzamide;

N-(2-aminophenyl)-4-{3-cyano-5-[(4-methylpiperazin-1-yl)methyl]pyridin-2-yl}benzamide;

N-(2-aminophenyl)-4-{3-cyano-5-[(4-ethylpiperazin-1-yl) methyl]pyridin-2-yl}benzamide;

N-(2-aminophenyl)-4-{3-cyano-5-[(3-pyridin-2-ylpyrrolidin-1-yl)methyl]pyridin-2-yl}benzamide;

N-(2-aminophenyl)-4-(3-cyano-5-{[(2R,5R)-2,5-dimethylpyrrolidin-1-yl]methyl}pyridin-2-yl)benzamide;

N-(2-aminophenyl)-4-{3-cyano-5-[(4-hydroxypiperidin-1-yl)methyl]pyridin-2-yl}benzamide;

N-(2-aminophenyl)-4-(3-cyano-5-{[4-(trifluoromethyl)piperidin-1-yl]methyl}pyridin-2-yl)benzamide;

N-(2-aminophenyl)-4-{3-cyano-5-[(4-morpholin-4-ylpiperidin-1-yl)methyl]pyridin-2-yl}benzamide;

N-(2-aminophenyl)-4-{3-cyano-5-[(3,3-dimethylpiperidin-1-yl)methyl]pyridin-2-yl}benzamide;

N-(2-aminophenyl)-4-[5-(azetidin-1-ylmethyl)-3-cyanopyridin-2-yl]benzamide;

N-(2-aminophenyl)-4-(3-cyano-5-{[4-(2-oxopyrrolidin-1-yl)piperidin-1-yl]methyl}pyridin-2-yl)benzamide;

N-(2-aminophenyl)-4-{3-cyano-5-[(4-pyrrolidin-1-ylpiperidin-1-yl)methyl]pyridin-2-yl}benzamide;

N-(2-aminophenyl)-4-(3-cyano-5-{[(cyclobutylmethyl)(methyl)amino]methyl}pyridin-2-yl)benzamide;

N-(2-aminophenyl)-4-(3-cyano-5-{[(2-methoxyethyl)(methyl)amino]methyl}pyridin-2-yl)benzamide;

N-(2-aminophenyl)-4-(3-cyano-5-{[(3S)-3-(dimethylamino)pyrrolidin-1-yl]methyl}pyridin-2-yl)benzamide;

N-(2-aminophenyl)-4-(3-cyano-5-{[(isopropyl)(2-methoxyethyl)amino]methyl}pyridin-2-yl)benzamide;

N-(2-aminophenyl)-4-{3-cyano-5-[(4-pyridin-4-ylpiperidin-1-yl)methyl]pyridin-2-yl}benzamide;

N-(2-aminophenyl)-4-[5-(7-azabicyclo[2.2.1]hept-7-ylmethyl)-3-cyanopyridin-2-yl]benzamide;

N-(2-aminophenyl)-4-(3-cyano-5-{[(cyclopropylmethyl)amino]methyl}pyridin-2-yl)benzamide;

N-(2-aminophenyl)-4-[5-(2-azabicyclo[2.2.2]oct-2-ylmethyl)-3-cyanopyridin-2-yl]benzamide;

N-(2-aminophenyl)-4-[3-cyano-6-methyl-5-(1-piperidin-1-ylethyl)pyridin-2-yl]benzamide;

N-(2-aminophenyl)-4-(3-cyano-5-{[4-(4-methylpiperazin-1-yl)piperidin-1-yl]methyl}pyridin-2-yl)benzamide;

N-(2-aminophenyl)-4-(3-cyano-5-{[isopropyl(methyl)amino]methyl}pyridin-2-yl)benzamide;

N-(2-aminophenyl)-4-(3-cyano-5-{[ethyl(2-methoxyethyl)amino]methyl}pyridin-2-yl)benzamide;

N-(2-aminophenyl)-4-(3-cyano-5-{[methyl(propyl)amino]methyl}pyridin-2-yl)benzamide;

4-{5-[(4-allylpiperazin-1-yl)methyl]-3-cyanopyridin-2-yl}-N-(2-aminophenyl)benzamide;

N-(2-aminophenyl)-4-(3-cyano-5-{[4-(2-methoxyethyl)piperazin-1-yl]methyl}pyridin-2-yl)benzamide;

N-(2-aminophenyl)-4-[3-cyano-5-({[2-(dimethylamino)ethyl]amino}methyl)pyridin-2-yl]benzamide;

N-(2-aminophenyl)-4-[3-cyano-5-({[2-(diethylamino)ethyl]amino}methyl)pyridin-2-yl]benzamide;

N-(2-aminophenyl)-4-(3-cyano-5-{[(2-pyrrolidin-1-ylethyl)amino]methyl}pyridin-2-yl)benzamide;

N-(2-aminophenyl)-4-(3-cyano-5-{[(2-piperidin-1-ylethyl)amino]methyl}pyridin-2-yl)benzamide;

N-(2-aminophenyl)-4-(3-cyano-5-{[4-(3-cyanopyridin-2-yl)piperazin-1-yl]methyl}pyridin-2-yl)benzamide;

N-(2-aminophenyl)-4-[3-cyano-5-({4-[2-(dimethylamino)ethyl]piperazin-1-yl}methyl)pyridin-2-yl]benzamide;

N-(2-aminophenyl)-4-{3-cyano-5-[(4-pyridin-2-ylpiperazin-1-yl)methyl]pyridin-2-yl}benzamide;

N-(2-aminophenyl)-4-(3-cyano-5-{[[2-(dimethylamino)ethyl](methyl)amino]methyl}pyridin-2-yl)benzamide;

N-(2-aminophenyl)-4-(3-cyano-5-{[[2-(diethylamino)ethyl](methyl)amino]methyl}pyridin-2-yl)benzamide;

N-(2-aminophenyl)-4-{3-cyano-5-[(propylamino)methyl]pyridin-2-yl}benzamide;

N-(2-aminophenyl)-4-{5-[(butylamino)methyl]-3-cyanopyridin-2-yl}benzamide;

N-(2-aminophenyl)-4-{5-[(sec-butylamino)methyl]-3-cyanopyridin-2-yl}benzamide;

N-(2-aminophenyl)-4-{3-cyano-5-[(cyclobutylamino)methyl]pyridin-2-yl}benzamide;

N-(2-aminophenyl)-4-{3-cyano-5-[(isopropylamino)methyl]pyridin-2-yl}benzamide;

N-(2-aminophenyl)-4-{3-cyano-5-[(isobutylamino)methyl]pyridin-2-yl}benzamide;

4-{5-[(allylamino)methyl]-3-cyanopyridin-2-yl}-N-(2-aminophenyl)benzamide;

N-(2-aminophenyl)-4-{3-cyano-5-[(cyclopentylamino)methyl]pyridin-2-yl}benzamide;

N-(2-aminophenyl)-4-{3-cyano-5-[(ethylamino)methyl]pyridin-2-yl}benzamide;

N-(2-aminophenyl)-4-{3-cyano-5-[(4-pyrazin-2-ylpiperazin-1-yl)methyl]pyridin-2-yl}benzamide;

N-(2-aminophenyl)-4-[3-cyano-5-({[2-(dimethylamino)-1-methylethyl]amino}methyl)pyridin-2-yl]benzamide;

N-(2-aminophenyl)-4-(3-cyano-5-{[3-(methylamino)pyrrolidin-1-yl]methyl}pyridin-2-yl)benzamide;

N-(2-aminophenyl)-4-(3-cyano-5-{[4-(2-cyanophenyl)piperazin-1-yl]methyl}pyridin-2-yl)benzamide;

N-(2-aminophenyl)-4-(3-cyano-5-{[4-(3-cyanopyrazin-2-yl)piperazin-1-yl]methyl}pyridin-2-yl)benzamide;

N-(2-aminophenyl)-4-{3-cyano-5-[1-(ethylamino)ethyl]-6-methylpyridin-2-yl}benzamide;

N-(2-aminophenyl)-4-{3-cyano-5-[(methylamino)methyl]pyridin-2-yl}benzamide;

N-(2-aminophenyl)-4-(3-cyano-5-{[(3R)-3-hydroxypyrrolidin-1-yl]methyl}pyridin-2-yl)benzamide;

N-(2-aminophenyl)-4-(3-cyano-5-{[(3R)-3-fluoropyrrolidin-1-yl]methyl}pyridin-2-yl)benzamide;

N-(2-aminophenyl)-4-(3-cyano-5-{[(2-hydroxyethyl)(methyl)amino]methyl}pyridin-2-yl)benzamide;

N-(2-aminophenyl)-4-(3-cyano-5-{[4-(ethylsulfonyl)piperazin-1-yl]methyl}pyridin-2-yl)benzamide;

N-(2-aminophenyl)-4-{3-cyano-5-[(4-pyrimidin-2-ylpiperazin-1-yl)methyl]pyridin-2-yl}benzamide;

4-(5-amino-3-cyano-6-methylpyridin-2-yl)-N-(2-aminophenyl)benzamide;

N-(2-aminophenyl)-4-[3-cyano-5-({[(1R)-1-methylpropyl]amino}methyl)pyridin-2-yl]benzamide;

N-(2-aminophenyl)-4-[3-cyano-5-({[(1S)-1-methylpropyl]amino}methyl)pyridin-2-yl]benzamide;

N-(2-aminophenyl)-4-(3-cyano-5-{[4-(methylsulfonyl)piperazin-1-yl]methyl}pyridin-2-yl)benzamide;

N-(2-aminophenyl)-4-[3-cyano-5-({[2-(2-methyl-1H-indol-3-yl)ethyl]amino}methyl)pyridin-2-yl]benzamide;

N-(2-aminophenyl)-4-(3-cyano-5-{[2-(isopropylamino)ethoxy]methyl}pyridin-2-yl)benzamide;

N-(2-aminophenyl)-4-(3-cyano-5-{[2-(ethylamino)ethoxy]methyl}pyridin-2-yl)benzamide;

N-(2-aminophenyl)-4-(3-cyano-5-{[2-(methylamino)ethoxy]methyl}pyridin-2-yl)benzamide;

N-(2-aminophenyl)-4-(3-cyano-5-methylpyridin-2-yl)benzamide;

N-(2-aminophenyl)-4-[3-cyano-4-(dimethylamino)pyridin-2-yl]benzamide;

N-(2-aminophenyl)-4-[3-cyano-6-(ethylamino)-4-methylpyridin-2-yl]benzamide;

N-(2-aminophenyl)-4-(3-cyano-4,6-dimethylpyridin-2-yl)benzamide;

N-(2-aminophenyl)-4-(3-cyano-6-methylpyridin-2-yl)benzamide;

N-(2-aminophenyl)-4-(3-cyano-5-{[4-(2-oxo-2-pyrrolidin-1-ylethyl)piperazin-1-yl]methyl}pyridin-2-yl)benzamide;

N-(2-aminophenyl)-4-(3-cyano-5-{[4-(2-hydroxyethyl)piperazin-1-yl]methyl}pyridin-2-yl)benzamide;
N-(2-aminophenyl)-4-(3-cyano-5-{[(1R,5S)-6-(hydroxymethyl)-3-azabicyclo[3.1.0]hex-3-yl]methyl}pyridin-2-yl)benzamide;
N-(2-aminophenyl)-4-{3-cyano-5-[(4-hydroxymethylpiperidin-1-yl)methyl]pyridin-2-yl}benzamide;
4-{5-[(4-acetylpiperazin-1-yl)methyl]-3-cyanopyridin-2-yl}-N-(2-aminophenyl)benzamide;
N-(2-aminophenyl)-4-{3-cyano-5-[(3-hydroxypiperidin-1-yl)methyl]pyridin-2-yl}benzamide;
N-(2-aminophenyl)-4-{5-[(5-butyrylhexahydropyrrolo[3,4-c]pyrrol-2(1H)-yl)methyl]-3-cyanopyridin-2-yl}benzamide;
N-(2-aminophenyl)-4-(3-cyano-5-{[(2-hydroxyethyl)(ethyl)amino]methyl}pyridin-2-yl)benzamide;
N-(2-aminophenyl)-4-(3-cyano-5-{[(2-methoxyethyl)amino]methyl}pyridin-2-yl)benzamide;
N-(2-aminophenyl)-4-(3-cyano-5-{[ethyl(methyl)amino]methyl}pyridin-2-yl)benzamide;
N-(2-aminophenyl)-4-{3-cyano-5-[(3-phenylpiperidin-1-yl)methyl]pyridin-2-yl}benzamide;
N-(2-aminophenyl)-4-{3-cyano-5-[(4-phenylpiperidin-1-yl)methyl]pyridin-2-yl}benzamide;
N-(2-aminophenyl)-4-(3-cyano-5-{[3-(4-fluorophenyl)piperidin-1-yl]methyl}pyridin-2-yl)benzamide;
N-(2-aminophenyl)-4-(3-cyano-5-{[4-(morpholin-4-ylcarbonyl)piperidin-1-yl]methyl}pyridin-2-yl)benzamide;
N-(2-aminophenyl)-4-(3-cyano-5-{[3-(diethylamino)pyrrolidin-1-yl]methyl}pyridin-2-yl)benzamide;
N-(2-aminophenyl)-4-(5-{[butyl(methyl)amino]methyl}-3-cyanopyridin-2-yl)benzamide;
N-(2-aminophenyl)-4-(3-cyano-6-nitropyridin-2-yl)benzamide;
N-(2-aminophenyl)-4-[3-cyano-6-(4-fluorophenyl)pyridin-2-yl]benzamide;
4-(6-amino-3,5-dicyanopyridin-2-yl)-N-(2-aminophenyl)benzamide;
N-(2-aminophenyl)-4-(3-cyano-5-{[4-(cyclopropylcarbonyl)piperazin-1-yl]methyl}pyridin-2-yl)benzamide;
N-(2-aminophenyl)-4-{3-cyano-5-[(methylamino)methyl]pyridin-2-yl}benzamide;
N-(2-aminophenyl)-4-[3-cyano-5-({[(1,3-dimethyl-1H-pyrazol-5-yl)methyl]amino}methyl)pyridin-2-yl]benzamide;
N-(2-aminophenyl)-4-[3-cyano-5-({[2-(3,5-dimethyl-1H-pyrazol-4-yl)ethyl]amino}methyl)pyridin-2-yl]benzamide;
N-(2-aminophenyl)-4-(3-cyano-5-{[(2-methoxy-1-methylethyl)amino]methyl}pyridin-2-yl)benzamide;
N-(2-aminophenyl)-4-(3-cyano-5-{[(3-methoxypropyl)amino]methyl}pyridin-2-yl)benzamide;
N-(2-aminophenyl)-4-(3-cyano-5-{[(2-methoxybenzyl)amino]methyl}pyridin-2-yl)benzamide;
N-(2-aminophenyl)-4-(3-cyano-5-{[(3-methoxybenzyl)amino]methyl}pyridin-2-yl)benzamide;
N-(2-aminophenyl)-4-(3-cyano-5-{[(3-isopropoxypropyl)amino]methyl}pyridin-2-yl)benzamide;
N-(2-aminophenyl)-4-{3-cyano-5-[({[6-(trifluoromethyl)pyridin-3-yl]methyl}amino)methyl]pyridin-2-yl}benzamide;
N-(2-aminophenyl)-4-[3-cyano-5-({[(4-methyl-1,3-thiazol-2-yl)methyl]amino}methyl)pyridin-2-yl]benzamide;
N-(2-aminophenyl)-4-[3-cyano-5-({[2-(1-methyl-1H-imidazol-4-yl)ethyl]amino}methyl)pyridin-2-yl]benzamide;
N-(2-aminophenyl)-4-(3-cyano-5-{[(tetrahydrofuran-2-ylmethyl)amino]methyl}pyridin-2-yl)benzamide;
N-(2-aminophenyl)-4-(3-cyano-5-{[(2-ethoxyethyl)amino]methyl}pyridin-2-yl)benzamide;
N-(2-aminophenyl)-4-(3-cyano-5-{[(2-isopropoxyethyl)amino]methyl}pyridin-2-yl)benzamide;
N-(2-aminophenyl)-4-(3-cyano-5-{[(3-ethoxypropyl)amino]methyl}pyridin-2-yl)benzamide;
N-(2-aminophenyl)-4-(3-cyano-5-{[(2-propoxyethyl)amino]methyl}pyridin-2-yl)benzamide;
N-(2-aminophenyl)-4-[3-cyano-5-({[(5-methyl-2-furyl)methyl]amino}methyl)pyridin-2-yl]benzamide;
N-(2-aminophenyl)-4-(3-cyano-5-{[(tetrahydro-2H-pyran-4-ylmethyl)amino]methyl}pyridin-2-yl)benzamide;
N-(2-aminophenyl)-4-{3-cyano-5-[(tetrahydro-2H-pyran-4-ylamino)methyl]pyridin-2-yl}benzamide;
N-(2-aminophenyl)-4-(3-cyano-5-{[(2-methoxy-2-methylpropyl)amino]methyl}pyridin-2-yl)benzamide;
N-(2-aminophenyl)-4-(3-cyano-5-{[methyl(tetrahydrofuran-2-ylmethyl)amino]methyl}pyridin-2-yl)benzamide;
N-(2-aminophenyl)-4-(5-{[bis(2-methoxyethyl)amino]methyl}-3-cyanopyridin-2-yl)benzamide;

or a pharmaceutically acceptable salt thereof.

A suitable pharmaceutically-acceptable salt of a compound of the Formula (I) is, for example, an acid-addition salt of a compound of the Formula (I), for example an acid-addition salt with an inorganic or organic acid such as hydrochloric, hydrobromic, sulphuric, trifluoroacetic, citric or maleic acid; or, for example, a salt of a compound of the Formula (I) which is sufficiently acidic, for example an alkali or alkaline earth metal salt such as a calcium or magnesium salt, or an ammonium salt. A further suitable pharmaceutically acceptable salt of a compound of the Formula (I) is, for example, a salt formed within the human or animal body after administration of a compound of the Formula (I).

The compounds of the invention may be administered in the form of a pro-drug that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I) and in vivo cleavable amide derivatives that may be formed at a carboxy group or an amino group in a compound of the Formula (I).

Accordingly, the present invention includes those compounds of the Formula (I) as defined hereinbefore when made available by organic synthesis and when made available within the human or animal body by way of cleavage of a pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);

b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a carboxy group is, for example, an in vivo cleavable ester thereof. An in vivo cleavable ester of a compound of the Formula (I) containing a carboxy group is, for example, a pharmaceutically-acceptable ester, which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula (I) that possesses a hydroxy group is, for example, an in vivo cleavable ester or ether thereof. An in vivo cleavable ester or ether of a compound of the Formula (I) containing a hydroxy group is, for example, a pharmaceutically-acceptable ester or ether, which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula (I) that possesses a carboxy group is, for example, an in vivo cleavable amide thereof, for example an amide formed with an amine such as ammonia, a (1-4C)alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula (I) that possesses an amino group is, for example, an in vivo cleavable amide derivative thereof. Suitable pharmaceutically-acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

Another aspect of the present invention provides a process for preparing a compound of formula (I) or a pharmaceutically acceptable salt thereof (wherein $R^{1a}$, $R^{1b}$, $R^{1c}$, $R^2$, $R^3$, $R^4$, integer m and integer n are, unless otherwise specified, as hereinbefore defined), said process comprising the steps of:

(a) the reaction of a compound of the formula (A)

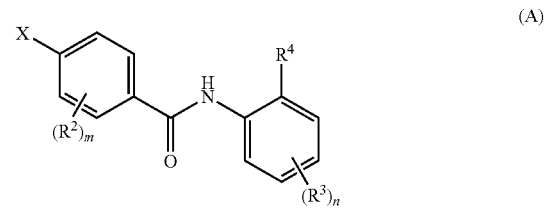

(A)

wherein X is a reactive group, with a compound of the formula (B)

(B)

wherein $R^{1a'}$ is a group $R^{1a}$ as hereinbefore defined or a precursor thereof, $R^{1b'}$ is a group $R^{1b}$ as hereinbefore defined or a precursor thereof, $R^{1c'}$ is a group $R^{1c}$ as hereinbefore defined or a precursor thereof, M is a metal, L is a ligand, and integer z is 0 to 3;

and wherein if any one of said groups $R^{1a'}$, $R^{1b'}$ or $R^{1c'}$ is a precursor for a $R^{1a}$, $R^{1b}$ or $R^{1c}$ group respectively, then said process thereafter comprises a step of converting the compound formed by the reaction of a compound of the formula (A) with a compound of the formula (B) to a compound of formula (I) (by converting the precursor of any one of groups $R^{1a}$, $R^{1b}$ or $R^{1c}$ group to the appropriate $R^{1a}$, $R^{1b}$ or $R^{1c}$ group); or (b) The reaction of a compound of the formula (C)

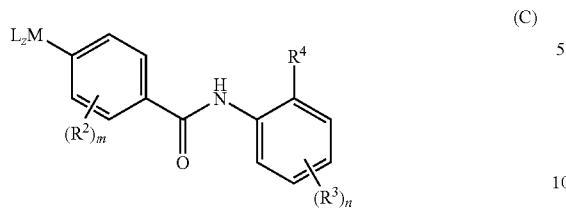

wherein M, L and integer z are as defined above,
with a compound of the formula (D)

wherein $R^{1a'}$, $R^{1b'}$ and $R^{1c'}$ are as defined above and X is a reactive group;

and wherein if any one of said groups $R^{1a'}$, $R^{1b'}$ or $R^{1c'}$ is a precursor for a $R^{1a}$, $R^{1b}$ or $R^{1c}$ group respectively, then said process comprises an additional step thereafter of converting the compound formed by the reaction of a compound of the formula (C) with a compound of the formula (D) to a compound of formula (I) (by converting the precursor of any one of groups $R^{1a}$, $R^{1b}$ or $R^{1c}$ group to the appropriate $R^{1a}$, $R^{1b}$ or $R^{1c}$ group); or (c) the reaction, in the presence of 4-(4,6-dimethoxy-1,3,5-triazinyl-2-yl)-4-methyhnorpholinium chloride, of a compound of the formula (E)

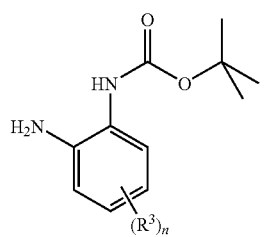

with a compound of the formula (F)

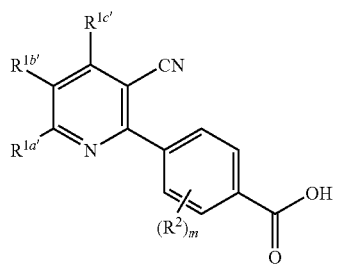

wherein $R^{1a'}$, $R^{1b'}$ and $R^{1c'}$ are as defined above, and wherein if any one of said groups $R^{1a'}$, $R^{1b'}$ or $R^{1c'}$ is a precursor for a $R^{1a}$, $R^{1b}$ or $R^{1c}$ group respectively, then said process comprises an additional step thereafter of converting the compound formed by the reaction of a compound of the formula (E) with a compound of the formula (F) to a compound of formula (I) (by converting the precursor of any one of groups $R^{1a}$, $R^{1b}$ or $R^{1c}$ group to the appropriate $R^{1a}$, $R^{1b}$ or $R^{1c}$ group);

and thereafter if necessary:
i) converting a compound of the formula (I) into another compound of the formula (I); and/or
ii) removing any protecting groups.

A suitable base for process (a), (b) or (c) is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride, or an alkali metal hydrogencarbonate such as sodium hydrogencarbonate, or a metal alkoxide such as sodium ethoxide.

A suitable reactive group X is, for example, a halo or a sulphonyloxy group, for example a chloro, bromo, iodo, methanesulphonyloxy, trifluoromethanesulphonyloxy or toluene-4-sulphonyloxy group.

The reactions are conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran, 1,2-dimethoxyethane or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reactions are conveniently carried out at a temperature in the range, for example, 10 to 250° C., preferably in the range 40 to 80° C.;

Metal M may be any metal that is known in the literature to form organometallic compounds that undergo catalytic cross coupling reactions. Examples of suitable metals include boron, tin, zinc, and magnesium.

A suitable value for integer z is dependent on the metal M, but is usually in the range 0-3.

Suitable values for the ligand L, when present, include, for example, a hydroxy, a halo, (1-4C)alkoxy or (1-6C)alkyl ligand, for example a hydroxy, bromo, chloro, fluoro, iodo, methoxy, ethoxy, propoxy, isopropoxy, butoxy, methyl, ethyl, propyl, isopropyl or butyl ligand or, where integer z is 2 and M is boron, the two ligands present may be linked such that, together with the boron atom to which they are attached, they form a ring.

Suitably, the group $ML_z$ is a group of the formula —$BL^1L^2$, where B is boron and $L^1$ and $L^2$ are as defined for ligand L above. In particular, the ligands $L^1$ and $L^2$ may be linked such that, together with the boron atom to which they are attached, they form a ring. For example, $L^1$ and $L^2$ together may define an oxy-(2-4C)alkylene-oxy group, for example an oxyethyleneoxy, pinacolato (—O—C(CH$_3$)$_2$C(CH$_3$)$_2$—O—) or oxypropyleneoxy group such that, together with the boron atom to which they are attached, they form a cyclic boronic acid ester group.

A suitable catalyst for process (a) or (b) includes, for example, a metallic catalyst such as a palladium(0), palladium(II), nickel(0) or nickel(II) catalyst, for example tetrakis(triphenylphosphine)palladium(0), palladium(II) chloride, palladium(II) bromide, bis(triphenylphosphine)palladium (II) chloride, tetrakis(triphenylphosphine)nickel(0), nickel (II) chloride, nickel(II) bromide, bis(triphenylphosphine)nickel(II) chloride or dichloro[1-1'-bis(diphenylphosphino) ferrocene]palladium(II). In addition, a free radical initiator may conveniently be added, for example an azo compound such as azo(bisisobutyronitrile).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, reductive amination of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green and P. G. M. Wuts, Protective Groups in Organic Synthesis, John Wiley and Sons, 1999). Thus, if reactants include groups such as amino, formyl, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Where any one of groups $R^{1a'}$, $R^{1b'}$ or $R^{1c'}$ is a precursor for a $R^{1a}$, $R^{1b}$ or $R^{1c}$ group respectively, it may be converted into a compound of formula (I) by converting the precursor of any one of groups $R^{1a}$, $R^{1b}$ or $R^{1c}$ to the appropriate $R^{1a}$, $R^{1b}$ or $R^{1c}$ group using standard chemical techniques that are well known to those skilled in the art. Examples of possible $R^{1a'}$, $R^{1b'}$ or $R^{1c'}$ precursor groups (particularly $R^{1b'}$ precursor groups) include hydroxy or alcohol-containing groups (e.g. —$CH_2OH$), aldehyde-containing groups (e.g. —CHO), carboxylic acid-containing groups (e.g. —$(CH_2)_{0-3}$—COOH), ester containing groups (e.g. —$(CH_2)_{0-3}$—$COOR^Z$, where $R^Z$ is (1-4C)alkyl), amide containing groups (e.g. —$CONH_2$), a group —$CH_2$—X where X is a reactive group as hereinbefore defined, or an activated ester group, such as a pentafluorphenoxy ester or an acyl chloride. A person skilled in the art will appreciate how to select the most appropriate precursor group for conversion into the desired $R^{1a}$, $R^{1b}$ or $R^{1c}$ is substituent groups.

For example, a compound of the present invention having the formula (XI) shown below (i.e. a compound of formula (I) in which $R^{1a}$ and $R^{1c}$ are both hydrogen; $R^{1b}$ is a group of the formula $R^7R^8N$—$CH_2$—; integer m is 0; integer n is 0; and $R^4$ is amino)

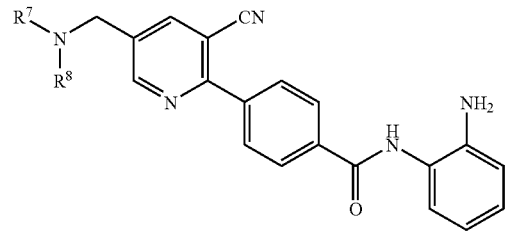

(XI)

is suitably prepared by a process (process (d)) comprising the reaction, in the presence of a suitable base, of a compound of formula (G) (wherein the aniline may be protected and $R^{1b}$ is a precursor for the $R^7R^7N$—$CH_2$— group in the compound of formula (VI) above, said precursor having the formula —$CH_2$—X, wherein X is a reactive group as hereinbefore defined),

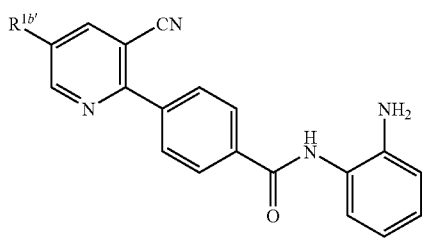

with a compound of formula (H);

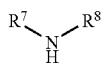

and thereafter, if necessary, removing any protecting groups.

Alternatively, a compound of general structural formula (XI) above may be prepared by a process (process (e)) which comprises the reaction, in the presence of a suitable reducing agent and a suitable acid, of a compound of formula (G) (wherein the aniline may be protected and $R^{1b'}$ is a precursor for the $R^7R^8N$—$CH_2$— group in the compound of formula (VI) above, said precursor having the formula —CHO (formyl)):

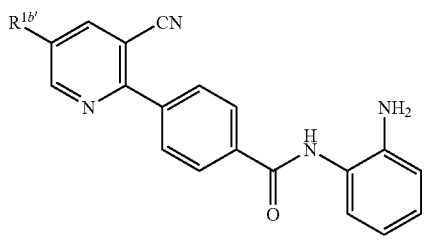

with a compound of formula (H);

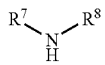

and thereafter, if necessary, removing any protecting groups.

A suitable base for process (d) is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride, or an alkali earth metal hydrogencarbonate such as sodium hydrogencarbonate, or a metal alkoxide such as sodium ethoxide.

A suitable reducing agent for process (e) includes, for example, an inorganic borohydride salt such as, sodium borohydride, sodium triacetoxyborohydride or sodium cyanoborohydride.

A suitable acid for process (e), includes a Bronsted acid such as, for example formic acid, acetic acid, trifluoroacetic acid, hydrochloric acid, sulphuric acid, paratoluene sulfonic acid or camphor sulfonic acid; or a Lewis acid of formula $MX_z$, wherein M is a metal, X is a reactive group as hereindefined and z is in the range of 1-6 and the value of z will depend on the metal M. Typical examples of suitable Lewis acids include boron trifluoride, scandium(III) trifluoromethanesulfonate, tin(VI) chloride, titanium(IV) isopropoxide or zinc(I) chloride.

The present invention also provides a particular process (process (g)) for preparing a particular sub-group of compounds of formula (D) for use in process (b) above which have the formula (D') shown below,

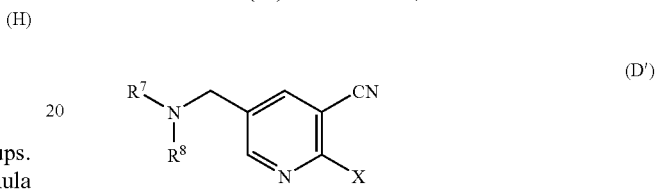

(i.e. compounds of formula D above wherein $R^{1a'}$ and $R^{1c'}$ are both hydrogen and $R^{1b'}$ is a group $R^7R^8N$—$CH_2$— where $R^7$ and $R^8$ are any substituent group as hereinbefore defined except hydrogen, said process comprising the steps of:

(i) reacting, in a suitable solvent, a substituted acrolein of formula (J), wherein $R_{50}$ is a suitable leaving group,

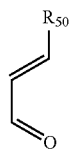

with formaldehyde and a compound of formula (H)

to form a compound of formula (L);

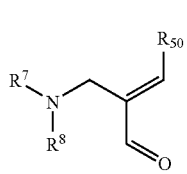

(ii) reacting, in a suitable solvent and in the presence of a suitable base, the compound of formula (L) prepared in step (i) above with 2-cyanoacetamide to form a compound of formula (M) as a metal salt;

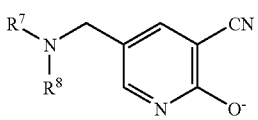

(M)

(iii) converting compound (M) to compounds of formula (D') and thereafter, if necessary, removing any protecting groups.

The compounds of formula (D') prepared above are then used in process (b) above to form a compound of formula VI above.

In step (iii) of process (g), above, any suitable method known in the art for converting compound (M) to a compound of formula (D') may be used. This conversion involves the substitution of the —O⁻ group of compound (M) with a reactive group X as hereinbefore defined (e.g. a halogen). For example, compound (M) may be converted into a compound of formula (D') in which X is chloro by a chlorination reaction. Such a reaction may involve the neutralisation of the compound of formula (M) followed by chlorination with phosphorus oxychloride.

Suitably $R_{50}$ is a substituted amino group, particularly a (1-6C)alkyl amino group (e.g. dimethylamino) a substituted-(1-6C)alkyl (e.g. benzyl)amino group. 3-(dimethylamino)acrolein is especially preferred.

A suitable solvent for steps (i) and (ii) of process (g) is an alcohol such as ethanol.

A suitable base for step (ii) is any of those mentioned for processes (a) to (c) above, particularly an alkaline metal alkoxide such as sodium ethoxide.

Biological Assays

The following assays can be used to measure the effects of the compounds of the present invention as HDAC inhibitors, as inhibitors in vitro of recombinant human HDAC1 produced in Hi5 insect cells, and as inducers in vitro & in vivo of Histone H3 acetylation in whole cells and tumours. They also assess the ability of such compounds to inhibit proliferation of human tumour cells.

(a) In Vitro Enzyme Assay of recombinant HDAC1

HDAC inhibitors were screened against recombinant human HDAC1 produced in Hi5 insect cells. The enzyme was cloned with a FLAG tag at the C-terminal of the gene and affinity purified using Anti-FLAG M2 agarose from SIGMA (A2220).

The deacetylase assays were carried out in a 50 µl reaction. HDAC1 (75 ng of enzyme) diluted in 15 µl of reaction buffer (25 mM Tris HCl (pH 8), 137 mM NaCl, 2.7 mM KCl, 1 mM $MgCl_2$) was mixed with either buffer alone (10 µl) or buffer containing compound (10 µl) for 30 minutes at ambient temperature. The 25 µM acetylated histone H4 peptide (KI 174 Biomol) diluted in 25 µl of buffer was then added to the reaction and incubated for one hour at ambient temperature. The reaction was stopped by addition of an equal volume (50 µl) Fluor de Lys developer (Biomol) containing Trichostatin A at 2 µM. The reaction was allowed to develop for 30 minutes at ambient temperature and then fluorescence measured at an excitation wavelength of 360 nM and an emission wavelength of 465 nM. The $IC_{50}$ values for HDAC enzyme inhibitors were determined by performing dose response curves with individual compounds and determining the concentration of inhibitor producing fifty percent decrease in the maximal signal (diluent control).

(b) In Vitro Assay of Inhibition of Proliferation in Whole Cells

Inhibition of proliferation in whole cells was assayed using the Promega cell titer 96 aqueous proliferation assay (Promega #G5421). The HCT116 cells were seeded in 96 well plates at $1 \times 10^3$ cells/well, and allowed to adhere overnight. They were treated with inhibitors for 72 hours. The 20 µl of the tetrazolium dye MTS was added to each well and the plates were reincubated for 3 hours. Absorbance was then measured on a 96 well plate reader at 490 nM. The $IC_{50}$ values for HDAC inhibitors were determined by performing dose response curves with individual compounds and determining the concentration of inhibitor producing fifty percent decrease in maximal signal (diluent control).

Although the pharmacological properties of the compounds of the formula (I) vary with structural change as expected, in general activity possessed by compounds of the Formula (I), may be demonstrated at the following concentrations or doses in one or more of the above tests (a)-(b):

Test (a):—$IC_{50}$ in the range, for example, <0.060 µM;
Test (b):—$IC_{50}$ in the range, for example, <0.80 µM.

The following table discloses various biological data for a representative selection of compounds of the present invention. Comparative test data is also provided for N-(2-aminophenyl)-4-pyridin-2-ylbenzamide (Comparator).

| EXAMPLE (COMPOUND NO.) | Test (a) $IC_{50}$ (µM) | Test (b) $IC_{50}$ (µM) |
| --- | --- | --- |
| 1 | 0.013 | 0.289 |
| 2 (10) | 0.003 | 0.211 |
| 2 (12) | 0.006 | 0.218 |
| 5 (15) | 0.012 | 0.287 |
| Comparator | 0.089 | 2.33 |

According to a further aspect of the invention there is provided a pharmaceutical composition, which comprises a compound of the formula (I), or a pharmaceutically acceptable salt thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg/m² body area of the animal, i.e. approximately is 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

We have found that the compounds defined in the present invention, or a pharmaceutically acceptable salt thereof, are effective cell cycle inhibitors (anti-cell proliferation agents), which property is believed to arise from their HDAC inhibitory properties. We also believe that the compounds of the present invention may be involved in the inhibition of angiogenesis, activation of apoptosis and differentiation. Accordingly the compounds of the present invention are expected to be useful in the treatment of diseases or medical conditions mediated alone or in part by HDAC enzymes, i.e. the compounds may be used to produce a HDAC inhibitory effect in a warm-blooded animal in need of such treatment. Thus, the compounds of the present invention provide a method for treating the proliferation of malignant cells characterised by inhibition of HDAC enzymes, i.e. the compounds may be used to produce an anti-proliferative effect mediated alone or in part by the inhibition of HDACs.

According to one aspect of the present invention there is provided a compound of the formula (I), or a pharmaceutically acceptable salt thereof, as defined hereinbefore for use in a method of treatment of the human or animal body by therapy.

Thus according to a further aspect of the invention there is provided a compound of the formula (I), or a pharmaceutically acceptable salt thereof, as defined hereinbefore for use as a medicament.

According to a further aspect of the invention there is provided the use of a compound of the formula (I), or a pharmaceutically acceptable salt thereof, as defined hereinbefore in the manufacture of a medicament for use in the production of a HDAC inhibitory effect in a warm-blooded animal such as man.

According to a further feature of this aspect of the invention there is provided a method for producing a HDAC inhibitory effect in a warm-blooded animal, such as man, in need of such treatment which comprises administering to said animal an effective amount of a compound of the formula (I), or a pharmaceutically acceptable salt thereof, as defined hereinbefore.

According to a further aspect of the invention there is provided the use of a compound of the formula (I), or a pharmaceutically acceptable salt thereof, as defined hereinbefore in the manufacture of a medicament for use in the production of a cell cycle inhibitory (anti-cell-proliferation) effect in a warm-blooded animal such as man.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of the formula (I), or a pharmaceutically acceptable salt thereof, as defined hereinbefore.

According to an additional feature of this aspect of the invention there is provided a method of treating cancer in a warm-blooded animal, such as man, in need of such treatment which comprises administering to said animal an effective amount of a compound of the formula (I), or a pharmaceutically acceptable salt thereof, as defined hereinbefore.

According to a further feature of the invention there is provided a compound of the formula (I), or a pharmaceutically acceptable salt thereof, as defined hereinbefore in the manufacture of a medicament for use in the treatment of cancer.

According to an additional feature of this aspect of the invention there is provided a compound of the formula (I), or a pharmaceutically acceptable salt thereof, as defined hereinbefore, for use in the treatment of cancer.

According to an additional feature of this aspect of the invention there is provided the use of a compound of the formula (I), or a pharmaceutically acceptable salt thereof, as defined hereinbefore, for use in the manufacture of a medicament for the treatment of cancer.

In a further aspect of the present invention there is provided the use of a compound of the formula (I), or a pharmaceutically acceptable salt thereof, as defined hereinbefore, in the manufacture of a medicament for use in lung cancer, colorectal cancer, breast cancer, prostate cancer, lymphoma and/or leukaemia.

In a further aspect of the present invention there is provided a method of treating lung cancer, colorectal cancer, breast cancer, prostate cancer, lymphoma or leukaemia, in a warm-blooded animal, such as man, in need of such treatment which comprises administering to said animal an effective amount of a compound of the formula (I), or a pharmaceutically acceptable salt thereof, as defined hereinbefore.

Cancers that are amenable to treatment with the present invention include oesophageal cancer, myeloma, hepatocellular, pancreatic and cervical cancer, Ewings tumour, neuroblastoma, kaposis sarcoma, ovarian cancer, breast cancer, colorectal cancer, prostate cancer, bladder cancer, melanoma, lung cancer [including non small cell lung cancer (NSCLC) and small cell lung cancer (SCLC)], gastric cancer, head and neck cancer, brain cancer, renal cancer, lymphoma and leukaemia.

There is further provided is a compound of the formula (I), or a pharmaceutically acceptable salt thereof, as defined hereinbefore, for use in a method of treating inflammatory diseases, autoimmune diseases and allergic/atopic diseases.

In particular a compound of the formula (I), or a pharmaceutically acceptable salt thereof, as defined hereinbefore, is provided for use in a method of treating inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is a compound of the formula (I), or a pharmaceutically acceptable salt thereof, as defined hereinbefore, for use as a medicament in the treatment of inflammatory diseases, autoimmune diseases and allergic/atopic diseases in a warm-blooded animal such as man.

In particular a compound of the formula (I), or a pharmaceutically acceptable salt thereof, as defined hereinbefore, is provided for use as a medicament in the treatment of inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis), multiple sclerosis, atherosclerosis, spondyloarthropathies (ankylosing spondylitis, psoriatic arthritis, arthritis connected to ulcerative colitis), AIDS-related neuropathies, systemic lupus erythematosus, asthma, chronic obstructive lung diseases, bronchitis, pleuritis, adult respiratory distress syndrome, sepsis, and acute and chronic hepatitis (either viral, bacterial or toxic).

Further provided is the use of a compound of the formula (I), or a pharmaceutically acceptable salt thereof, as defined hereinbefore, in the manufacture of a medicament for use in the treatment of inflammatory diseases, autoimmune diseases and allergic/atopic diseases in a warm-blooded animal such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The HDAC inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) Cell cycle inhibitors including for example CDK inhibitiors (eg flavopiridol) and other inhibitors of cell cycle checkpoints (eg checkpoint kinase); inhibitors of aurora kinase and other kinases involved in mitosis and cytokinesis regulation (eg mitotic kinesins); and other histone deacetylase inhibitors; and (xi) differentiation agents (for example retinoic acid and vitamin D).

According to this aspect of the invention there is provided a pharmaceutical composition comprising a compound of the formula (I) as defined hereinbefore and an additional antitumour substance as defined hereinbefore for the conjoint treatment of cancer.

In addition to their use in therapeutic medicine, the compounds of formula (I) and their pharmaceutically acceptable salts thereof, are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or using proprietary pre-packed normal phase silica catridges, for example Redisep™ disposable chromatography cartridges obtained from Presearch Ltd., Hitchin, UK, or high pressure liquid chromatography (HPLC) was performed on C18 reverse phase silica, for example on a Dynamax C-18 60 Å preparative reversed-phase column;

(iv) yields, where present, are not necessarily the maximum attainable;

(v) in general, the structures of the end-products of the Formula (I) were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz—measurements were taken at ambient temperature unless otherwise specified;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the formula (I) were determined after crystallisation from a conventional organic solvent such as ethanol, methanol, acetone, ether or hexane, alone or in admixture;

(viii) the following abbreviations have been used:
DMF N,N-dimethylformamide
DMSO dimethylsulphoxide
THF tetrahydrofuran (ix) the abbreviation sm is used to refer to the starting material; all starting materials were commercially available unless otherwise stated (by reference to a preparative method described herein or by reference to a published reference).

EXAMPLE 1

N-(2-aminophenyl)-4-(3-cyanopyridin-2-yl)benzamide

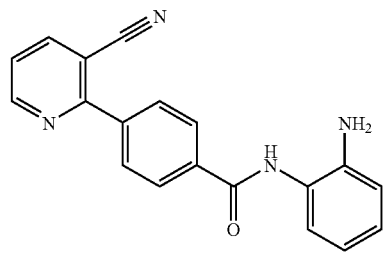

N-(2-t-Butoxycarbonylaminophenyl)-4-(3-cyanopyridin-2-yl)benzamide (210 mg; prepared as described in Method 1 below), 1,4-dioxane (6.8 ml) and a 4M solution of hydrogen chloride in 1,4-dioxane (6.8 ml) were stirred at ambient temperature for 20 hours. The resultant precipitate was collected by filtration and washed with diethyl ether (3×), suspended in water, basified with a 2M aqueous solution of sodium hydroxide and extracted with dichloromethane. The organic extract was dried over sodium sulfate to afford the title compound as a cream solid (130 mg, 82%); NMR Spectrum: (DMSO-$d_6$) 4.94 (br s, 2H), 6.60 (m, 1H), 6.78 (m, 1H), 6.98 (m, 1H), 7.19 (d, 1H), 7.65 (m, 1H), 7.98 (d, 2H), 8.14 (d, 2H), 8.46 (m, 1H), 8.98 (m, 1H), 9.77 (s, 1H); Mass Spectrum: M+H$^+$ 315.

EXAMPLE 2

Using an analogous procedure to that described in Example 1, the appropriate N-(2-t-butoxycarbonylaminophenyl)-4-(3-cyanopyridin-2-yl)benzamide starting material was reacted to give the compounds shown in Table 1.

TABLE 1

| Compound | X | Analytical Data | SM |
|---|---|---|---|
| 1 | 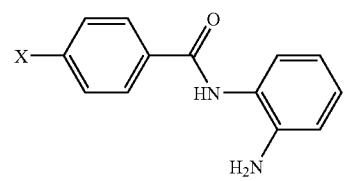 | NMR Spectrum: (DMSO-$d_6$) 2.41 (s, 3H), 4.94 (br s, 2H), 6.60 (m, 1H), 6.78 (d, 1H), 6.98 (m, 1H), 7.19 (d, 1H), 7.95 (d, 2H), 8.14 (d, 2H) 8.30 (d, 1H), 8.82 (d, 1H), 9.77 (s, 1H); Mass Spectrum: M + H$^+$ 329. | Method 2 |

TABLE 1-continued

| Compound | X | Analytical Data | SM |
|---|---|---|---|
| 2 | 4-dimethylamino-3-cyano-pyridin-2-yl | NMR Spectrum: (DMSO-$d_6$) 3.23 (s, 6H), 4.92 (br s, 2H), 6.60 (m, 1H), 6.78 (m, 1H), 6.89 (d, 1H), 6.97 (m, 1H), 7.19 (m, 1H), 7.86 (d, 2H), 8.06 (d, 2H), 8.33 (d, 1H), 9.75 (s, 1H); Mass Spectrum: M + H$^+$ 358. | Method 3 |
| 3 | 6-ethylamino-4-methyl-3-cyano-pyridin-2-yl | NMR Spectrum: (DMSO-$d_6$) 1.15 (t, 3H), 2.35 (s, 3H), 3.35 (m, 2H), 4.92 (br s, 2H), 6.45 (s, 1H), 6.60 (m, 1H), 6.78 (m, 1H), 6.97 (m, 1H), 7.19 (m, 1H), 7.56 (m, 1H), 7.86 (d, 2H), 8.06 (d, 2H), 9.70 (s, 1H); Mass Spectrum: M + H$^+$ 372. | Method 4 |
| 4 | 6-(2-hydroxyethylamino)-4-methyl-3-cyano-pyridin-2-yl | NMR Spectrum: (DMSO-$d_6$) 2.35 (s, 3H), 3.30-3.60 (m, 4H), 6.51 (s, 1H), 6.63 (m, 1H), 6.79 (d, 1H), 6.97 (m, 1H), 7.19 (d, 1H), 7.57 (m, 1H), 7.86 (d, 2H), 8.06 (d, 2H), 9.73 (s, 1H); Mass Spectrum: M + H$^+$ 388. | Method 5 |
| 5 | 4,6-dimethyl-3-cyano-pyridin-2-yl | NMR Spectrum: (DMSO-$d_6$) 2.54 (s, 3H), 2.59 (s, 3H), 4.94 (br s, 2H), 6.60 (m, 1H), 6.78 (d, 1H), 6.97 (m, 1H), 7.19 (d, 1H), 7.45 (s, 1H), 7.91 (d, 2H), 8.12 (d, 2H), 9.77 (s, 1H); Mass Spectrum: M + H$^+$ 343. | Method 6 |
| 6 | 5-(piperidin-1-ylmethyl)-3-cyano-pyridin-2-yl | NMR Spectrum: (DMSO-$d_6$) 1.39 (m, 2H), 1.51 (m, 4H), 2.40 (m, 4H), 3.58 (s, 2H), 4.94 (br s, 2H), 6.60 (m, 1H), 6.78 (m, 1H), 6.98 (m, 1H), 7.19 (d, 1H), 7.98 (d, 2H), 8.14 (d, 2H), 8.30 (d, 1H), 8.86 (d, 1H), 9.78 (s, 1H); Mass Spectrum: M + H$^+$ 412. | Method 8 |
| 7 | 6-(4-methylpiperazin-1-yl)-4-methyl-3-cyano-pyridin-2-yl | NMR Spectrum: (DMSO-$d_6$) 2.21 (s, 3H), 2.40 (m, 4H), 2.44 (s, 3H), 3.70 (m, 4H), 4.92 (br s, 2H), 6.60 (m, 1H), 6.78 (d, 1H), 6.93 (s, 1H), 6.97 (m, 1H), 7.19 (d, 1H), 7.88 (d, 2H), 8.07 (d, 2H), 9.70 (s, 1H); Mass Spectrum: M + H$^+$ 427. | Method 7 |
| 8 | 5-(pyrrolidin-1-ylmethyl)-3-cyano-pyridin-2-yl | NMR Spectrum: (DMSO-$d_6$ 343K) 1.74 (m, 4H), 2.53 (m, 4H), 3.76 (s, 2H), 4.80 (br s, 2H), 6.62 (m, 1H), 6.81 (m, 1H), 6.98 (m, 1H), 7.25 (m, 1H), 7.99 (d, 2H), 8.14 (d, 2H), 8.28 (d, 1H), 8.88 (d, 1H), 9.63 (s, 1H); Mass Spectrum: M + H$^+$ 398. | Method 9 |

TABLE 1-continued

| Compound | X | Analytical Data | SM |
|---|---|---|---|
| 9 | (3-phenylpyrrolidin-1-yl)methyl-substituted cyanopyridine | NMR Spectrum: (DMSO-d$_6$) 1.80 (m, 1H), 2.27 (m, 1H), 2.51 (m, 1H), 2.76 (m, 2H), 2.99 (t, 1H), 3.34 (m, 1H), 3.80 (s, 2H), 4.93 (br s, 2H), 6.60 (m, 1H), 6.79 (d, 1H), 6.98 (m, 1H), 7.18 (m, 2H), 7.29 (m, 4H), 7.98 (d, 2H), 8.14 (d, 2H), 8.37 (d, 1H), 8.92 (d, 1H), 9.77 (s, 1H); Mass Spectrum: M + H$^+$ 474. | Method 10 |
| 10 | (3-(pyridin-2-yl)pyrrolidin-1-yl)methyl-substituted cyanopyridine | NMR Spectrum: (DMSO-d$_6$) 2.05 (m, 1H), 2.24 (m, 1H), 2.68 (m, 2H), 2.84 (m, 1H), 3.04 (t, 1H), 3.52 (m, 1H), 3.80 (s, 2H), 4.93 (br s, 2H), 6.60 (m, 1H), 6.78 (d, 1H), 6.98 (m, 1H), 7.19 (m, 2H), 7.31 (d, 1H), 7.69 (m, 1H), 7.98 (d, 2H), 8.14 (d, 2H), 8.37 (d, 1H), 8.48 (m, 1H), 8.91 (d, 1H), 9.77 (s, 1H); Mass Spectrum: M + H$^+$ 475. | Method 11 |
| 11 | (6-(hydroxymethyl)-3-azabicyclo[3.1.0]hexan-3-yl)methyl-substituted cyanopyridine | NMR Spectrum: (DMSO-d$_6$) 1.27 (s, 2H), 1.34 (m, 1H), 2.38 (d, 2H), 2.91 (d, 2H), 3.24 (m, 2H), 3.71 (s, 2H), 4.37 (t, 1H), 4.93 (br s, 2H), 6.60 (m, 1H), 6.78 (d, 1H), 6.98 (m, 1H), 7.19 (d, 1H), 7.98 (d, 2H), 8.14 (d, 2H), 8.27 (d, 1H), 8.84 (d, 1H), 9.77 (s, 1H); Mass Spectrum: M + H$^+$ 440. | Method 12 |
| 12 | (2,5-dimethylpyrrolidin-1-yl)methyl-substituted cyanopyridine | NMR Spectrum: (DMSO-d$_6$) 0.97 (d, 6H), 1.8 (m, 2H), 1.98 (m, 2H), 3.00 (m, 2H), 3.80 (dd, 2H), 4.92 (br s, 2H), 6.60 (m, 1H), 6.78 (d, 1H), 6.98 (m, 1H), 7.19 (d, 1H), 7.98 (d, 2H), 8.13 (d, 2H), 8.31 (d, 1H), 8.90 (d, 1H), 9.77 (s, 1H); Mass Spectrum: M + H$^+$ 426. | Method 13 |
| 13 | (3-(dimethylamino)pyrrolidin-1-yl)methyl-substituted cyanopyridine | NMR Spectrum: (DMSO-d$_6$) 1.63 (m, 1H), 1.87 (m, 1H), 2.08 (s, 6H), 2.13 (d, 1H), 2.33 (m, 1H), 2.61 (m, 1H), 2.66-2.76 (m, 2H), 3.70 (dd, 2H), 4.94 (br s, 2H), 6.60 (m, 1H), 6.78 (d, 1H), 6.98 (m, 1H), 7.19 (d, 1H), 7.98 (d, 2H), 8.13 (d, 2H), 8.31 (d, 1H), 8.87 (d, 1H), 9.77 (s, 1H); Mass Spectrum: M + H$^+$ 441. | Method 14 |

EXAMPLE 3

Using an analogous procedure to that described in example 1, the appropriate n-(2-t-butoxycarbonylaminophenyl)-4-(3-cyanopyridin-2-yl)benzamide starting material was reacted to give the compounds shown in table 2 below.

TABLE 2

| Compound | X | Analytical Data | SM |
|---|---|---|---|
| 1 | 6-nitro-3-cyanopyridin-2-yl (N-oxide) | NMR Spectrum: (DMSO-d$_6$) 4.95 (br s, 2H), 6.60 (m, 1H), 6.80 (d, 1H), 6.98 (m, 1H), 7.20 (d, 1H), 8.02 (d, 2H), 8.20 (d, 2H), 9.36 (d, 1H), 9.69 (d, 1H), 9.80 (s, 1H); Mass Spectrum: M – H$^-$ 358. | Method 16 |
| 2 | 6-(4-fluorophenyl)-3-cyanopyridin-2-yl | NMR Spectrum: (DMSO-d$_6$) 4.93 (br s, 2H), 6.60 (m, 1H), 6.80 (d, 1H), 6.99 (m, 1H), 7.2 (d, 1H), 7.40 (m, 2H), 8.08 (d, 2H), 8.17 (d, 2H), 8.22 (d, 1H), 8.32 (m, 2H), 8.52 (d, 1H), 9.78 (s, 1H); Mass Spectrum: M + H$^+$ 409. | Method 17 |
| 3 | 6-amino-3,5-dicyanopyridin-2-yl | NMR Spectrum: (DMSO-d$_6$) 4.92 (br s, 2H), 6.60 (m, 1H), 6.79 (d, 1H), 6.98 (m, 1H), 7.19 (d, 1H), 7.90 (d, 2H), 8.05 (br s, 2H), 8.11 (d, 2H), 8.60 (s, 1H), 9.78 (s, 1H); Mass Spectrum: M + H$^+$ 355. | Method 18 |

EXAMPLE 4

N-(2-aminophenyl)-4-(3-cyano-5-{[4-(2-oxo-2-pyrrolidin-1-ylethyl)piperazin-1-yl]methyl}pyridin-2-yl)benzamide

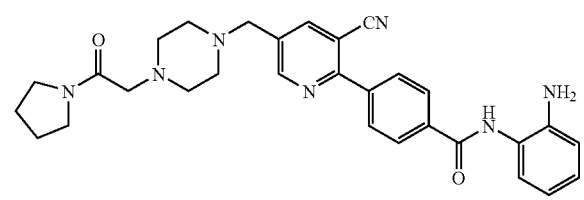

N-(2-t-Butoxycarbonylaminophenyl)-4-(3-cyano-5-formylpyridin-2-yl)benzamide (0.3 g, prepared as described in Method 15 below) and 1-(pyrrolidinocarbonylmethyl)piperazine (0.14 g) were dissolved in dichloromethane (10 ml). Sodium triacetoxyborohydride (0.15 g) was added, and the mixture stirred for 3 hours before being washed with water (10 ml). The organic residues were separated and purified using flash column chromatography eluting with ethyl acetate, followed by (6-8%) MeOH in dichloromethane to give t-butyl (2-{[4-(3-cyano-5-{[4-(2-oxo-2-pyrrolidin-1-ylethyl)piperazin-1-yl]methyl}pyridin-2-yl)benzoyl]amino}phenyl)carbamate (300 mg) as a pale yellow oil. The oil was dissolved in methanol (10 ml), and a 4M solution of hydrogen chloride in 1,4-dioxan (10 ml) added and the solution stirred at ambient temperature for 2 hours. The solvent was evaporated, methanol (5 ml) added and the resulting solution absorbed onto an SCX-2 column, which was then washed with methanol (2 column volumes) and the product eluted with a 2M solution of ammonia in methanol (2 column volumes). The ammonia/methanol was evaporated to give a foam. This was treated with diethyl ether (20 ml), stirred and filtered to give the product as a white solid (195 mg, 57%); NMR Spectrum: (DMSO-d$_6$ 373K) 1.82 (m, 4H), 2.50 (m, 8H), 3.11 (s, 2H), 3.40 (m, 4H), 3.66 (s, 2H), 4.74 (br s, 2H), 6.64 (m, 1H), 6.82 (m, 1H), 6.98 (m, 1H), 7.27 (m, 1H), 7.99 (d, 2H), 8.13 (d, 2H), 8.24 (d, 1H), 8.87 (d, 1H), 9.49 (br s, 1H); Mass Spectrum: M+H$^+$ 524.

EXAMPLE 5

Using an analogous procedure to that described in Example 4, the appropriate amine starting material was reacted with N-(2-t-butoxycarbonylaminophenyl)-4-(3-cyano-5-formylpyridin-2-yl)benzamide to give the compounds shown in Table 3 below.

TABLE 3

| Compound | X | Analytical Data | SM |
|---|---|---|---|
| 1 | diethylaminomethyl-cyanopyridinyl | NMR Spectrum: (DMSO-d$_6$ 373K) 1.09 (t, 6H), 2.64 (q, 4H), 3.79 (s, 2H), 4.77 (br s, 2H), 6.64 (m, 1H), 6.82 (m, 1H), 6.98 (m, 1H), 7.28 (m, 1H), 7.99 (d, 2H), 8.14 (d, 2H), 8.27 (s, 1H), 8.90 (s, 1H), 9.49 (br s, 1H); Mass Spectrum: M + H$^+$ 400. | |
| 2 | piperazinylmethyl-cyanopyridinyl | NMR Spectrum: (DMSO-d$_6$ 373K) 2.43 (m, 4H), 2.80 (m, 4H), 3.66 (s, 2H), 4.73 (br s, 2H), 6.66 (m, 1H), 6.84 (m, 1H), 7.01 (m, 1H), 7.30 (m, 1H), 8.02 (d, 2H), 8.16 (d, 2H), 8.27 (d, 1H), 8.88 (d, 1H), 9.49 (br s, 1H); Mass Spectrum: M + H$^+$ 413. | |
| 3 | isopropylpiperazinylmethyl-cyanopyridinyl | NMR Spectrum: (DMSO-d$_6$ 373K) 0.99 (d, 6H), 2.50 (m, 8H), 2.67 (m, 1H), 3.66 (s, 2H), 4.72 (br s, 2H), 6.64 (m, 1H), 6.82 (m, 1H), 6.98 (m, 1H), 7.27 (m, 1H), 8.00 (d, 2H), 8.14 (d, 2H), 8.24 (d, 1H), 8.87 (d, 1H), 9.49 (br s, 1H); Mass Spectrum: M + H$^+$ 455. | |
| 4 | methylpiperazinylmethyl-cyanopyridinyl | NMR Spectrum: (DMSO-d$_6$ 373K) 2.22 (s, 3H), 2.50 (m, 8H), 3.66 (s, 2H), 4.72 (br s, 2H), 6.64 (m, 1H), 6.82 (m, 1H), 6.98 (m, 1H), 7.28 (m, 1H), 7.99 (d, 2H), 8.13 (d, 2H), 8.23 (d, 1H), 8.87 (d, 1H), 9.49 (br s, 1H); Mass Spectrum: M + H$^+$ 427. | |
| 5 | hydroxyethylpiperazinylmethyl-cyanopyridinyl | NMR Spectrum: (DMSO-d$_6$ 373K) 2.50 (m, 10H), 3.55 (t, 2H), 3.68 (s, 2H), 3.98 (br s, 1H), 4.72 (br s, 2H), 6.64 (m, 1H), 6.82 (m, 1H), 6.98 (m, 1H), 7.28 (m, 1H), 7.99 (d, 2H), 8.14 (d, 2H), 8.24 (d, 1H), 8.87 (d, 1H), 9.49 (br s, 1H); Mass Spectrum: M + H$^+$ 457. | |
| 6 | ethylpiperazinylmethyl-cyanopyridinyl | NMR Spectrum: (DMSO-d$_6$ 373K) 0.99 (t, 3H), 2.41 (q, 2H), 2.50 (m, 8H), 3.68 (s, 2H), 4.72 (br s, 2H), 6.65 (m, 1H), 6.84 (m, 1H), 7.01 (m, 1H), 7.29 (m, 1H), 8.02 (d, 2H), 8.15 (d, 2H), 8.25 (d, 1H), 8.89 (d, 1H), 9.51 (br s, 1H); Mass Spectrum: M + H$^+$ 441. | |
| 7 | acetylpiperazinylmethyl-cyanopyridinyl | NMR Spectrum: (DMSO-d$_6$ 373K) 1.99 (s, 3H), 2.50 (m, 4H), 3.49 (m, 4H), 3.70 (s, 2H), 4.72 (br s, 2H), 6.63 (m, 1H), 6.82 (m, 1H), 6.98 (m, 1H), 7.28 (m, 1H), 8.00 (d, 2H), 8.14 (d, 2H), 8.28 (d, 1H), 8.89 (d, 1H), 9.50 (br s, 1H); Mass Spectrum: M + H$^+$ 455. | |
| 8 | (N-methyl-N-(2-methoxyethyl)aminomethyl)-cyanopyridinyl | NMR Spectrum: (DMSO-d$_6$ 373K) 2.55 (s, 3H), 2.99 (m, 2H), 3.31 (s, 3H), 3.67 (t, 2H), 4.10 (s, 2H), 6.64 (m, 1H), 6.83 (m, 1H), 6.99 (m, 1H), 7.28 (m, 1H), 8.02 (d, 2H), 8.16 (d, 2H), 8.48 (d, 1H), 9.00 (d, 1H), 9.53 (br s, 1H); Mass Spectrum: M + H$^+$ 416. | |

TABLE 3-continued

| Compound | X | Analytical Data | SM |
|---|---|---|---|
| 9 | azetidin-1-ylmethyl-(3-cyano-pyridin-2-yl) | NMR Spectrum: (DMSO-d$_6$) 2.12 (m, 2H), 3.45 (m, 4H), 3.92 (s, 2H), 4.92 (br s, 2H), 6.62 (m, 1H), 6.80 (m, 1H), 7.00 (m, 1H), 7.20 (m, 1H), 7.99 (d, 2H), 8.18 (d, 2H), 8.39 (s, 1H), 8.92 (s, 1H), 9.81 (br s, 1H); Mass Spectrum: M + H$^+$ 384. | |
| 10 | [isopropyl(2-methoxyethyl)amino]methyl-(3-cyano-pyridin-2-yl) | NMR Spectrum: (DMSO-d$_6$) 1.20 (m, 6H), 3.10 (m, 10H), 4.16 (br s, 1H), 5.12 (br s, 1H), 6.62 (m, 1H), 6.82 (m, 1H), 6.98 (m, 1H), 7.22 (m, 1H), 8.02 (d, 2H), 8.18 (d, 2H), 8.62 (m, 1H), 9.08 (m, 1H), 9.88 (br s, 1H); Mass Spectrum: M + H$^+$ 444. | |
| 11 | [ethyl(2-hydroxyethyl)amino]methyl-(3-cyano-pyridin-2-yl) | NMR Spectrum: (DMSO-d$_6$ 373K) 1.08 (t, 3H), 2.67 (m, 4H), 3.57 (t, 2H), 3.83 (s, 2H), 4.12 (br s, 1H), 4.72 (br s, 2H), 6.64 (m, 1H), 6.82 (m, 1H), 6.98 (m, 1H), 7.28 (m, 1H), 8.00 (d, 2H), 8.13 (d, 2H), 8.31 (d, 1H), 8.90 (d, 1H), 9.50 (br s, 1H); Mass Spectrum: M + H$^+$ 416. | |
| 12 | [(2-methoxyethyl)amino]methyl-(3-cyano-pyridin-2-yl) | NMR Spectrum: (DMSO-d$_6$ 373K) 2.80 (t, 2H), 3.29 (s, 3H), 3.48 (t, 2H), 3.93 (s, 2H), 4.70 (br s, 2H), 6.63 (m, 1H), 6.82 (m, 1H), 6.98 (m, 1H), 7.27 (m, 1H), 8.00 (d, 2H), 8.14 (d, 2H), 8.31 (d, 1H), 8.90 (d, 1H), 9.49 (br s, 1H); Mass Spectrum: M + H$^+$ 402. | |
| 13 | [ethyl(methyl)amino]methyl-(3-cyano-pyridin-2-yl) | NMR Spectrum: (DMSO-d6 373K) 1.09 (t, 3H), 2.28 (s, 3H), 2.55 (m, 2H), 3.72 (s, 2H), 4.72 (br s, 2H), 6.64 (m, 1H), 6.82 (m, 1H), 6.98 (m, 1H), 7.27 (m, 1H), 8.00 (d, 2H), 8.14 (d, 2H), 8.27 (s, 1H), 8.89 (s, 1H), 9.49 (br s, 1H); Mass Spectrum: M + H$^+$ 386. | |
| 14 | [ethyl(2-methoxyethyl)amino]methyl-(3-cyano-pyridin-2-yl) | NMR Spectrum: (DMSO-d6 373K) 1.08 (t, 3H), 2.67 (q, 2H), 2.73 (t, 2H), 3.26 (s, 3H), 3.51 (t, 2H), 3.82 (s, 2H), 4.78 (br s, 2H), 6.63 (m, 1H), 6.84 (m, 1H), 6.99 (m, 1H), 7.30 (m, 1H), 8.02 (d, 2H), 8.18 (d, 2H), 8.29 (d, 1H), 8.90 (d, 1H), 9.54 (br s, 1H); Mass Spectrum: M + H$^+$ 430. | |
| 15 | [isopropyl(methyl)amino]methyl-(3-cyano-pyridin-2-yl) | NMR Spectrum: (DMSO-d6 373K) 1.09 (d, 6H), 2.21 (s, 3H), 2.92 (m, 1H), 3.72 (s, 2H), 4.77 (br s, 2H), 6.68 (m, 1H), 6.86 (m, 1H), 7.00 (m, 1H), 7.30 (m, 1H), 8.01 (d, 2H), 8.18 (d, 2H), 8.28 (s, 1H), 8.89 (s, 1H), 9.54 (br s, 1H); Mass Spectrum: M + H$^+$ 400. | |
| 16 | [methyl(propyl)amino]methyl-(3-cyano-pyridin-2-yl) | NMR Spectrum: (DMSO-d6 373K) 0.92 (t, 3H), 1.52 (m, 2H), 2.26 (s, 3H), 2.44 (t, 2H), 3.68 (s, 2H), 4.73 (br s, 2H), 6.64 (m, 1H), 6.82 (m, 1H), 6.99 (m, 1H), 7.28 (m, 1H), 8.00 (d, 2H), 8.14 (d, 2H), 8.23 (d, 1H), 8.88 (d, 1H), 9.50 (br s, 1H); Mass Spectrum: M + H$^+$ 400. | |

TABLE 3-continued

| Compound | X | Analytical Data | SM |
|---|---|---|---|
| 17 | (pyridine-piperazine-CH2-pyridine-CN structure) | NMR Spectrum: (DMSO-d6 373K) 2.66 (m, 4H), 3.72 (m, 4H), 3.74 (s, 2H), 4.72 (br s, 2H), 6.63 (m, 1H), 6.82 (m, 1H), 6.88 (m, 1H), 6.98 (m, 1H), 7.27 (m, 1H), 7.97 (m, 1H), 8.00 (d, 2H), 8.14 (d, 2H), 8.30 (d, 1H), 8.38 (m, 1H), 8.90 (d, 1H), 9.50 (br s, 1H); Mass Spectrum: M + H+ 515. | |

EXAMPLE 6

Using an analogous procedure to that described in Example 4, the appropriate amine starting material was reacted with N-(2-t-butoxycarbonylaminophenyl)-4-(3-cyano-5-formylpyridin-2-yl)benzamide to give the compounds shown in Table 4 below.

TABLE 4

| COMPOUND | R$^{1B}$ | ANALYTICAL DATA | SM |
|---|---|---|---|
| 1 | (4-methylpiperidinyl-CH2) | NMR SPECTRUM: (DMSO-D6) 0.89 (D, 3H), 1.15 (M, 2H), 1.32 (M, 1H), 1.58 (D, 2H), 2.00 (T, 2H), 2.79 (D, 2H), 3.59 (S, 2H), 4.94 (BR S, 2H), 6.60 (M, 1H), 6.78 (D, 1H), 6.98 (M, 1H), 7.19 (D, 1H), 7.98 (D, 2H), 8.14 (D, 2H), 8.30 (S, 1H), 8.86 (S, 1H), 9.77 (BR S, 1H); MASS SPECTRUM: M + H+ 426. | |
| 2 | (4-fluoropiperidinyl-CH2) | NMR SPECTRUM: (DMSO-D6 373K) 1.74 (M, 2H), 1.91 (M, 2H), 2.37 (M, 2H), 2.56 (M, 2H), 3.64 (S, 2H), 4.70 (M, 1H), 4.93 (BR S, 2H), 6.61 (M, 1H), 6.78 (M, 1H), 6.98 (M, 1H), 7.19 (D, 1H), 7.99 (D, 2H), 8.14 (D, 2H), 8.33 (D, 1H), 8.90 (S, 1H), 9.81 (BR S, 1H); MASS SPECTRUM: M + H+ 430. | |
| 3 | (4-hydroxypiperidinyl-CH2) | NMR SPECTRUM: (DMSO-D6) 1.42 (M, 2H), 1.73 (M, 2H), 2.15 (M, 2H), 2.71 (M, 2H), 3.49 (M, 1H), 3.62 (S, 2H), 4.55 (D, 1H), 4.95 (BR S, 2H), 6.61 (M, 1H), 6.80 (D, 1H), 7.00 (M, 1H), 7.21 (D, 1H), 8.00 (D, 2H), 8.15 (D, 2H), 8.32 (S, 1H), 8.88 (S, 1H), 9.78 (BR S, 1H); MASS SPECTRUM: M + H+ 428. | |

TABLE 4-continued

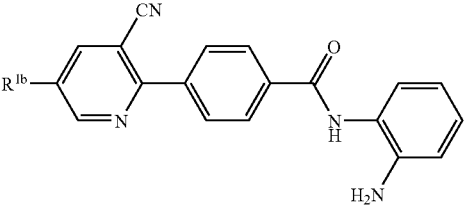

| COMPOUND | R<sup>1B</sup> | ANALYTICAL DATA | SM |
|---|---|---|---|
| 4 | 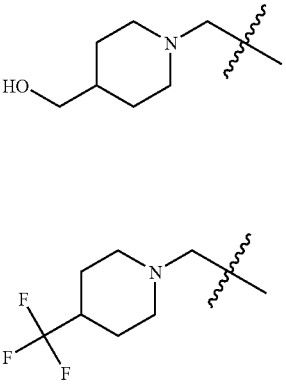 | NMR SPECTRUM: (DMSO-D6) 1.18 (M, 2H), 1.36 (M, 1H), 1.65 (D, 2H), 2.02 (M, 2H), 2.85 (D, 2H), 3.27 (M, 2H), 3.62 (S, 2H), 4.40 (M, 1H), 4.95 (BR S, 2H), 6.62 (M, 1H), 6.80 (D, 1H), 7.00 (M, 1H), 7.21 (D, 1H), 8.00 (D, 2H), 8.15 (D, 2H); 8.32 (S, 1H), 8.88 (S, 1H), 9.79 (BR S, 1H); MASS SPECTRUM: M + H$^+$ 442. | |
| 5 | 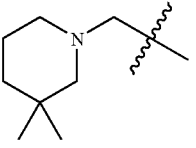 | NMR SPECTRUM: (DMSO-D6) 1.52 (M, 2H), 1.81 (D, 2H), 2.09 (T, 2H), 2.31 (M, 1H), 2.94 (D, 2H), 3.67 (S, 2H), 4.95 (BR S, 2H), 6.62 (M, 1H), 6.80 (M, 1H), 6.99 (M, 1H), 7.21 (D, 1H), 8.00 (D, 2H), 8.15 (D, 2H), 8.36 (D, 1H), 8.90 (D, 1H), 9.79 (D, 1H); MASS SPECTRUM: M + H$^+$ 480. | |
| 6 | 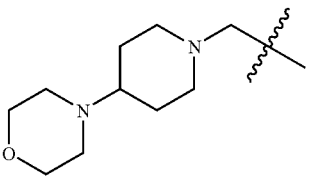 | NMR SPECTRUM: (DMSO-D6) 0.94 (S, 6H), 1.22 (M, 2H), 1.57 (M, 2H), 2.08 (M, 2H), 2.37 (M, 2H), 3.56 (S, 2H), 4.95 (BR S, 2H), 6.62 (M, 1H), 6.80 (D, 1H), 6.99 (M, 1H), 7.21 (D, 1H), 8.01 (D, 2H), 8.16 (D, 2H), 8.31 (S, 1H), 8.89 (S, 1H), 9.79 (BR S, 1H); MASS SPECTRUM: M + H$^+$ 440. | |
| 7 | 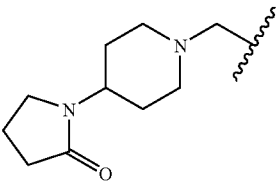 | NMR SPECTRUM: (DMSO-D6) 1.38-1.48 (M, 2H), 1.76 (D, 2H), 2.02 (T, 2H), 2.12 (M, 1H), 2.46 (M, 4H), 2.87 (D, 2H), 3.56 (M, 4H), 3.62 (S, 2H), 4.95 (BR S, 2H), 6.62 (M, 1H), 6.80 (M, 1H), 6.99 (M, 1H), 7.21 (D, 1H), 8.00 (D, 2H), 8.15 (D, 2H), 8.32 (D, 1H), 8.88 (D, 1H), 9.79 (BR S, 1H); MASS SPECTRUM: M + H$^+$ 497. | |
| 8 | 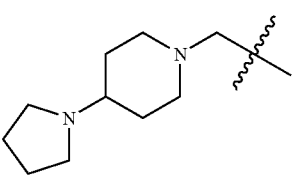 | NMR SPECTRUM: (DMSO-D6, 373K) 1.61 (M, 2H), 1.80 (M, 2H), 1.93 (M, 2H), 2.21 (T, 2H), 2.30 (M, 2H), 3.00 (M, 4H), 3.33 (T, 2H), 3.78 (M, 3H), 6.64 (M, 1H), 6.83 (M, 1H), 6.98 (M, 1H), 7.28 (D, 1H), 8.00 (D, 2H), 8.15 (D, 2H), 8.30 (D, 1H), 8.89 (D, 1H), 9.51 (BR S, 1H); MASS SPECTRUM: M + H$^+$ 495. | |
| 9 |  | NMR SPECTRUM: (DMSO-D6, 373K) 1.60 (M, 2H), 1.75 (M, 4H), 1.86 (M, 2H), 2.15 (DDD, 2H), 2.40 (M, 1H), 2.73 (M, 4H), 2.87 (M, 2H), 3.64 (S, 2H), 4.70 (BR S, 2H), 6.63 (M, 1H), 6.82 (M, 1H), 6.97 (M, 1H), 7.28 (D, 1H), 8.00 (M, 2H), 8.14 (D, 2H), 8.26 (D, 1H), 8.85 (D, 1H), 9.48 (BR S, 1H); MASS SPECTRUM: M + H$^+$ 481. | |

TABLE 4-continued

| COMPOUND | R$^{1B}$ | ANALYTICAL DATA | SM |
|---|---|---|---|
| 10 | (3S)-3-hydroxypiperidin-1-ylmethyl | NMR SPECTRUM: (DMSO-D6, 373K) 1.23 (M, 1H), 1.40 (M, 1H), 1.77 (M, 2H), 2.07 (M, 1H), 2.18 (M, 1H), 2.68 (M, 1H), 2.83 (M, 1H), 2.89 (M, 2H), 3.59 (M, 1H), 3.72 (BR S, 2H), 6.64 (M, 1H), 6.82 (M, 1H), 6.99 (M, 1H), 7.28 (D, 1H), 8.00 (D, 2H), 8.14 (D, 2H), 8.28 (D, 1H), 8.87 (D, 1H), 9.51 (BR S, 1H); MASS SPECTRUM: M + H$^+$ 428. | |
| 11 | (cyclobutylmethyl)(methyl)aminomethyl | NMR SPECTRUM: (DMSO-D6, 373K) 1.68 (M, 2H), 1.85 (M, 2H), 2.06 (M, 2H), 2.21 (S, 3H), 2.56 (M, 3H), 3.63 (S, 2H), 4.70 (BR S, 2H), 6.63 (M, 1H), 6.82 (M, 1H), 6.98 (M, 1H), 7.28 (M, 1H), 8.00 (M, 2H), 8.14 (D, 2H), 8.22 (D, 1H), 8.85 (D, 1H), 9.49 (BR S, 1H); MASS SPECTRUM: M + H$^+$ 426. | |
| 12 | 3-phenylpiperidin-1-ylmethyl | NMR SPECTRUM: (DMSO-D6, 373K) 1.53 (M, 1H), 1.77 (M, 2H), 1.91 (M, 1H), 2.34 (M, 1H), 2.95 (M, 4H), 3.81 (BR S, 2H), 6.63 (M, 1H), 6.82 (M, 1H), 6.98 (M, 1H), 7.19 (M, 1H), 7.28 (M, 5H), 8.00 (D, 2H), 8.14 (D, 2H), 8.33 (S, 1H), 8.92 (S, 1H), 9.51 (BR S, 1H); MASS SPECTRUM: M + H$^+$ 488. | |
| 13 | 4-phenylpiperidin-1-ylmethyl | NMR SPECTRUM: (DMSO-D6, 373K) 1.82 (M, 4H), 2.36 (M, 1H), 2.60 (M, 1H), 2.90 (M, 3H), 3.71 (S, 2H), 6.63 (M, 1H), 6.82 (M, 1H), 6.99 (M, 1H), 7.19 (M, 1H), 7.28 (M, 5H), 8.00 (D, 2H), 8.14 (D, 2H), 8.33 (S, 1H), 8.93 (S, 1H), 9.51 (BR S, 1H); MASS SPECTRUM: M + H$^+$ 488. | |
| 14 | 4-(pyridin-4-yl)piperidin-1-ylmethyl | NMR SPECTRUM: (DMSO-D6, 373K) 1.78 (M, 4H), 2.26 (DDD, 2H), 2.59 (M, 1H), 2.96 (M, 2H), 3.72 (S, 2H), 6.64 (M, 1H), 6.82 (M, 1H), 6.99 (M, 1H), 7.27 (M, 3H), 8.00 (D, 2H), 8.14 (D, 2H), 8.28 (D, 1H), 8.47 (M, 2H), 8.91 (S, 1H), 9.50 (BR S, 1H); MASS SPECTRUM: M + H$^+$ 489. | |
| 15 | 3-(4-fluorophenyl)piperidin-1-ylmethyl | NMR SPECTRUM: (DMSO-D6, 373K) 1.47 (M, 1H), 1.73 (M, 2H), 1.88 (M, 1H), 2.25 (M, 2H), 2.89 (M, 3H), 3.75 (S, 2H), 6.63 (M, 1H), 6.82 (M, 1H), 6.99 (M, 1H), 7.07 (M, 2H), 7.29 (M, 3H), 8.00 (D, 2H), 8.14 (D, 2H), 8.30 (D, 1H), 8.90 (D, 1H), 9.51 (BR S, 1H); MASS SPECTRUM: M + H$^+$ 506. | |

TABLE 4-continued

| COMPOUND | $R^{1B}$ | ANALYTICAL DATA | SM |
|---|---|---|---|
| 16 | | NMR Spectrum: (DMSO-d6, 373K) 2.17 (s, 6H), 2.38 (t, 2H), 2.66 (t, 2H), 3.87 (s, 2H), 4.72 (br s, 2H), 6.63 (m, 1H), 6.82 (m, 1H), 6.98 (m, 1H), 7.27 (d, 1H), 7.99 (d, 2H), 8.13 (d, 2H), 8.29 (d, 1H), 8.87 (d, 1H), 9.50 (br s, 1H); Mass Spectrum: M + H⁺ 415. | |
| 17 | | NMR Spectrum: (DMSO-d6, 373K) 1.68 (m, 4H), 2.48 (m, 4H), 2.56 (t, 2H), 2.69 (t, 2H), 3.88 (s, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.29 (d, 1H), 8.87 (d, 1H), 9.50 (br s, 1H); Mass Spectrum: M + H⁺ 441. | |

EXAMPLE 7

N-(2-aminophenyl)-4-(3-cyano-6-methylpyridin-2-yl)benzamide

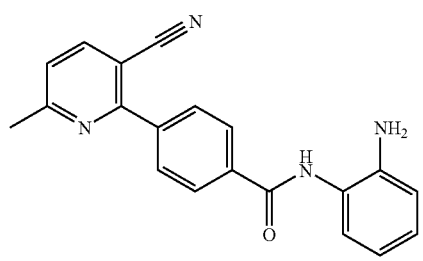

1,1'-bis(diphenylphosphino)ferrocenedichloropalladium (ii) chloride (32 mg, 0.044 mmol) was added to a mixture of n-(2-t-butoxycarbonylaminophenyl)-4-(4,4,5,5-tetramethyl-1,3,2-dioxaborolan-2-yl)benzamide (389 mg, 0.887 mmol; prepared as described in international patent publication number wo03/087057, method 13, page 60), 2-chloro-6-methyl-3-pyridinecarbonitrile (135 mg, 0.887 mmol) and saturated aqueous sodium hydrogen carbonate solution (2 ml) in 1,2-dimethoxyethane (4 ml). the mixture was heated in a microwave at 100° c. for 30 minutes. the mixture was allowed to cool, then partitioned between dichloromethane (30 ml) and water (20 ml). the aqueous layer was extracted with further dichloromethane (2×30 ml). combined organics were dried over magnesium sulfate then evaporated. the residue was purified by flash chromatography (eluting with 99:1→97:3 dichloromethane:methanol) to afford the title compound as a yellow gum which crystallised on trituration (80 mg, 27%).

Nmr spectrum: (cdcl₃) 2.72 (s, 3h), 3.88 (br s, 2h), 6.86 (m, 2h), 7.11 (m, 1h), 7.28 (d, 1h), 7.37 (d, 1h), 8.05 (m, 6h); mass spectrum: m+h+329.

EXAMPLE 8

N-(2-aminophenyl)-4-{3-cyano-5-[(4-isopropylpiperazin-1-yl)methyl]pyridin-2-yl}benzamide

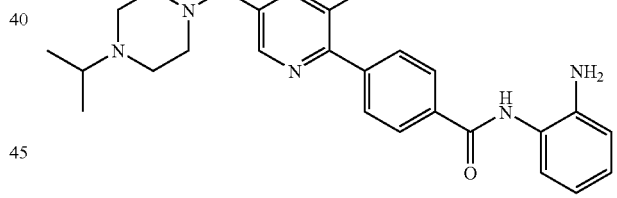

t-Butyl {2-[(4-{3-cyano-5-[(4-isopropylpiperazin-1-yl)methyl]pyridin-2-yl}benzoyl)amino]phenyl}carbamate (586 mg, 1.06 mmol; prepared as described in Method 19) was dissolved in ethyl acetate (7 ml) and 3M aqueous hydrochloric acid (7 ml) was added. The resulting suspension was stirred for 6 hours at ambient temperature then 3M aqueous hydrochloric acid (1.75 ml) added. The suspension was stirred for a further 2 hours then 3M aqueous hydrochloric acid (3.5 ml) was added and stirred for 30 minutes. The suspension was poured into water (50 ml) and washed with ethyl acetate (3×15 ml). The resulting aqueous solution was basified using a 2M aqueous solution of sodium hydroxide. A pale yellow precipitate crashed out which was filtered and washed with water. The pale yellow solid was dried in a vacuum oven at 50° C. ovenight (294 mg, 62%); NMR Spectrum: (CDCl₃) 0.99 (d, 6H), 2.48 (m, 8H), 2.60 (m, 1H) 3.56

(s, 2H), 3.79 (br s, 2H), 6.80 (m, 2H), 7.03 (m, 1H), 7.32 (d, 1H), 7.81 (br s, 1H), 7.99 (s, 4H), 8.04 (s, 1H), 8.74 (s, 1H); Mass Spectrum: M+H⁺ 455.

EXAMPLE 9

N-(2-aminophenyl)-4-{3-cyano-5-[(ethylamino)methyl]pyridin-2-yl}benzamide

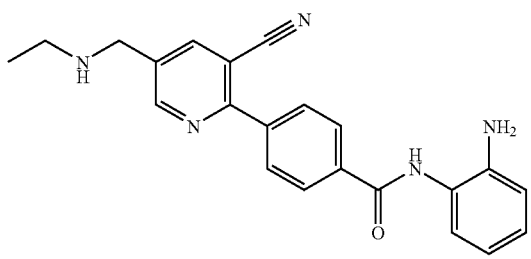

N-(2-t-Butoxycarbonylaminophenyl)-4-(3-cyano-5-formylpyridin-2-yl)benzamide (0.80 g, 1.8 mmol; prepared as described in Method 15 below) and ethylamine (1.4 ml of a 1.0M solution in THF, 1.4 mmol) were dissolved in dichloromethane (15 ml). Titanium (IV) isopropoxide (1.55 g, 1.62 ml, 5.4 mmol) was added and the mixture stirred at ambient temperature for 1 hour. Sodium borohydride (342 mg) and methanol (3 ml) were then added and the mixture stirred for a further 30 minutes. Water (20 ml) then a saturated aqueous sodium bicarbonate solution (30 ml) was added and the product extracted with dichloromethane (3×30 ml). The organic residues were concentrated and the residue purified using flash column chromatography eluting with ethyl acetate, followed by 2M NH₃/MeOH (3-5%) in ethyl acetate to give t-butyl {2-[(4-{3-cyano-5-[(ethylamino)methyl]pyridin-2-yl}benzoyl)amino]phenyl}carbamate (508 mg) as a white solid. This was dissolved in methanol (4 ml), a 4M solution of hydrogen chloride in 1,4-dioxan (10 ml, 40 mmol) was added and the solution then stirred at ambient temperature for 2 hours. The solvent was evaporated, methanol (5 ml) was added and the resulting solution was absorbed onto an SCX-2 column, which was washed with methanol (2 column volumes) and then eluted with a 2M solution of ammonia in methanol (2 column volumes) to give the product as a foam. This was re-precipitated by stirring in diethyl ether (20 ml) to give the title compound as a white solid (359 mg, 53%); NMR Spectrum: (DMSO-d₆ 373K) 1.08 (t, 3H), 2.62 (q, 2H), 3.67 (s, 2H), 4.73 (br s, 2H), 6.63 (m, 1H), 6.82 (m, 1H), 6.98 (m, 1H), 7.27 (m, 1H), 7.99 (d, 2H), 8.13 (d, 2H), 8.28 (d, 1H), 8.88 (d, 1H), 9.50 (br s, 1H); Mass Spectrum: M+H⁺ 372.

EXAMPLE 10

Using an analogous procedure to that described in example 1, the appropriate n-(2-t-butoxycarbonylaminophenyl)-4-(3-cyanopyridin-2-yl)benzamide starting material was reacted to give the compounds shown in table 5 below.

TABLE 5

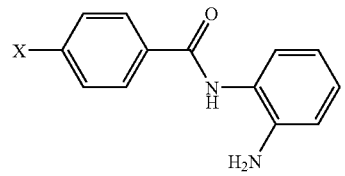

| Compound | X | Analytical Data | SM |
|---|---|---|---|
| 1 | ![structure with (S)-3-hydroxypyrrolidine] | NMR Spectrum: (DMSO-d₆) 1.57 (m, 1H), 2.01 (m, 1H), 2.38 (m, 1H), 2.44 (m, 1H), 2.63 (m, 1H), 2.72 (m, 1H), 3.71 (dd, 2H), 4.20 (m, 1H), 4.72 (d, 1H), 4.94 (br s, 2H), 6.60 (m, 1H), 6.78 (d, 1H), 6.98 (m, 1H), 7.19 (d, 1H), 7.98 (d, 2H), 8.13 (d, 2H), 8.34 (d, 1H), 8.88 (d, 1H), 9.78 (s, 1H); Mass Spectrum: M + H⁺ 414. | Method 23 |
| 2 | ![structure with (S)-3-fluoropyrrolidine] | NMR Spectrum: (DMSO-d₆) 1.90 (m, 1H), 2.16 (m, 1H), 2.40 (m, 1H), 2.75 (m, 3H), 3.77 (s, 2H), 4.94 (br s, 2H), 5.21 (m, 1H), 6.60 (m, 1H), 6.78 (d, 1H), 6.98 (m, 1H), 7.19 (d, 1H), 7.98 (d, 2H), 8.13 (d, 2H), 8.34 (d, 1H), 8.89 (d, 1H), 9.79 (s, 1H); Mass Spectrum: M + H⁺ 416. | Method 24 |

TABLE 5-continued

| Compound | X | Analytical Data | SM |
|---|---|---|---|
| 3 | [pyrrolidine with N-methyl substituent, CH2-linked to 3-cyano-pyridin-2-yl] | NMR Spectrum: (DMSO-d6) 0.84 (m, 1H), 1.16 (m, 1H), 1.57 (m, 1H), 2.01 (m, 1H), 2.29 (s, 3H), 2.43 (m, 1H), 2.66 (m, 2H), 3.73 (s, 2H), 4.93 (br s, 2H), 6.60 (m, 1H), 6.78 (d, 1H), 6.98 (m, 1H), 7.19 (d, 1H), 7.98 (d, 2H), 8.13 (d, 2H), 8.34 (d, 1H), 8.88 (d, 1H), 9.78 (s, 1H); Mass Spectrum: M + H+ 427. | Method 25 |
| 4 | [5-amino-6-methyl-3-cyanopyridin-2-yl] | NMR Spectrum: (DMSO-d6) 2.43 (s, 3H), 4.90 (br s, 2H), 5.79 (s, 2H), 6.60 (m, 1H), 6.79 (d, 1H), 6.98 (m, 1H), 7.19 (d, 1H), 7.31 (s, 1H), 7.86 (d, 2H), 8.06 (d, 2H), 9.70 (s, 1H); Mass Spectrum: M + H+ 344. | Method 26 |
| 5 | [5-(hydroxymethyl)-3-cyanopyridin-2-yl] | NMR Spectrum: (DMSO-d6) 4.67 (s, 2H), 4.96 (br s, 2H), 5.57 (br s, 1H), 6.61 (m, 1H), 6.80 (m, 1H), 6.99 (m, 1H), 7.20 (m, 1H), 8.00 (d, 2H), 8.14 (d, 2H), 8.33 (s, 1H), 8.91 (s, 1H), 9.78 (br s, 1H); Mass Spectrum: M + H+ 345. | Method 29 |
| 6 | [3-(diethylamino)pyrrolidin-1-yl-methyl linked to 3-cyanopyridin-2-yl] | NMR Spectrum: (DMSO-d6) 0.92 (t, 6H), 1.63 (m, 1H), 1.88 (m, 2H), 2.37 (m, 1H), 2.50 (m, 6H), 2.66 (m, 1H), 3.69 (m, 2H), 4.95 (br s, 2H), 6.60 (m, 1H), 6.78 (m, 1H), 6.98 (m, 1H), 7.19 (m, 1H), 7.98 (d, 2H), 8.14 (d, 2H), 8.31 (d, 1H), 8.87 (d, 1H), 9.78 (s, 1H); Mass Spectrum: M + H+ 469. | Method 14a |
| 7 | [N-butyl-N-methylaminomethyl linked to 3-cyanopyridin-2-yl] | NMR Spectrum: (DMSO-d6) 0.87 (t, 3H), 1.30 (m, 2H), 1.46 (m, 2H), 2.16 (s, 3H), 2.38 (t, 2H), 3.60 (s, 2H), 4.96 (br s, 2H), 6.60 (m, 1H), 6.79 (m, 1H), 6.98 (m, 1H), 7.19 (m, 1H), 7.98 (d, 2H), 8.14 (d, 2H), 8.30 (d, 1H), 8.86 (d, 1H), 9.79 (s, 1H); Mass Spectrum: M + H+ 414. | Method 14a |
| 8 | [(1,3-dimethyl-1H-pyrazol-5-yl)methyl-N-methylaminomethyl linked to 3-cyanopyridin-2-yl] | NMR Spectrum: (DMSO-d6) 2.09 (s, 3H), 2.69 (br s, 1H), 3.56 (s, 2H), 3.63 (s, 3H), 3.80 (s, 2H), 4.95 (br s, 2H), 5.97 (s, 1H), 6.60 (m, 1H), 6.80 (d, 1H), 7.00 (m, 1H), 7.20 (d, 1H), 7.98 (d, 2H), 8.13 (d, 2H), 8.32 (s, 1H), 8.90 (s, 1H), 9.78 (br s, 1H); Mass Spectrum: M + H+ 452. | Method 14c |

TABLE 5-continued

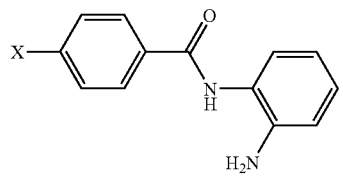

| Compound | X | Analytical Data | SM |
|---|---|---|---|
| 9 | (3,5-dimethylpyrazol-4-yl-ethyl)aminomethyl-cyanopyridinyl | NMR Spectrum: (DMSO-$d_6$) 2.07 (s, 6H), 2.50 (m, 6H), 3.84 (s, 2H), 4.93 (br s, 2H), 6.60 (m, 1H), 4.93 (br s, 2H), 7.00 (m, 1H), 7.20 (d, 1H), 7.97 (d, 2H), 8.14 (d, 2H), 8.32 (d, 1H), 8.89 (d, 1H), 9.78 (br s, 1H); Mass Spectrum: M + H$^+$ 466. | Method 14d |
| 10 | 3,5-dicyanopyridin-2-yl | NMR Spectrum: (DMSO-$d_6$) 4.95 (br s, 2H), 6.60 (m, 1H), 6.80 (d, 1H), 7.00 (m, 1H), 7.20 (d, 1H), 8.04 (d, 2H), 8.18 (d, 2H), 9.12 (d, 1H), 9.40 (d, 1H), 9.80 (br s, 1H); Mass Spectrum: M + H$^+$ 340. | Method 8 |

EXAMPLE 11

Using an analogous procedure to that described in Example 4, the appropriate amine starting material was reacted with N-(2-t-butoxycarbonylaminophenyl)-4-(3-cyano-5-formylpyridin-2-yl)benzamide to give the compounds shown in Table 6 below.

TABLE 6

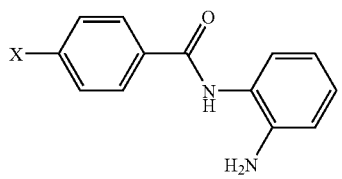

| Compound | X | Analytical Data | SM |
|---|---|---|---|
| 1 | (7-azabicyclo[2.2.1]heptan-7-yl)methyl-cyanopyridinyl | NMR Spectrum: (DMSO-$d_6$ 373K) 1.48 (m, 4H), 1.92 (m, 4H), 3.49 (br s, 2H), 3.87 (br s, 2H), 4.75 (br s, 2H), 6.66 (m, 1H), 6.84 (m, 1H), 7.01 (m, 1H), 7.30 (m, 1H), 8.02 (d, 2H), 8.17 (d, 2H), 8.43 (br s, 1H), 9.01 (s, 1H), 9.53 (br s, 1H); Mass Spectrum: M + H$^+$ 424. | |
| 2 | (cyclopropylmethyl)aminomethyl-cyanopyridinyl | NMR Spectrum: (DMSO-$d_6$ 373K) 0.38 (m, 2H), 0.60 (m, 2H), 1.11 (m, 1H), 2.86 (d, 2H), 4.27 (s, 2H), 6.64 (m, 1H), 6.82 (m, 1H), 6.99 (m, 1H), 7.28 (m, 1H), 8.02 (d, 2H), 8.16 (d, 2H), 8.56 (d, 1H), 9.06 (d, 1H), 9.52 (br s, 1H); Mass Spectrum: M + H$^+$ 398. | |

TABLE 6-continued

| Compound | X | Analytical Data | SM |
|---|---|---|---|
| 3 | (quinuclidinylmethyl-cyanopyridyl group) | NMR Spectrum: (DMSO-d$_6$ 373K) 1.55 (m, 4H), 1.67 (m, 3H), 1.99 (m, 2H), 2.66 (m, 1H), 2.78 (m, 2H), 3.87 (s, 2H), 4.72 (br s, 2H), 6.63 (m, 1H), 6.82 (m, 1H), 6.98 (m, 1H), 7.27 (m, 1H), 8.00 (d, 2H), 8.13 (d, 2H), 8.28 (s, 1H), 8.91 (s, 1H), 9.50 (br s, 1H); Mass Spectrum: M + H$^+$ 438. | |
| 4 | (4-methylpiperazinyl-piperidinylmethyl-cyanopyridyl group) | NMR Spectrum: (DMSO-d$_6$ 373K) 1.53 (m, 2H), 1.79 (m, 2H), 2.12 (m, 2H), 2.32 (m, 4H), 2.62 (m, 8H), 2.91 (m, 2H), 3.66 (s, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.24 (d, 1H), 8.87 (d, 1H), 9.51 (br s, 1H); Mass Spectrum: M + H$^+$ 510. | |
| 5 | (diethylaminoethylaminomethyl-cyanopyridyl group) | NMR Spectrum: (DMSO-d$_6$ 373K) 0.97 (t, 6H), 2.52 (m, 6H), 2.65 (t, 2H), 3.89 (s, 2H), 4.73 (br s, 2H), 6.63 (m, 1H), 6.82 (m, 1H), 6.98 (m, 1H), 7.27 (m, 1H), 7.99 (d, 2H), 8.13 (d, 2H), 8.29 (d, 1H), 8.89 (d, 1H), 9.50 (br s, 1H); Mass Spectrum: M + H$^+$ 443. | |
| 6 | (piperidinylethylaminomethyl-cyanopyridyl group) | NMR Spectrum: (DMSO-d$_6$ 373K) 1.39 (m, 2H), 1.50 (m, 4H), 2.35 (m, 4H), 2.40 (t, 2H), 2.66 (t, 2H), 3.88 (s, 2H), 4.73 (br s, 2H), 6.63 (m, 1H), 6.82 (m, 1H), 6.98 (m, 1H), 7.27 (m, 1H), 7.99 (d, 2H), 8.13 (d, 2H), 8.28 (d, 1H), 8.89 (d, 1H), 9.50 (br s, 1H); Mass Spectrum: M + H$^+$ 455. | |
| 7 | (dimethylaminoethyl-methylaminomethyl-cyanopyridyl group) | NMR Spectrum: (DMSO-d$_6$ 373K) 2.20 (s, 6H), 2.27 (s, 3H), 2.46 (t, 2H), 2.58 (t, 2H), 3.70 (s, 2H), 4.72 (br s, 2H), 6.63 (m, 1H), 6.82 (m, 1H), 6.98 (m, 1H), 7.28 (m, 1H), 8.00 (d, 2H), 8.14 (d, 2H), 8.26 (d, 1H), 8.87 (d, 1H), 9.50 (br s, 1H); Mass Spectrum: M + H$^+$ 429. | |
| 8 | (hydroxyethyl-methylaminomethyl-cyanopyridyl group) | NMR Spectrum: (DMSO-d$_6$ 373K) 2.29 (s, 3H), 2.61 (t, 2H), 3.59 (t, 2H), 3.75 (s, 2H), 4.11 (br s, 1H), 4.73 (br s, 2H), 6.63 (m, 1H), 6.82 (m, 1H), 6.98 (m, 1H), 7.28 (m, 1H), 8.00 (d, 2H), 8.13 (d, 2H), 8.30 (d, 1H), 8.89 (d, 1H), 9.50 (br s, 1H); Mass Spectrum: M + H$^+$ 402. | |

TABLE 6-continued

| Compound | X | Analytical Data | SM |
|---|---|---|---|
| 9 | ethylsulfonyl-piperazinyl-methyl-pyridine-CN | NMR Spectrum: (DMSO-d$_6$ 373K) 1.26 (t, 3H), 2.57 (m, 4H), 3.06 (q, 2H), 3.26 (m, 4H), 3.74 (s, 2H), 6.63 (m, 1H), 6.82 (m, 1H), 6.98 (m, 1H), 7.27 (m, 1H), 8.00 (d, 2H), 8.13 (d, 2H), 8.28 (d, 1H), 8.89 (d, 1H), 9.50 (br s, 1H); Mass Spectrum: M + H$^+$ 505. | |
| 10 | diethylamino-ethyl-methylamino-methyl-pyridine-CN | NMR Spectrum: (DMSO-d$_6$ 373K) 0.97 (t, 6H), 2.28 (s, 3H), 2.55 (m, 8H), 3.70 (s, 2H), 4.72 (br s, 2H), 6.63 (m, 1H), 6.82 (m, 1H), 6.98 (m, 1H), 7.27 (m, 1H), 8.00 (d, 2H), 8.13 (d, 2H), 8.27 (d, 1H), 8.87 (d, 1H), 9.50 (br s, 1H); Mass Spectrum: M + H$^+$ 457. | |
| 11 | dimethylamino-methylpropyl-amino-methyl-pyridine-CN | NMR Spectrum: (DMSO-d$_6$ 373K) 1.03 (d, 3H), 2.11 (m, 1H), 2.18 (s, 6H), 2.30 (m, 1H), 2.76 (m, 1H), 3.91 (d, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.30 (d, 1H), 8.89 (d, 1H), 9.50 (br s, 1H); Mass Spectrum: M + H$^+$ 429. | |
| 12 | methylsulfonyl-piperazinyl-methyl-pyridine-CN | NMR Spectrum: (DMSO-d$_6$ 373K) 2.55 (m, 4H), 2.87 (s, 3H), 3.14 (m, 4H), 3.74 (s, 2H), 6.63 (m, 1H), 6.82 (m, 1H), 6.98 (m, 1H), 7.27 (m, 1H), 7.99 (d, 2H), 8.13 (d, 2H), 8.28 (d, 1H), 8.87 (d, 1H), 9.50 (br s, 1H); Mass Spectrum: M + H$^+$ 491. | |
| 13 | 2-methyl-indol-3-yl-ethyl-amino-methyl-pyridine-CN | NMR Spectrum: (DMSO-d$_6$ 373K) 2.36 (s, 3H), 2.84 (m, 4H), 3.90 (s, 2H), 4.72 (br s, 2H), 6.63 (m, 1H), 6.82 (m, 1H), 6.94 (m, 3H), 7.23 (m, 1H), 7.28 (m, 1H), 7.40 (m, 1H), 7.98 (d, 2H), 8.13 (d, 2H), 8.23 (d, 1H), 8.85 (d, 1H), 9.50 (br s, 1H); Mass Spectrum: M + H$^+$ 501. | |
| 14 | allyl-piperazinyl-methyl-pyridine-CN | NMR Spectrum: (DMSO-d$_6$ 373K) 2.50 (m, 8H), 3.04 (m, 2H), 3.68 (s, 2H), 4.72 (br s, 2H), 5.20 (m, 2H), 5.83 (m, 1H), 6.64 (m, 1H), 6.82 (m, 1H), 6.98 (m, 1H), 7.27 (m, 1H), 7.99 (d, 2H), 8.13 (d, 2H), 8.24 (d, 1H), 8.87 (d, 1H), 9.50 (br s, 1H); Mass Spectrum: M + H$^+$ 453. | |
| 15 | methoxyethyl-piperazinyl-methyl-pyridine-CN | NMR Spectrum: (DMSO-d$_6$ 373K) 2.50 (m, 10H), 3.26 (s, 3H), 3.47 (t, 2H), 3.66 (s, 2H), 4.72 (br s, 2H), 6.64 (m, 1H), 6.82 (m, 1H), 6.98 (m, 1H), 7.27 (m, 1H), 7.99 (d, 2H), 8.13 (d, 2H), 8.24 (d, 1H), 8.86 (d, 1H), 9.50 (br s, 1H); Mass Spectrum: M + H$^+$ 471. | |

TABLE 6-continued

| Compound | X | Analytical Data | SM |
|---|---|---|---|
| 16 | (dimethylaminoethyl-piperazinyl-methyl-cyanopyridinyl) | NMR Spectrum: (DMSO-d₆ 373K) 2.22 (s, 6H), 2.43 (s, 4H), 2.50 (m, 8H), 3.63 (s, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.24 (d, 1H), 8.87 (d, 1H), 9.49 (br s, 1H); Mass Spectrum: M + H⁺ 484. | |
| 17 | (pyridin-2-yl-piperazinyl-methyl-cyanopyridinyl) | NMR Spectrum: (DMSO-d₆ 373K) 2.58 (m, 4H), 3.56 (m, 4H), 3.72 (s, 2H), 4.73 (br s, 2H), 6.62 (m, 2H), 6.77 (d, 1H), 6.82 (m, 1H), 6.98 (m, 1H), 7.27 (m, 1H), 7.50 (m, 1H), 8.00 (d, 2H), 8.10 (m, 1H), 8.14 (d, 2H), 8.30 (d, 1H), 8.90 (d, 1H), 9.50 (br s, 1H); Mass Spectrum: M + H⁺ 490. | |
| 18 | (pyrimidin-2-yl-piperazinyl-methyl-cyanopyridinyl) | NMR Spectrum: (DMSO-d₆ 373K) 2.57 (m, 4H), 3.72 (s, 2H), 3.80 (m, 4H), 4.72 (br s, 2H), 6.59 (m, 1H), 6.62 (m, 1H), 6.82 (m, 1H), 6.98 (m, 1H), 7.27 (m, 1H), 8.00 (d, 2H), 8.14 (d, 2H), 8.30 (d, 1H), 8.33 (d, 2H), 8.90 (d, 1H), 9.50 (br s, 1H); Mass Spectrum: M + H⁺ 491. | |
| 19 | (pyrazin-2-yl-piperazinyl-methyl-cyanopyridinyl) | NMR Spectrum: (DMSO-d₆ 373K) 2.61 (m, 4H), 3.63 (m, 4H), 3.73 (s, 2H), 4.72 (br s, 2H), 6.64 (m, 1H), 6.82 (m, 1H), 6.98 (m, 1H), 7.27 (m, 1H), 7.82 (d, 1H), 8.01 (d, 2H), 8.05 (m, 1H), 8.14 (d, 2H), 8.26 (d, 1H), 8.31 (d, 1H), 8.90 (d, 1H), 9.50 (br s, 1H); Mass Spectrum: M + H⁺ 491. | |
| 20 | (2-cyanophenyl-piperazinyl-methyl-cyanopyridinyl) | NMR Spectrum: (DMSO-d₆ 373K) 2.70 (m, 4H), 3.24 (m, 4H), 3.75 (s, 2H), 4.72 (br s, 2H), 6.64 (m, 1H), 6.82 (m, 1H), 6.88 (m, 1H), 7.07 (m, 1H), 7.17 (m, 1H), 7.27 (m, 1H), 7.57 (m, 1H), 7.63 (m, 1H), 8.00 (d, 2H), 8.14 (d, 2H), 8.31 (d, 1H), 8.91 (d, 1H), 9.50 (br s, 1H); Mass Spectrum: M + H⁺ 514. | |
| 21 | (3-cyanopyrazin-2-yl-piperazinyl-methyl-cyanopyridinyl) | NMR Spectrum: (DMSO-d₆ 373K) 2.68 (m, 4H), 3.76 (s, 2H), 3.82 (m, 4H), 4.72 (br s, 2H), 6.63 (m, 1H), 6.82 (m, 1H), 6.98 (m, 1H), 7.27 (m, 1H), 8.01 (d, 2H), 8.08 (m, 1H), 8.14 (d, 2H), 8.31 (d, 1H), 8.40 (d, 1H), 8.90 (d, 1H), 9.50 (br s, 1H); Mass Spectrum: M + H⁺ 516. | |

TABLE 6-continued

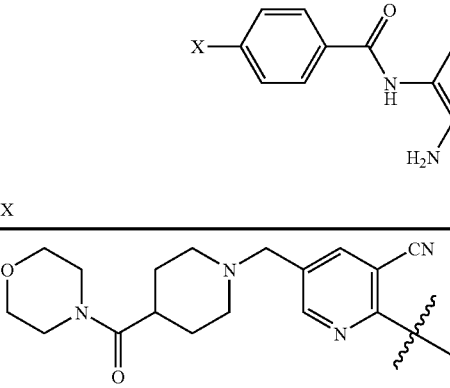

| Compound | X | Analytical Data | SM |
|---|---|---|---|
| 22 | 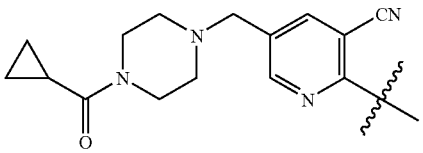 | NMR Spectrum: (DMSO-d$_6$ 373K) 1.70 (m, 4H), 2.27 (m, 2H), 2.44 (m, 1H), 2.63 (m, 1H), 3.48 (m, 4H), 3.57 (m, 4H), 3.72 (br s, 2H), 4.73 (br s, 2H), 6.63 (m, 1H), 6.82 (m, 1H), 6.98 (m, 1H), 7.27 (m, 1H), 8.00 (d, 2H), 8.14 (d, 2H), 8.28 (s, 1H), 8.87 (s, 1H), 9.51 (br s, 1H); Mass Spectrum: M + H$^+$ 525. | CAS 63214-57-3 WO2004018480 |
| 23 | 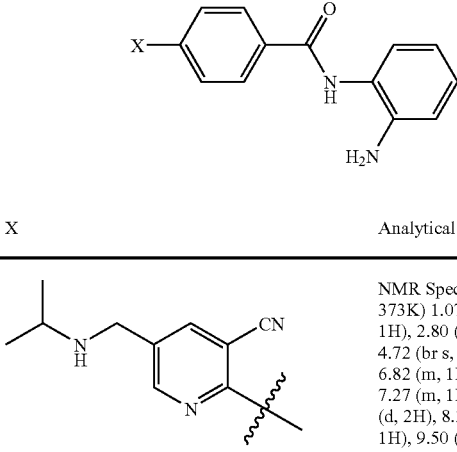 | NMR Spectrum: (DMSO-d$_6$ 373K) 0.69 (m, 2H), 0.76 (m, 2H), 1.89 (m, 1H), 2.95 (m, 4H), 3.60 (m, 4H), 3.71 (s, 2H), 4.71 (br s, 2H), 6.63 (m, 1H), 6.82 (m, 1H), 6.98 (m, 1H), 7.27 (m, 1H), 8.00 (d, 2H), 8.14 (d, 2H), 8.28 (d, 1H), 8.89 (d, 1H), 9.50 (br s, 1H); Mass Spectrum: M + H$^+$ 481. | |

EXAMPLE 12

Using an analogous procedure to that described in Example 9, the appropriate amine starting material was reacted with N-(2-t-butoxycarbonylaminophenyl)-4-(3-cyano-5-formylpyridin-2-yl)benzamide to give the compounds shown in Table 7 below.

TABLE 7

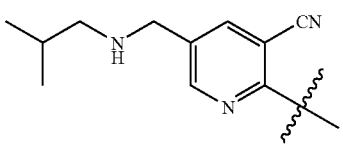

| Compound | X | Analytical Data | SM |
|---|---|---|---|
| 1 | (isopropylamino-methyl-pyridine structure) | NMR Spectrum: (DMSO-d$_6$ 373K) 1.07 (d, 6H), 2.06 (br s, 1H), 2.80 (m, 1H), 3.86 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.29 (d, 1H), 8.88 (d, 1H), 9.50 (br s, 1H); Mass Spectrum: M + H$^+$ 386. | |
| 2 | (isobutylamino-methyl-pyridine structure) | NMR Spectrum: (DMSO-d$_6$ 373K) 0.92 (d, 6H), 1.73 (m, 1H), 2.17 (br s, 1H), 2.42 (d, 2H), 3.86 (s, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.29 (d, 1H), 8.89 (d, 1H), 9.50 (br s, 1H); Mass Spectrum: M + H$^+$ 400. | |

TABLE 7-continued

| Compound | X | Analytical Data | SM |
|---|---|---|---|
| 3 | allyl-NH-CH2-(5-position of 3-cyano-pyridin-2-yl) | NMR Spectrum: (DMSO-d6 373K) 3.24 (m, 2H), 3.86 (s, 2H), 4.72 (br s, 2H), 5.08 (m, 1H), 5.21 (m, 1H), 5.90 (m, 1H), 6.63 (m, 1H), 6.82 (m, 1H), 6.98 (m, 1H), 7.27 (m, 1H), 7.99 (d, 2H), 8.13 (d, 2H), 8.29 (d, 1H), 8.89 (d, 1H), 9.50 (br s, 1H); Mass Spectrum: M + H+ 384. | |
| 4 | cyclopropyl-NH-CH2-(5-position of 3-cyano-pyridin-2-yl) | NMR Spectrum: (DMSO-d6 373K) 0.30 (m, 2H), 0.42 (m, 2H), 2.14 (m, 1H), 3.89 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.28 (d, 1H), 8.89 (d, 1H), 9.50 (br s, 1H); Mass Spectrum: M + H+ 384. | |
| 5 | cyclopentyl-NH-CH2-(5-position of 3-cyano-pyridin-2-yl) | NMR Spectrum: (DMSO-d6 373K) 1.40 (m, 2H), 1.51 (m, 2H), 1.67 (m, 2H), 1.77 (m, 2H), 2.14 (br s, 1H), 3.08 (m, 1H), 3.84 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.28 (d, 1H), 8.89 (d, 1H), 9.50 (br s, 1H); Mass Spectrum: M + H+ 412. | |
| 6 | (R)-sec-butyl-NH-CH2-(5-position of 3-cyano-pyridin-2-yl) | NMR Spectrum: (DMSO-d6 373K) 0.88 (t, 3H), 1.04 (d, 3H), 1.36 (m, 1H), 1.49 (m, 1H), 2.04 (br s, 1H), 2.59 (m, 1H), 3.88 (d, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.29 (d, 1H), 8.89 (d, 1H), 9.50 (br s, 1H); Mass Spectrum: M + H+ 400. | |
| 7 | (S)-sec-butyl-NH-CH2-(5-position of 3-cyano-pyridin-2-yl) | NMR Spectrum: (DMSO-d6 373K) 0.88 (t, 3H), 1.04 (d, 3H), 1.36 (m, 1H), 1.49 (m, 1H), 2.04 (br s, 1H), 2.59 (m, 1H), 3.88 (d, 2H), 4.72 (br s, 2H), 6.63 (m, 1H), 6.82 (m, 1H), 6.98 (m, 1H), 7.27 (m, 1H), 7.99 (d, 2H), 8.13 (d, 2H), 8.29 (d, 1H), 8.89 (d, 1H), 9.50 (br s, 1H); Mass Spectrum: M + H+ 400. | |

TABLE 7-continued

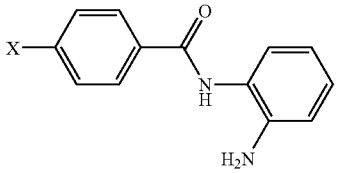

| Compound | X | Analytical Data | SM |
|---|---|---|---|
| 8 | 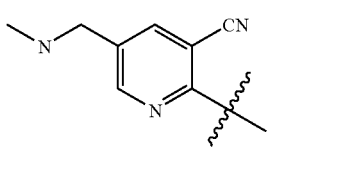 | NMR Spectrum: (DMSO-d$_6$ 373K) 2.37 (s, 3H), 3.81 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.27 (d, 1H), 8.87 (d, 1H), 9.50 (br s, 1H); Mass Spectrum: M + H$^+$ 358. | |
| 9 | 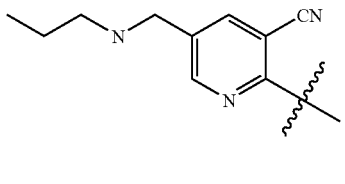 | NMR Spectrum: (DMSO-d$_6$ 373K) 0.91 (t, 3H), 1.50 (m, 2H), 2.57 (t, 2H), 3.87 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.28 (d, 1H), 8.88 (d, 1H), 9.50 (br s, 1H); Mass Spectnun: M + H$^+$ 384. | |
| 10 | 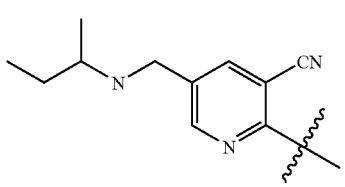 | NMR Spectrum: (DMSO-d$_6$ 373K) 0.92 (t, 3H), 1.39 (m, 2H), 1.49 (m, 2H), 2.60 (t, 2H), 3.87 (s, 2H), 4.72 (br s, 2H), 6.63 (m, 1H), 6.82 (m, 1H), 6.98 (m, 1H), 7.27 (m, 1H), 7.99 (m, 2H), 8.13 (m, 2H), 8.28 (d, 1H), 8.88 (d, 1H), 9.50 (br s, 1H); Mass Spectrum: M + H$^+$ 400. | |
| 11 | 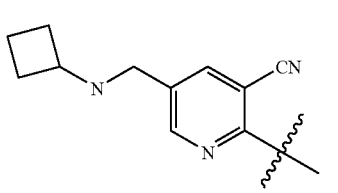 | NMR Spectrum: (DMSO-d$_6$ 373K) 0.91 (t, 3H), 1.08 (d, 3H), 1.37 (m, 1H), 1.52 (m, 1H), 2.62 (m, 1H), 3.89 (m, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.30 (d, 1H), 8.90 (d, 1H), 9.50 (br s, 1H); Mass Spectrum: M + H$^+$ 400. | |
| 12 | | NMR Spectrum: (DMSO-d$_6$ 373K) 1.73 (m, 4H), 2.23 (m, 2H), 3.30 (m, 1H), 3.82 (s, 2H), 4.72 (br s, 2H), 6.63 (m, 1H), 6.82 (m, 1H), 6.98 (m, 1H), 7.27 (m, 1H), 7.98 (d, 2H), 8.13 (d, 2H), 8.28 (d, 1H), 8.88 (d, 1H), 9.50 (br s, 1H); Mass Spectrum: M + H$^+$ 398. | |

EXAMPLE 13

Using an analogous procedure to that described in Example 9, the appropriate amine starting material was reacted with N-(2-t-butoxycarbonylaminophenyl)-4-(3-cyano-5-(1-oxo-ethyl)-6-methylpyridin-2-yl)benzamide prepared in Method 27 to give the compounds shown in Table 8 below.

TABLE 8

| Compound | X | Analytical Data | SM |
|---|---|---|---|
| 1 | (ethylamino-ethyl substituted pyridine) | NMR Spectrum: (DMSO-$d_6$ 373K) 1.05 (t, 3H), 1.33 (d, 3H), 2.43 (m, 1H), 2.55 (m, 1H), 2.69 (s, 3H), 4.08 (q, 1H), 4.72 (br s, 2H), 6.63 (m, 1H), 6.82 (m, 1H), 6.98 (m, 1H), 7.28 (m, 1H), 7.98 (d, 2H), 8.12 (d, 2H), 8.30 (s, 1H), 9.48 (br s, 1H); Mass Spectrum: M + H$^+$ 400. | Method 27 |
| 2 | (piperidinyl-ethyl substituted pyridine) | NMR Spectrum: (DMSO-$d_6$ 373K) 0.86 (m, 2H), 1.44 (m, 10H), 2.45 (m, 1H), 2.73 (s, 3H), 3.82 (m, 1H), 4.72 (br s, 2H), 6.63 (m, 1H), 6.82 (m, 1H), 6.98 (m, 1H), 7.28 (m, 1H), 8.00 (d, 2H), 8.12 (d, 2H), 8.19 (br s, 1H), 9.50 (br s, 1H); Mass Spectrum: M + H$^+$ 440. | Method 27 |
| 3* | OH (hydroxyethyl substituted pyridine) | NMR Spectrum: (DMSO-$d_6$) 1.42 (d, 3H), 2.66 (s, 3H), 4.72 (br s, 2H), 5.02 (q, 1H), 5.19 (br s, 1H), 6.63 (m, 1H), 6.82 (m, 1H), 6.98 (m, 1H), 7.27 (m, 1H), 7.98 (d, 2H), 8.12 (d, 2H), 8.24 (s, 1H), 9.48 (br s, 1H); Mass Spectrum: M + H$^+$ 373 | Method 27 |

*During the isolation of Example 13/2, Example 13/3 was isolated as a by-product.

EXAMPLE 14

N-(2-Aminophenyl)-4-(3-cyano-5-{[2-(ethylamino)ethoxy]methyl}pyridin-2-yl)benzamide

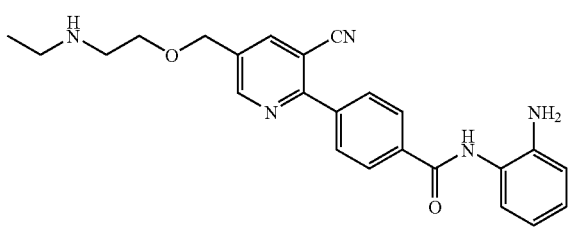

t-Butyl (2-{[4-(3-cyano-5-{[2-(ethylamino)ethoxy]methyl}pyridin-2-yl)benzoyl]amino}phenyl)carbamate (466 mg, 0.90 mmol, prepared as described in Method 28), 1,4-dioxane (3.4 ml) and a 4M solution of hydrogen chloride in 1,4-dioxane (3.4 ml) were stirred at ambient temperature for 4 hours.

The resulting precipitate was collected by filtration, washed with diethyl ether (3×) and dissolved in methanol. The solution was absorbed onto an SCX-2 column and the column washed with methanol (3 column volumes) and the product eluted with a 2M solution of ammonia in methanol (3 column volumes). The ammonia/methanol solution was concentrated under reduced pressure to give the title compound (320 mg, 86%); NMR Spectrum: (DMSO-$d_6$) 1.02 (t, 3H), 2.56 (m, 4H), 3.51 (m, 2H), 3.76 (s, 2H), 4.44 (m, 1H), 4.95 (br s, 1H), 6.62 (m, 1H), 6.80 (d, 1H), 7.00 (m, 1H), 7.22 (d, 1H), 8.00 (d, 2H), 8.16 (d, 2H), 8.39 (s, 1H), 8.92 (s, 1H), 9.78 (s, 1H); Mass Spectrum: M+H$^+$ 416.

EXAMPLE 15

N-(2-aminophenyl)-4-(3-cyano-5-{[2-(methylamino)ethoxy]methyl}pyridin-2-yl)benzamide

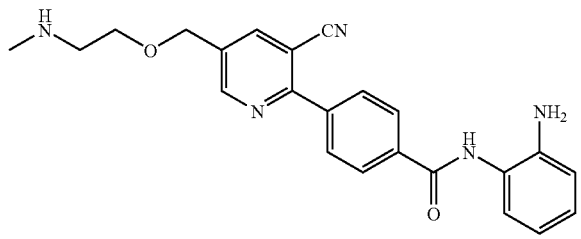

t-Butyl (2-{[4-(3-cyano-5-{[2-(methylamino)ethoxy]methyl}pyridin-2-yl)benzoyl]amino}phenyl)carbamate (465 mg, 0.93 mmol, prepared as described in Method 30), 1,4-dioxane (3.5 ml) and a 4M solution of hydrogen chloride in 1,4-dioxane (3.5 ml) were stirred at ambient temperature for 4 hours.

The resulting precipitate was collected by filtration, washed with diethyl ether (3×) and dissolved in methanol. The solution was absorbed onto an SCX-2 column and the column washed with methanol (3 column volumes) and eluted with a 2M solution of ammonia in methanol (3 column volumes). The ammonia/methanol solution was concentrated under reduced pressure and the residue purified by reverse phase HPLC. The product trifluoroacetate was re-dissolved in methanol and absorbed onto an SCX-2 column and the column washed with methanol (3 column volumes) and the product eluted with a 2M solution of ammonia in methanol (3 column volumes). The ammonia/methanol solution was concentrated under reduced pressure to give the title compound (200 mg, 54%); NMR Spectrum: (DMSO-$d_6$) 2.24 (s, 3H), 2.51 (m, 2H), 3.55 (m, 2H), 3.69 (s, 2H), 4.47 (m, 1H), 4.95 (br s, 2H), 6.62 (m, 1H), 6.81 (d, 1H), 6.99 (m, 1H), 7.21 (d, 1H), 8.01 (d, 2H), 8.15 (d, 2H), 8.40 (s, 1H), 8.91 (s, 1H), 9.79 (s, 1H); Mass Spectrum: M+H$^+$ 402.

EXAMPLE 16

N-(2-aminophenyl)-4-(3-cyano-5-{[2-(isopropylamino)ethoxy]methyl}pyridin-2-yl)benzamide

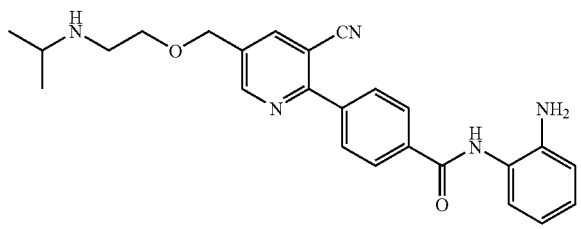

t-Butyl (2-{[4-(3-cyano-5-{[2-(isopropylamino)ethoxy]methyl}pyridin-2-yl)benzoyl]amino}phenyl)carbamate (170 mg, 0.32 mmol, prepared as described in Method 31), 1,4-dioxane (1.5 ml) and a 4M solution of hydrogen chloride in 1,4-dioxane (1.2 ml) were stirred at ambient temperature for 21 hours.

The resulting precipitate was collected by filtration, washed with diethyl ether (3×) and dissolved in methanol. The solution was absorbed onto an SCX-2 column and the column washed with methanol (3 column volumes). The product was eluted with a 2M solution of ammonia in methanol (3 column volumes). The ammonia/methanol solution was concentrated under reduced pressure and the residue purified by reverse phase HPLC. The isolated trifluoroacetate salt of the product was re-dissolved in methanol and absorbed onto an SCX-2 column and the column washed with methanol (3 column volumes) and the product eluted with a 2M solution of ammonia in methanol (3 column volumes). The ammonia/methanol solution was concentrated under reduced pressure to give the title compound (83 mg, 61%); NMR Spectrum: (DMSO-$d_6$) 1.03 (d, 6H), 2.55 (m, 2H), 2.93 (m, 1H), 3.41 (m, 2H), 3.75 (s, 2H), 4.39 (br s, 1H), 4.95 (br s, 2H), 6.62 (m, 1H), 6.80 (d, 1H), 6.99 (m, 1H), 7.21 (d, 1H), 8.00 (d, 2H), 8.15 (d, 2H), 8.41 (s, 1H), 8.94 (s, 1H), 9.78 (s, 1H); Mass Spectrum: M+H$^+$ 430.

EXAMPLE 17

N-(2-aminophenyl)-4-(3-cyano-5-{[(2-methoxy-1-methylethyl)amino]methyl}pyridin-2-yl)benzamide

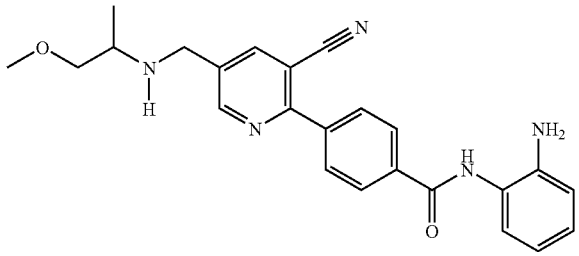

N-(2-t-Butoxycarbonylaminophenyl)-4-(3-cyano-5-formylpyridin-2-yl)benzamide (0.20 g, 0.45 mmol; prepared as described in Method 15 below) and 2-amino-1-methoxypropane (56 mg, 0.75 mmol) were dissolved in dichloromethane (5 ml). Titanium (IV) isopropoxide (0.27 ml, 0.90 mmol) was added and the mixture stirred at ambient temperature for 2 hours. Sodium borohydride (68 mg) and methanol (0.5 ml) were then added and the mixture stirred for a further 2 hours. The solution was absorbed onto an SCX-2 column and the product eluted with a 2M solution of ammonia in methanol. Concentration of the solvent gave the product as a gum. This was dissolved in dichloromethane (5 ml) and trifluoroacetic acid (1 ml) was added and the solution then stirred at ambient temperature for 4 hours. The resulting solution was absorbed onto an SCX-2 column which was washed with methanol (2 column volumes) and then the product eluted with a 2M solution of ammonia in methanol (2 column volumes) to give the product as a gum. This was stirred in diethyl ether to give the title compound as a white solid (66 mg, 57%). NMR Spectrum: (DMSO-$d_6$) 1.02 (d, 3H), 2.50 (br s, 1H), 2.82 (m, 1H), 3.24 (m, 2H), 3.26 (s, 3H), 3.91 (m, 2H), 4.95 (br s, 2H), 6.62 (m, 1H), 6.80 (d, 1H), 6.99 (m, 1H), 7.21 (d, 1H), 7.99 (d, 2H), 8.16 (d, 2H), 8.39 (s, 1H), 8.92 (s, 1H), 9.78 (s, 1H); Mass Spectrum: M+H$^+$ 416.

EXAMPLE 18

Using an analogous procedure to that described in Example 17, the appropriate amine starting material was reacted with N-(2-t-butoxycarbonylaminophenyl)-4-(3-cyano-5-formylpyridin-2-yl)benzamide prepared in Method 15 to give the compounds shown in Table 9 below.

TABLE 9

[Structure: X-C6H4-C(O)NH-C6H4-NH2 (4-X-benzamide with 2-aminophenyl)]

| Compound | X | Analytical Data | SM |
|---|---|---|---|
| 1 | [3-cyano-2-(substituted)pyridin-5-yl]methyl-NH-CH2CH2CH2-O-CH3 | NMR Spectrum: (DMSO-d$_6$) 1.68 (m, 2H), 2.51 (s, 1H), 2.57 (t, 2H), 3.23 (s, 3H), 3.40 (t, 2H), 3.84 (s, 2H), 4.95 (br s, 2H), 6.62 (m, 1H), 6.80 (d, 1H), 6.99 (m, 1H), 7.21 (d, 1H), 7.99 (d, 2H), 8.15 (d, 2H), 8.37 (s, 1H), 8.91 (s, 1H), 9.78 (s, 1H); Mass Spectrum: M + H$^+$ 416. | |
| 2 | (5-methylpyrazin-2-yl)methyl-NH-CH2-[3-cyanopyridin-5-yl] | NMR Spectrum: (DMSO-d$_6$); 2.48 (s, 3H), 3.57 (br s, 1H), 3.88 (s, 2H), 3.91 (s, 2H), 4.94 (br s, 2H), 6.62 (m, 1H), 6.80 (d, 1H), 6.99 (m, 1H), 7.21 (d, 1H), 7.99 (d, 2H), 8.16 (d, 2H), 8.40 (s, 1H), 8.47 (s, 1H), 8.59 (s, 1H), 8.92 (s, 1H), 9.79 (s, 1H); Mass Spectrum: M + H$^+$ 450. | |
| 3 | (2-methoxybenzyl)-NH-CH2-[3-cyanopyridin-5-yl] | NMR Spectrum: (DMSO-d$_6$); 2.85 (br m, 1H), 3.71 (s, 2H), 3.79 (s, 3H), 3.88 (s, 2H), 4.95 (br s, 2H), 6.62 (m, 1H), 6.80 (d, 1H), 6.96 (m, 1H), 7.23 (m, 3H), 7.37 (d, 1H), 7.99 (d, 2H), 8.16 (d, 2H), 8.38 (s, 1H), 8.92 (s, 1H), 9.78 (s, 1H); Mass Spectrum: M + H$^+$ 464. | |
| 4 | (3-methoxybenzyl)-NH-CH2-[3-cyanopyridin-5-yl] | NMR Spectrum: (DMSO-d$_6$); 3.76 (s, 5H), 3.87 (s, 2H), 4.95 (br s, 2H), 6.62 (m, 1H), 6.81 (m, 2H), 6.98 (m, 3H), 7.24 (m, 2H), 7.99 (d, 2H), 8.16 (d, 2H), 8.38 (s, 1H), 8.92 (s, 1H), 9.79 (s, 1H); Mass Spectrum: M + H$^+$ 464. | |
| 5 | isopropoxy-CH2CH2CH2-NH-CH2-[3-cyanopyridin-5-yl] | NMR Spectrum: (DMSO-d$_6$); 1.07 (d, 6H), 1.65 (m, 2H), 2.50 (br s, 1H), 2.57 (t, 2H), 3.42 (t, 2H), 3.50 (m, 1H), 3.84 (s, 2H), 4.95 (br s, 2H), 6.62 (m, 1H), 6.80 (d, 1H), 6.99 (m, 1H), 7.21 (d, 1H), 7.99 (d, 2H), 8.16 (d, 2H), 8.36 (s, 1H), 8.91 (s, 1H), 9.78 (s, 1H); Mass Spectrum: M + H$^+$ 444. | |
| 6 | (6-trifluoromethylpyridin-3-yl)methyl-NH-CH2-[3-cyanopyridin-5-yl] | NMR Spectrum: (DMSO-d$_6$); 3.27 (s, 1H), 3.88 (s, 2H), 3.89 (s, 2H), 4.95 (br s, 2H), 6.62 (m, 1H), 6.81 (d, 1H), 7.00 (m, 1H), 7.21 (d, 1H), 7.87 (d, 1H), 7.99 (d, 2H), 8.08 (d, 1H), 8.16 (d, 2H), 8.41 (s, 1H), 8.76 (s, 1H), 8.94 (s, 1H), 9.79 (s, 1H); Mass Spectrum: M + H$^+$ 503. | |

TABLE 9-continued

| Compound | X | Analytical Data | SM |
|---|---|---|---|
| 7 | (4-methylthiazol-2-ylmethyl)aminomethyl-pyridine | NMR Spectrum: (DMSO-d₆); 2.33 (s, 3H), 3.40 (br s, 1H), 3.93 (s, 2H), 3.99 (s, 2H), 4.95 (br s, 2H), 6.62 (m, 1H), 6.80 (d, 1H), 6.99 (m, 1H), 7.14 (s, 1H), 7.21 (d, 1H), 8.00 (d, 2H), 8.16 (d, 2H), 8.40 (s, 1H), 8.94 (s, 1H), 9.79 (s, 1H); Mass Spectrum: M + H⁺ 455. | |
| 8 | (1-methylimidazol-4-yl)ethylaminomethyl-pyridine | NMR Spectrum: (DMSO-d₆); 2.61 (t, 2H), 2.68 (br s, 1H), 2.75 (t, 2H), 3.58 (s, 3H), 3.87 (s, 2H), 4.95 (br s, 2H), 6.62 (m, 1H), 6.80 (d, 1H), 6.85 (s, 1H), 6.99 (m, 1H), 7.21 (d, 1H), 7.43 (s, 1H), 8.00 (d, 2H), 8.15 (d, 2H), 8.35 (s, 1H), 8.91 (s, 1H), 9.78 (s, 1H); Mass Spectrum: M + H⁺ 452. | |

EXAMPLE 19

N-(2-aminophenyl)-4-(3-cyano-5-{[(tetrahydro-2h-pyran-4-ylmethyl)amino]methyl}pyridin-2-yl)benzamide

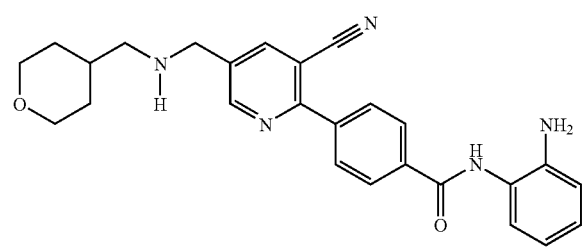

N-(2-t-Butoxycarbonylaminophenyl)-4-(3-cyano-5-formylpyridin-2-yl)benzamide (0.20 g, 0.45 mmol; prepared as described in Method 15 below) and 4-aminomethyltetrahydropyridine (81 mg, 0.7 mmol) were dissolved in dichloromethane (6 ml). Titanium (IV) isopropoxide (0.27 ml, 0.9 mmol) was added and the mixture stirred at ambient temperature for 2 hours. Sodium borohydride (70 mg) and methanol (0.6 ml) were then added and the mixture stirred for a further 16 hours. Water (4 ml) and a saturated aqueous sodium bicarbonate solution (2 ml) were added and stirred for 10 minutes. The product was extracted with dichloromethane (3×10 ml) and the organic residues concentrated. The residue was purified using chromatography eluting with 10% methanol in ethyl acetate, and concentration of the solvent gave product as a gum. This was dissolved in dichloromethane (6 ml), trifluoroacetic acid (1.2 ml) added and the solution then stirred at ambient temperature for 2 hours. The resulting solution was absorbed onto an SCX-2 column, which was washed with methanol (3 column volumes) and then the product eluted with a 2M solution of ammonia in methanol (3 column volumes) then concentrated to give the product as a gum. This was re-precipitated by stirring in diethyl ether (3 ml) to give the title compound as a foam (73 mg, 37%). NMR Spectrum: (DMSO-d₆) 1.18 (m, 2H), 1.66 (m, 3H), 2.46 (d, 2H), 3.29 (m, 2H), 3.85 (m, 4H), 4.95 (s, 2H), 6.62 (m, 1H), 6.80 (d, 1H), 7.00 (m, 1H), 7.21 (d, 1H), 8.00 (d, 2H), 8.16 (d, 2H), 8.39 (s, 1H), 8.39 (s, 1H), 9.78 (s, 1H); Mass Spectrum: M+H⁺ 442.

EXAMPLE 20

Using an analogous procedure to that described in Example 19, the appropriate amine starting material was reacted with N-(2-t-butoxycarbonylaminophenyl)-4-(3-cyano-5-formylpyridin-2-yl)benzamide prepared in Method 15 to give the compounds shown in Table 10 below.

TABLE 10

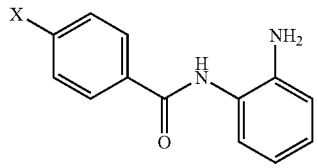

| Compound | X | Analytical Data | SM |
|---|---|---|---|
| 1 | (tetrahydropyran-4-ylaminomethyl-cyanopyridinyl) | NMR Spectrum: (DMSO-d₆) 1.37 (m, 2H), 1.87 (d, 2H), 2.81 (m, 1H), 3.31 (m, 2H), 3.88 (d, 2H), 4.00 (s, 2H), 4.95 (br s, 2H), 6.62 (m, 1H), 6.80 (d, 1H), 7.00 (m, 1H), 7.21 (d, 1H), 8.00 (d, 2H), 8.16 (d, 2H), 8.44 (s, 1H), 8.96 (s, 1H), 9.79 (s, 1H); Mass Spectrum: M + Na⁺ 450. | |
| 2 | (2-methoxy-2-methylpropylaminomethyl-cyanopyridinyl) | NMR Spectrum: (DMSO-d₆) 1.17 (s, 6H), 2.73 (br s, 2H), 3.13 (s, 3H), 4.08 (br s, 2H), 4.95 (br s, 2H), 6.62 (m, 1H), 6.81 (d, 1H), 7.00 (m, 1H), 7.21 (d, 1H), 8.01 (d, 2H), 8.17 (d, 2H), 8.49 (s, 1H), 8.99 (s, 1H), 9.80 (s, 1H); Mass Spectrum: M + H⁺ 430. | |

EXAMPLE 21

N-(2-aminophenyl)-4-(3-cyano-5-{[methyl(tetrahydrofuran-2-ylmethyl)amino]methyl}pyridin-2-yl)benzamide

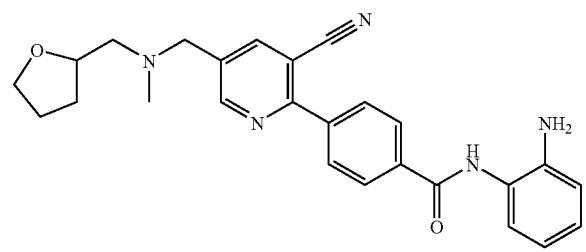

N-(2-t-Butoxycarbonylaminophenyl)-4-(3-cyano-5-formylpyridin-2-yl)benzamide (0.20 g, 0.45 mmol; prepared as described in Method 15 below), N-methyltetrahydrofurfurylamine (81 mg, 0.7 mmol) and acetic acid (26 µl, 0.45 mmol) were dissolved in tetrahydrofuran (5 ml). The mixture was stirred at ambient temperature for 1 hour. Sodium triacetoxyborohydride (144 mg, 0.7 mmol) was then added and the mixture stirred for a further 3 hours. The mixture was concentrated and the residue purified by flash chromatography eluting with 100% ethyl acetate. Concentration of the solvent gave product as a gum. This was dissolved in dichloromethane (6 ml), trifluoroacetic acid (1.2 ml) was added and the solution then stirred at ambient temperature for 2 hours. The resulting solution was absorbed onto an SCX-2 column, which was washed with methanol (3 column volumes) and the product eluted with a 2M solution of ammonia in methanol (3 column volumes) then concentrated to give the product as a gum. This was re-precipitated by stirring in diethyl ether (3 ml) to give the title compound as a foam/gum (43 mg, 22%). NMR Spectrum: (DMSO-d₆, 373K) ¹H NMR 1.53 (m, 1H), 1.82 (m, 2H), 1.98 (m, 1H), 2.37 (s, 3H), 2.64 (m, 2H), 3.00 (br s, 2H), 3.66 (q, 1H), 3.77 (q, 1H), 3.84 (m, 2H), 4.04 (m, 1H), 6.63 (m, 1H), 6.82 (d, 1H), 6.98 (m, 1H), 7.27 (d, 1H), 8.00 (d, 2H), 8.14 (d, 2H), 8.29 (s, 1H), 8.89 (s, 1H), 9.50 (br s, 1H); Mass Spectrum: M+H⁺ 442.

EXAMPLE 22

N-(2-aminophenyl)-4-(5-{[bis(2-methoxyethyl)amino]methyl}-3-cyanopyridin-2-yl)benzamide Using an analogous procedure to that described in Example 21, the appropriate amine starting material was reacted with N-(2-t-Butoxycarbonylaminophenyl)-4-(3-cyano-5-formylpyridin-2-yl)benzamide prepared in Method 15 to give the compound shown in Table 11 below.

TABLE 11

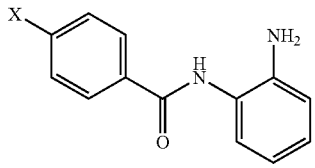

| Compound | X | Analytical Data | SM |
|---|---|---|---|
| 1 | 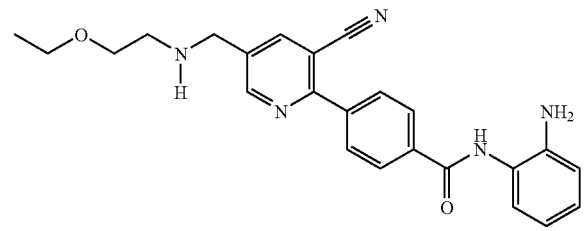 | NMR Spectrum: (DMSO-$d_6$, 373K) 2.83 (t, 4H), 3.26 (br m, 8H), 3.49 (t, 4H), 3.94 (s, 2H), 6.64 (m, 1H), 6.82 (m, 1H), 6.99 (m, 1H), 7.27 (m, 1H), 8.00 (d, 2H), 8.14 (d, 2H), 8.31 (d, 1H), 8.89 (d, 1H), 9.51 (br s, 1H); Mass Spectrum: M + H$^+$ 460. | |

EXAMPLE 23

N-(2-aminophenyl)-4-(3-cyano-5-{[(2-ethoxyethyl)amino]methyl}pyridin-2-yl)benzamide t-Butyl[2-({4-[3-cyano-5-(hydroxymethyl)pyridin-2-yl]benzoyl}amino)phenyl]carbamate (0.2 g, 0.45 mmol, prepared a described in Method 29) was dissolved with stirring in tetrahydrofuran (5 ml). N,N-Diisopropylethylamine (0.24 ml, 1.35 mmol) was added and the mixture cooled to 0° C. in an ice bath. Methanesulfonyl chloride (46 µl, 0.6 mmol) was added and the solution stirred for 30 minutes at low temperature to form the mesylate.

The mixture was allowed to warm to ambient temperature and a solution of 2-ethoxyethylamine (625 mg, 7.0 mmol) in tetrahydrofuran (2 ml) was added. The mixture was then stirred at ambient temperature for 16 hours. The solution was concentrated under reduced pressure and the residue purified by flash chromatography eluting with 10% methanol/ethyl acetate to give product as a gum.

The residue was dissolved in dichloromethane (6 ml) and trifluoroacetic acid (1.2 ml) added then the solution then stirred at ambient temperature for 2 hours. The resulting solution was absorbed onto an SCX-2 column, which was washed with methanol (3 column volumes) and the product eluted with a 2M solution of ammonia in methanol (3 column volumes) then concentrated to give the product as a gum. The gum was re-precipitated by stirring in diethyl ether (3 ml) to give the title compound as a solid (86 mg, 46%). NMR Spectrum: (DMSO-$d_6$) 1.12 (t, 3H), 2.45 (br s, 1H), 2.68 (t, 2H), 3.44 (m, 4H), 3.87 (s, 2H), 4.95 (s, 2H), 6.62 (m, 1H), 6.80 (d, 1H), 6.99 (m, 1H), 7.21 (d, 1H), 7.99 (d, 2H), 8.16 (d, 2H), 8.38 (s, 1H), 8.91 (s, 1H), 9.78 (s, 1H); Mass Spectrum: M+H$^+$ 416.

EXAMPLE 24

Using an analogous procedure to that described in Example 23, the appropriate amine starting material was reacted with t-butyl[2-({4-[3-cyano-5-(hydroxymethyl)pyridin-2-yl]benzoyl}amino)phenyl]carbamate (0.2 g, 0.45 mmol, prepared as described in Method 29) to give the compounds shown in Table 12 below.

TABLE 12

[Structure: X-C6H4-C(=O)-NH-C6H4-NH2 (ortho-amino)]

| Compound | X | Analytical Data | SM |
|---|---|---|---|
| 1 | [isopropoxy-ethyl-NH-CH2-pyridine(CN)-yl] | NMR Spectrum: (DMSO-d$_6$) 1.10 (d, 6H), 2.68 (t, 2H), 3.46 (t, 2H), 3.55 (m, 1H), 3.89 (s, 2H), 4.95 (s, 2H), 6.62 (m, 1H), 6.80 (d, 1H), 6.99 (m, 1H), 7.21 (d, 1H), 7.99 (d, 2H), 8.16 (d, 2H), 8.39 (d, 1H), 8.92 (d, 1H), 9.78 (s, 1H); Mass Spectrum: M + H$^+$ 430. | |
| 2 | [ethoxy-propyl-NH-CH2-pyridine(CN)-yl] | NMR Spectrum: (DMSO-d$_6$) 1.10 (t, 3H), 1.68 (m, 2H), 2.58 (t, 2H), 2.63 (br s, 1H), 3.41 (m, 4H), 3.85 (s, 2H), 4.95 (s, 2H), 6.62 (m, 1H), 6.80 (d, 1H), 6.99 (m, 1H), 7.21 (d, 1H), 7.99 (d, 2H), 8.16 (d, 2H), 8.37 (d, 1H), 8.92 (d, 1H), 9.78 (s, 1H); Mass Spectrum: M + H$^+$ 430. | |
| 3 | [propoxy-ethyl-NH-CH2-pyridine(CN)-yl] | NMR Spectrum: (DMSO-d$_6$) 0.88 (t, 3H), 1.52 (m, 2H), 2.55 (br s, 1H), 2.70 (t, 2H), 3.34 (t, 2H), 3.47 (t, 2H), 3.89 (s, 2H), 4.95 (s, 2H), 6.62 (m, 1H), 6.80 (d, 1H), 6.99 (m, 1H), 7.21 (d, 1H), 7.99 (d, 2H), 8.16 (d, 2H), 8.38 (d, 1H), 8.92 (d, 1H), 9.78 (s, 1H); Mass Spectrum: M + H$^+$ 430. | |
| 4 | [tetrahydrofuran-2-yl-methyl-NH-CH2-pyridine(CN)-yl] | NMR Spectrum: (DMSO-d$_6$) 1.55 (m, 1H), 1.81 (m, 2H), 1.93 (m, 1H), 2.60 (d, 2H), 3.63 (m, 1H), 3.76 (m, 1H), 3.91 (m, 3H), 4.95 (br s, 2H), 6.62 (m, 1H), 6.80 (d, 1H), 6.99 (m, 1H), 7.21 (d, 1H), 8.00 (d, 2H), 8.16 (d, 2H), 8.39 (s, 1H), 8.92 (s, 1H), 9.78 (s, 1H); Mass Spectrum: M + H$^+$ 428. | |
| 5 | [(5-methylfuran-2-yl)methyl-NH-CH2-pyridine(CN)-yl] | NMR Spectrum: (DMSO-d$_6$) 2.22 (s, 3H), 2.97 (br s, 1H), 3.67 (s, 2H), 3.85 (s, 2H), 4.95 (s, 2H), 5.96 (m, 1H), 6.12 (d, 1H), 6.62 (m, 1H), 6.80 (d, 1H), 6.99 (m, 1H), 7.21 (d, 1H), 7.98 (d, 2H), 8.16 (d, 2H), 8.34 (d, 1H), 8.89 (d, 1H), 9.78 (s, 1H); Mass Spectrum: M + H$^+$ 438. | |

Method Section

Method 1

N-(2-t-butoxycarbonylaminophenyl)-4-(3-cyanopyridin-2-yl)benzamide

N-(2-t-butoxycarbonylaminophenyl)-4-(4,4,5,5-tetramethyl-1,3,2-dioxaborolan-2-yl)benzamide (400 mg, 0.913 mmol; prepared as described in international patent publication number wo03/087057, method 13, page 60), 2-bromonicotinonitrile (167 mg, 0.913 mmol), tetrakis(triphenylphosphine)palladium[0] (50 mg, 0.043 mmol), 1,2-dimethoxyethane (4 ml) and a saturated aqueous solution of sodium hydrogen carbonate (2 ml) were stirred at 100° c. under an atmosphere of nitrogen in a microwave for 130 mins. the mixture was allowed to cool before being partitioned between dichloromethane and water. the organics were separated, dried over sodium sulfate, filtered and evaporated. the crude product was purified by chromatography on silica eluting with 60:40 ethyl acetate: isohexane to afford the title compound as a white solid (214 mg, 57%); nmr spectrum: (dmso-d$_6$) 1.45 (s, 9h), 7.18 (m, 2h), 7.57 (m, 1h), 7.66 (dd, 1h), 8.01 (d, 2h), 8.13 (d, 2h), 8.47 (dd, 1h), 8.73 (s, 1h), 8.98 (d, 1h), 9.97 (s, 1h); mass spectrum: m+h+415.

Methods 2-7

Using an analogous procedure to that described in Method 1, the N-(2-t-butoxycarbonylaminophenyl)-4-(4,4,5,5-tetramethyl-1,3,2,-dioxaborolan-2-yl)benzamide starting material was reacted with the appropriate bromo- or choro-pyridine to give the compounds described in Table 13 below.

TABLE 13

| Method | X | Analytical Data | SM |
|---|---|---|---|
| 2 | | NMR Spectrum: (DMSO-d$_6$) 1.45 (s, 9H), 2.42 (s, 3H), 7.18 (m, 2H), 7.56 (m, 2H), 7.97 (d, 2H), 8.11 (d, 2H), 8.30 (d, 1H), 8.70 (s, 1H), 8.83 (d, 1H), 9.93 (s, 1H); Mass Spectrum: M + H$^+$ 429. | CAS 65996-18-1 Baldwin, JJ; et al. Journal of Organic Chemistry (1978), 43(12), 2529-35. |
| 3 | | NMR Spectrum: (DMSO-d$_6$) 1.45 (s, 9H), 3.23 (s, 6H), 6.91 (d, 1H), 7.17 (m, 2H), 7.55 (m, 2H), 7.89 (d, 2H), 8.05 (d, 2H), 8.34 (d, 1H), 8.67 (s, 1H), 9.91 (s, 1H); Mass Spectrum: M + H$^+$ 458. | |
| 4 | | NMR Spectrum: (DMSO-d$_6$) 1.15 (t, 3H), 1.45 (s, 9H), 2.35 (s, 3H), 3.35 (m, 2H), 6.46 (s, 1H), 7.17 (m, 2H), 7.56 (m, 3H), 7.90 (d, 2H), 8.05 (d, 2H), 8.67 (s, 1H), 9.89 (s, 1H); Mass Spectrum: M + H$^+$ 472. | CAS 51561-60-5 Lamm, Gunther; et al. Ger Offen (1993), DE4142192 |
| 5 | | NMR Spectrum: (DMSO-d$_6$) 1.45 (s, 9H), 2.36 (s, 3H), 3.44 (m, 2H), 3.55 (m, 2H), 4.70 (t, 1H), 6.51 (s, 1H), 7.17 (m, 2H), 7.56 (m, 3H), 7.90 (d, 2H), 8.05 (d, 2H), 8.67 (s, 1H), 9.89 (s, 1H); Mass Spectrum: M + H$^+$ 488. | CAS 56331-50-1 Lamm, Gunther; et al. Brit (1975) GB1405308. |
| 6 | | NMR Spectrum: (DMSO-d$_6$) 1.45 (s, 9H), 2.54 (s, 3H), 2.59 (s, 3H), 7.17 (m, 2H), 7.45 (s, 1H), 7.56 (m, 2H), 7.95 (d, 2H), 8.10 (d, 2H), 8.68 (s, 1H), 9.93 (s, 1H); Mass Spectrum: M + Na$^+$ 465. | |

TABLE 13-continued

| Method | X | Analytical Data | SM |
|---|---|---|---|
| 7 | (structure: 4-methyl-6-(4-methylpiperazin-1-yl)-3-cyanopyridin-2-yl) | NMR Spectrum: (DMSO-d$_6$) 1.54 (s, 9H), 2.21 (s, 3H), 2.39 (m, 4H), 2.43 (s, 3H), 3.70 (m, 4H), 6.95 (s, 1H), 7.18 (m, 2H), 7.56 (m, 2H), 7.91 (d, 2H), 8.06 (d, 2H), 8.66 (s, 1H), 9.89 (s, 1H); Mass Spectrum: M + H$^+$ 527. | |
| 8 | (structure: 3,5-dicyanopyridin-2-yl) | NMR Spectrum: (DMSO-d$_6$) 1.44 (s, 9H), 7.17 (m, 2H), 7.56 (t, 2H), 8.08 (d, 2H), 8.16 (d, 2H), 8.71 (br s, 1H), 9.12 (d, 1H), 9.40 (d, 1H), 9.98 (br s, 1H); | CAS No. 172208-08 National academy of science letters 1995, 18, 15 |

Method 8

T-butyl[2-({4-[3-cyano-5-(piperidin-1-ylmethyl)pyridin-2-yl]benzoyl}amino)phenyl]carbamate

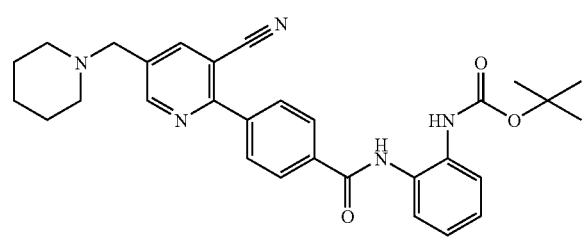

A solution of N-(2-t-butoxycarbonylaminophenyl)-4-(3-cyano-5-formylpyridin-2-yl)benzamide (400 mg, 0.905 mmol, prepared as described in Method 15) in dichloromethane (5 ml) was added over 20 min to a stirred mixture of piperidine (0.1 ml, 1.00 mmol) sodium triacetoxyborohydride (212 mg, 1.0 mmol), powdered 3A molecular sieve (500 mg) and dichloromethane (15 ml) at −20° C. under nitrogen. The reaction mixture was stirred for 16 hours at ambient temperature before being filtered and washed with saturated aqueous sodium hydrogen carbonate, dried over sodium sulfate and evaporated. The crude product was purified by chromatography on silica eluting with ethyl acetate to afford the title compound as a cream solid (252 mg, 55%); NMR Spectrum: (DMSO-d$_6$) 1.40 (m, 2H), 1.45 (s, 9H), 1.46 (m, 4H), 2.39 (m 4H), 3.58 (s, 2H), 7.17 (m, 2H), 7.56 (m, 2H), 8.01 (d, 2H), 8.12 (d, 2H), 8.31 (d, 1H), 8.69 (s, 1H), 8.87 (d, 1H), 9.94 (s, 1H); Mass Spectrum: M+H$^+$512.

Methods 9-14d

Using an analogous procedure to that described in Method 8 above, the appropriate amine starting material was reacted to give the compounds described in Table 14 below.

TABLE 14

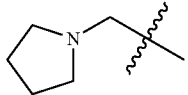

| Method | R[1b] | Analytical Data | SM |
|---|---|---|---|
| 9 | 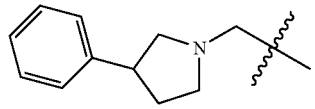 | NMR Spectrum: (DMSO-d$_6$) 1.45 (s, 9H), 1.72 (m, 4H), 2.50 (m, 4H), 3.73 (s, 2H), 7.18 (m, 2H), 7.56 (m 2H), 8.01 (d, 2H), 8.12 (d, 2H), 8.33 (d, 1H), 8.69 (s, 1H), 8.87 (d, 1H), 9.94 (s, 1H); Mass Spectrum: M + H$^+$ 498. | |
| 10 | 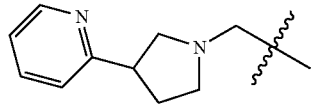 | NMR Spectrum: (DMSO-d$_6$) 1.45 (s, 9H), 1.81 (m, 1H), 2.27 (m, 1H), 2.51 (m, 1H), 2.75 (m, 2H), 2.99 (m, 1H), 3.34 (m, 1H), 3.80 (s, 2H), 7.18 (m, 3H), 7.29 (m, 4H), 7.56 (m, 2H), 8.02 (d, 2H), 8.13 (d, 2H), 8.38 (d, 1H), 8.68 (s, 1H), 8.93 (d, 1H), 9.95 (s, 1H); Mass Spectrum: M + H$^+$ 574. | |
| 11 | 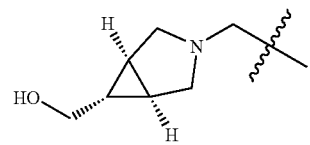 | NMR Spectrum: (DMSO-d$_6$) 1.45 (s, 9H), 2.05 (m, 1H), 2.24 (m, 1H), 2.67 (m, 2H), 2.84 (m, 1H), 3.04 (m, 1H), 3.52 (m, 1H), 3.81 (s, 2H), 7.18 (m, 3H), 7.33 (m, 1H), 7.55 (m, 2H), 7.69 (m, 1H), 8.02 (d, 2H), 8.12 (d, 2H), 8.37 (d, 1H), 8.48 (m, 1H), 8.69 (s, 1H), 8.91 (d, 1H), 9.94 (s, 1H); Mass Spectrum: M + H$^+$ 575. | |
| 12 | 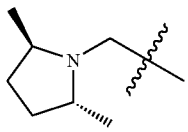 | NMR Spectrum: (DMSO-d$_6$) 1.27 (m, 2H), 1.34 (m, 1H), 1.45 (s, 9H), 2.39 (m, 2H), 2.91 (d, 2H), 3.24 (m, 2H), 3.71 (s, 2H), 4.37 (t, 1H), 7.18 (m, 2H), 7.57 (m, 2H), 8.01 (d, 2H), 8.12 (d, 2H), 8.27 (d, 1H), 8.69 (s, 1H), 8.84 (d, 1H), 9.94 (s, 1H); Mass Spectrum: M + H$^+$ 540. | CAS 185561-91-5 Brighty, Katherine E. et al; Syn Lett (1996), (11), 1097-1099. |
| 13 |  | NMR Spectrum: (DMSO-d$_6$) 0.97 (d, 6H), 1.35 (m, 2H), 1.54 (s, 9H) 1.99 (m, 2H), 3.00 (m, 2H), 3.80 (dd, 2H), 7.18 (m, 2H), 7.57 (m, 2H), 8.01 (d, 2H), 8.12 (d, 2H), 8.33 (d, 1H), 8.69 (s, 1H), 8.91 (d, 1H), 9.94 (s, 1H); Mass Spectrum: M + H$^+$ 526. | |

TABLE 14-continued

| Method | R¹ᵇ | Analytical Data | SM |
|---|---|---|---|
| 14 | (S)-1-methyl-3-(dimethylamino)pyrrolidinyl-methyl | NMR Spectrum: (DMSO-d₆) 1.45 (s, 9H), 1.63 (m, 1H), 1.87 (m, 1H), 2.08 (s, 6H), 2.13 (d, 1H), 2.33 (m, 1H), 2.61 (m, 1H), 2.73 (m, 2H), 3.70 (dd, 2H), 7.18 (m, 2H), 7.57 (m, 2H), 8.01 (d, 2H), 8.12 (d, 2H), 8.32 (d, 1H), 8.69 (s, 1H), 8.87 (d, 1H), 9.94 (s, 1H); Mass Spectrum: M + H⁺ 541. | |
| 14a | 3-(diethylamino)pyrrolidinyl-methyl | NMR Spectrum: (DMSO-d₆) 0.93 (t, 6H), 1.45 (s, 9H), 1.64 (m, 1H), 1.89 (m, 2H), 2.38 (m, 1H), 2.50 (m, 6H), 2.67 (m, 1H), 3.70 (dd, 2H), 7.19 (m, 2H), 7.55 (m, 2H), 8.01 (d, 2H), 8.12 (d, 2H), 8.32 (d, 1H), 8.71 (s, 1H), 8.88 (d, 1H), 9.96 (s, 1H); Mass Spectrum: M + H⁺ 569. | |
| 14b | N-butyl-N-methylaminomethyl | NMR Spectrum: (DMSO-d₆) 0.87 (t, 3H), 1.30 (m, 2H), 1.44 (m, 11H), 2.16 (s, 3H), 2.37 (t, 2H), 3.60 (s, 2H), 7.18 (m, 2H), 7.55 (m, 2H), 8.02 (d, 2H), 8.12 (d, 2H), 8.31 (d, 1H), 8.71 (s, 1H), 8.87 (d, 1H), 9.96 (s, 1H); Mass Spectrum: M + H⁺ 514. | |
| 14c | (1,3-dimethyl-1H-pyrazol-5-yl)methylaminomethyl-pyridinyl group | Mass Spectrum: M + H⁺ 552. | |
| 14d | 2-(3,5-dimethyl-1H-pyrazol-4-yl)ethylaminomethyl-pyridinyl group | Mass Spectrum: M + H⁺ 566. | |

Method 15

N-(2-t-butoxycarbonylaminophenyl)-4-(3-cyano-5-formylpyridin-2-yl)benzamide

N-(2-t-butoxycarbonylaminophenyl)-4-(4,4,5,5,tetramethyl-1,3,2,-dioxaborolan-2-yl)benzamide (1.2 g, 2.74 mmol; prepared as described in international patent publication number wo03/087057, method 13, page 60), 2-chloro-3-cyano-5-formylpyridine [prepared as described in de 4429465 a1 (1996)] (456 mg, 2.74 mmol), 1,1'-bis(diphenylphosphino)ferrocene-palladium(ii)dichloride dichloromethane complex 112 mg, 0.137 mmol), 1,2-dimethoxyethane (12 ml) and a saturated aqueous solution of sodium hydrogen carbonate (6 ml) were stirred at 60° c. under an atmosphere of nitrogen for 7.5 hours. the mixture was allowed to cool before being partitioned between dichloromethane and water. the organics were separated, dried over sodium sulfate, filtered and evaporated. the crude product was purified by chromatography on silica eluting with 30:70 to 40:60 ethyl acetate: isohexane to afford the title compound as a cream solid (615 mg, 51%); nmr spectrum: (dmso-d$_6$) 1.45 (s, 9h), 7.18 (m, 2h), 7.56 (m, 2h), 8.10 (d, 2h), 8.17 (d, 2h), 8.70 (s, 1h), 8.90 (d, 1h), 9.39 (d, 1h), 9.97 (s, 1h), 10.18 (s, 1h); mass spectrum: m+na$^+$ 465.

Methods 16-18

The starting materials for the above were synthesised from N-(2-t-butoxycarbonylaminophenyl)-4-(4,4,5,5,tetramethyl-1,3,2,-dioxaborolan-2-yl)benzamide (prepared as described in International Patent Publication Number WO03/G07057, Method 13, page 60) and the appropriate 2-chloro-pyridine using the procedure outlined in Method 15 above to give the compounds shown in Table 15 below.

Method 19 t-Butyl {2-[(4-{3-cyano-5-[(4-isopropylpiperazin-1-yl)methyl]pyridin-2-yl}benzoyl)amino]phenyl}carbamate

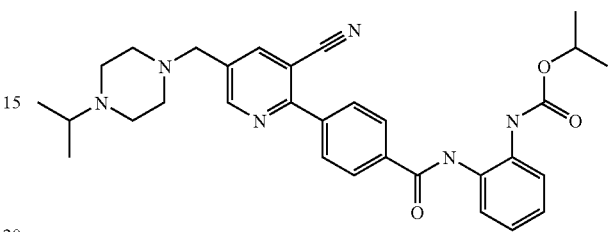

TABLE 15

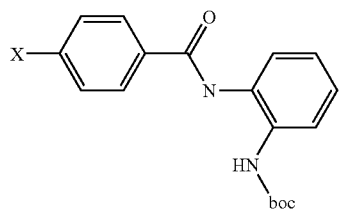

| Method | X | Analytical Data | SM |
|---|---|---|---|
| 16 | | Mass Spectrum: M − H$^-$ 458. | 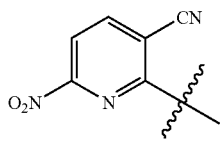 |
| 17 | | Mass Spectrum: M + H$^+$ 409. | 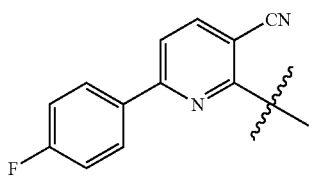 |
| 18 | | Mass Spectrum: M − H$^-$ 453. | 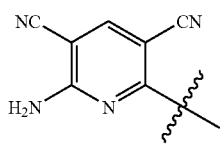 |

1,1'-Bis(diphenylphosphino)ferrocenedichloropalladium (II) chloride (58 mg, 0.072 mmol) was added to a mixture of N-(2-t-butoxycarbonylaminophenyl)-4-(4,4,5,5-tetramethyl-1,3,2-dioxaborolan-2-yl)benzamide (626 mg, 1.43 mmol prepared as described in International Patent Publication Number WO03/087057, Method 13, page 60), 2-chloro-5-[(4-isopropylpiperazin-1-yl)methyl]nicotinonitrile (398 mg, 1.43 mmol; see Method 20), saturated aqueous sodium hydrogen carbonate solution (5 ml) and 1,2-dimethoxyethane (10 ml). The mixture was heated at 80° C. for 1 hour then allowed to cool to room temperature and partitioned between dichloromethane (75 ml) and water (50 ml). The aqueous layer was extracted with further dichloromethane (2×75 ml). The combined organics were dried over magnesium sulfate, filtered and then evaporated to dryness. The residue was purified by flash chromatography on silica, eluting with methanol (5-10%) in dichloromethane to afford the title compound as a yellow gum which crystallised on trituration with diethyl ether, (652 mg, 82%).

NMR Spectrum: (DMSO-$d_6$ 373K) 0.97 (d, 6H), 1.46 (s, 9H), 2.45 (m, 8H), 2.62 (m, 1H), 3.62 (s, 2H), 7.17 (m, 1H), 7.22 (m, 1H), 7.57 (m, 2H), 8.02 (d, 2H), 8.13 (d, 2H), 8.33 (d, 1H), 8.71 (br s, 1H), 8.89 (d, 1H), 9.95 (br s, 1H); Mass Spectrum: M+H$^+$ 555.

Method 20

2-Chloro-5-[(4-isopropylpiperazin-1-yl)methyl]nicotinonitrile

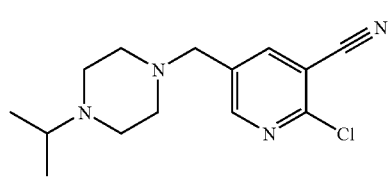

A 4.0 M solution of hydrogen chloride in dioxane (1.33 ml, 5.31 mmol) was added to a stirred suspension of sodium 3-cyano-5-[(4-isopropylpiperazin-1-yl)methyl]pyridin-2-olate (1.5 g, 5.31 mmol; see Method 21) in acetonitrile (15 ml). The mixture was heated to 40° C. and phosphorous oxychloride (2.48 ml, 26.6 mmol) added then the mixture was heated at 80° C. for 18 hours. After cooling to room temperature, isopropyl alcohol (8 ml) was added and the mixture stirred for 10 minutes. The mixture was diluted with water (50 ml) and basified with a solution of sodium hydroxide (1M) to pH 8. The product was extracted with dichloromethane (2×100 ml), the extracts dried over magnesium sulfate, filtered and concentrated to yield the title compound as a brown oil (1.2 g, 81%).

NMR Spectrum: (DMSO-$d_6$) 0.94 (d, 6H), 2.42 (m, 8H), 2.61 (m, 1H), 3.55 (s, 2H), 8.35 (s, 1H), 8.51 (s, 1H); Mass spectrum: M+H$^+$ 279.

Method 21

Sodium 3-cyano-5-[(4-isopropylpiperazin-1-yl)methyl]pyridin-2-olate

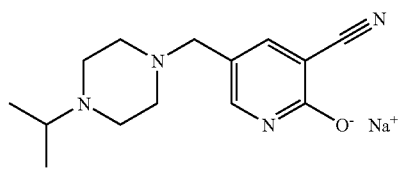

2-Cyanoacetamide (5.36 g, 63.7 mmol) was added to a solution of (2E)-3-(dimethylamino)-2-[(4-isopropylpiperazin-1-yl)methyl]acrylaldehyde (6.10 g, 25.5 mmol; see Method 22) in ethanol (150 ml), followed by drop wise addition of sodium ethoxide (21% solution in ethanol, 28.6 ml, 76.5 nmol) over 5 minutes. The solution was heated at reflux for 17 hours, then cooled to room temperature. The yellow solid was filtered and the filtrate concentrated in vacuo. The residue was triturated with diethyl ether and the solid obtained dried to yield the title compound (8.74 g, used without further purification).

NMR Spectrum: (DMSO-$d_6$) 0.93 (d, 6H), 2.26 (m, 4H), 2.37 (m, 4H), 2.55 (m, 1H), 3.09 (s, 2H), 7.24 (d, 1H), 7.74 (d, 1H); Mass spectrum: M+H$^+$ 261.

Method 22

(2E)-3-(Dimethylamino)-2-[(4-isopropylpiperazin-1-yl)methyl]acrylaldehyde

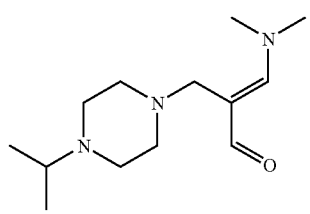

1-Isopropylpiperazine (4.4 ml, 30.6 mmol) was added to a solution of 3-(dimethylamino)acrolein (2.82 g, 25.5 mmol) in ethanol (100 ml), followed by formaldehyde (37% solution in water, 2.3 ml, 30.6 mmol) and acetic acid (100 μl). The mixture was stirred at 50° C. for 3.5 hours, then room temperature for 15 hours. The solution was concentrated in vacuo, re-dissolved in ethanol (25 ml) and then formaldehyde (2.3 ml) and acetic acid (100 μl) were added. The mixture was stirred at 60° C. for 4 hours then concentrated in vacuo to yield the title compound as a pale yellow oil (6.10 g, 90%).

NMR Spectrum: (CDCl$_3$) 1.02 (d, 6H), 2.51 (m, 8H), 2.67 (m, 1H), 3.19 (s, 2H), 3.24 (s, 6H), 6.61 (s, 1H), 8.92 (s, 1H); Mass spectrum: M+H$^+$ 240.

Method 23-25

Using an analogous procedure to that described in method 8, the appropriate amine starting material was reacted with n-(2-t-butoxycarbonylaminophenyl)-4-(3-cyano-5-formylpyridin-2-yl)benzamide to give the compounds shown in table 16 below.

TABLE 16

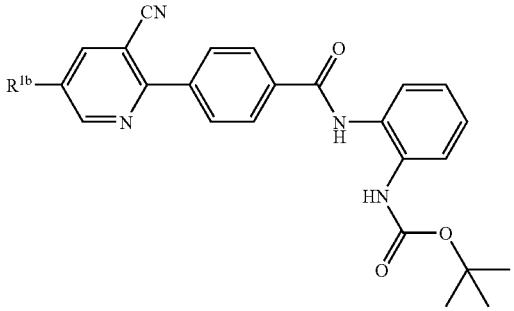

| Method | R^1b | Analytical Data | SM |
|---|---|---|---|
| 23 | 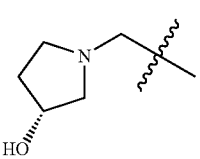 | NMR Spectrum: (DMSO-d$_6$) 1.45 (s, 9H), 1.58 (m, 1H), 2.02 (m, 1H), 2.38 (m, 1H), 2.45 (m, 1H), 2.66 (m, 1H), 2.73 (m, 1H), 3.72 (dd, 2H), 4.20 (m, 1H), 4.70 (d, 1H), 7.18 (m, 2H), 7.57 (m, 2H), 8.01 (d, 2H), 8.12 (d, 2H), 8.34 (d, 1H), 8.70 (s, 1H), 8.88 (d, 1H), 9.94 (s, 1H); Mass Spectrum: M + H$^+$ 514. | |
| 24 | | NMR Spectrum: (DMSO-d$_6$) 1.45 (s, 9H), 1.90 (m, 1H), 2.15 (m, 1H), 2.42 (m, 1H), 2.65 (m, 1H), 2.80 (m, 2H), 3.78 (s, 2H), 5.22 (m, 1H), 7.18 (m, 2H), 7.57 (m, 2H), 8.01 (d, 2H), 8.12 (d, 2H), 8.36 (d, 1H), 8.69 (s, 1H), 8.90 (d, 1H), 9.94 (s, 1H); Mass Spectrum: M + H$^+$ 516. | CAS136725-55-8 Giardina, G, et al; Synlett (1995), (1), 55-57. |
| 25 | 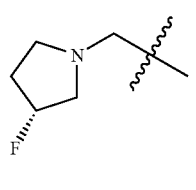 | NMR Spectrum: (DMSO-d$_6$) 1.38 (s, 9H), 1.45 (s, 9H), 1.71 (m, 1H), 2.00 (m, 2H), 2.38 (m, 1H), 2.57 (m, 2H), 2.72 (m, 1H), 2.76 (s, 3H), 3.71 (dd, 2H), 7.18 (m, 2H), 7.57 (m, 2H), 8.01 (d, 2H), 8.12 (d, 2H), 8.35 (d, 1H), 8.69 (s, 1H), 8.89 (d, 1H), 9.94 (s, 1H); Mass Spectrum: M + H$^+$ 627. | |

Method 26

Using an analogous procedure to that described in Method 15, N-(2-t-butoxycarbonylaminophenyl)-4-(4,4,5,5-tetramethyl-1,3,2-dioxaborolan-2-yl)benzamide (prepared as described in International Patent Publication Number WO03/087057, Method 13, page 60) was reacted with the appropriate 2-chloro-pyridine to give the compound shown in Table 17 below.

TABLE 17

| Method | X | Analytical Data | SM |
|---|---|---|---|
| 26 | H$_2$N—[pyridine with CN, methyl] | Mass Spectrum: M − H$^-$ 442. | CAS57183-29-6 Perez-Medina, LA et al; JACS (1947), 69, 2574-2579. |

Method 27

N-(2-t-Butoxycarbonylaminophenyl)-4-(3-cyano-5-(1-oxo-ethyl)-6-methylpyridin-2-yl)benzamide

1,1'-Bis(diphenylphosphino)ferrocenedichloropalladium (II) chloride (33 mg, 0.045 mmol) was added to a mixture of N-(2-t-butoxycarbonylaminophenyl)-4-(4,4,5,5,tetramethyl-1,3,2,-dioxaborolan-2-yl)benzamide (393 mg, 0.896 mmol prepared as described in International Patent Publication Number WO03/087057, Method 13, page 60), 5-acetyl-2-chloro-6-methylnicitinonitrile (174 mg, 0.896 mmol) and saturated aqueous sodium hydrogen carbonate solution (2 ml) in 1,2-dimethoxyethane (4 ml). The mixture was heated in a microwave at 80° C. for 1 hour. The mixture was allowed to cool, then partitioned between dichloromethane (30 ml) and water (20 ml). The aqueous layer was extracted with further dichloromethane (2×30 ml). The combined organics fractions were dried over magnesium sulfate, filtered then evaporated. The residue was purified by flash chromatography (eluting with 30:70→50:50 ethyl acetate:isohexane) to afford the title compound as a white solid (220 mg, 52%).

NMR Spectrum: (CDCl$_3$) 1.53 (s, 9H), 2.67 (s, 3H), 2.92 (s, 3H), 7.02 (s, 1H), 7.19 (m, 3H), 7.77 (m, 1H), 8.11 (m, 4H), 8.36 (s, 1H), 9.46 (br s, 1H); Mass spectrum: M+Na$^+$ 493.

Method 28 t-Butyl (2-{[4-(3-cyano-5-{[2-(ethylamino)ethoxy]methyl}pyridin-2-yl)benzoyl]amino}phenyl)carbamate

t-Butyl[2-({4-[3-cyano-5-(hydroxymethyl)pyridin-2-yl]benzoyl}amino)phenyl]carbamate (1.01 g, 2.27 mmol, prepared as described in Method 29) was dissolved with stirring in dichloromethane (50 ml). Methanesulfonyl chloride (0.44 ml, 5.69 mmol) was added followed by triethylamine (0.8 ml, 5.74 mmol) and the solution stirred for 3 hours at ambient temperature to form the mesylate.

Sodium hydride (300 mg of a 60% dispersion in mineral oil, 7.49 mmol) was added to a stirred solution of 2-(ethylamino)ethanol (0.66 ml, 6.81 mmol) in DMF (20 ml) and the solution stirred for 1 hour at ambient temperature. The solution of the mesylate in dichloromethane was then added and the resulting solution was stirred for 24 hours at ambient temperature. The solution was concentrated under reduced pressure and the residue treated with water. This was extracted with ethyl acetate, the combined organic extracts washed with brine then dried over magnesium sulphate and filtered. The resulting solution was concentrated under reduced pressure. The residue was purified by flash chromatography eluting with 2% methanol/dichloromethane to give t-butyl (2-{[4-(3-cyano-5-{[2-(ethylamino)ethoxy]methyl}pyridin-2-yl)benzoyl]amino}phenyl)carbamate (466 mg, 40%); NMR Spectrum: (DMSO-d$_6$) 1.02 (t, 3H), 1.47 (s, 9H), 2.56 (m, 4H), 3.51 (m, 2H), 3.76 (s, 2H), 4.44 (m, 1H), 7.21 (m, 2H), 7.59 (m, 2H), 8.03 (d, 2H), 8.14 (d, 2H), 8.40 (s, 1H), 8.71 (br s, 1H), 8.93 (s, 1H), 9.96 (s, 1H); Mass Spectrum: M+H$^+$ 516.

Method 29

T-butyl[2-({4-[3-cyano-5-(hydroxymethyl)pyridin-2-yl]benzoyl}amino)phenyl]carbamate

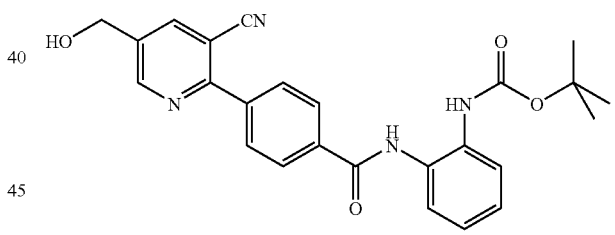

N-(2-t-Butoxycarbonylaminophenyl)-4-(3-cyano-5-formylpyridin-2-yl)benzamide (1.14 g, 2.57 mmol, prepared as described in Method 15) was dissolved in methanol (50 ml). Sodium borohydride (194 mg, 5.14 mmol) was added and the solution stirred for 1 hour at ambient temperature. The solution was concentrated under reduced pressure and the residue partitioned between saturated sodium bicarbonate solution and dichloromethane.

The aqueous layer was further extracted with dichloromethane and the combined organic extracts washed with brine then dried over magnesium sulphate and filtered. The solution was concentrated under reduced pressure to give t-butyl[2-({4-[3-cyano-5-(hydroxymethyl)pyridin-2-yl]benzoyl}amino)phenyl]carbamate (1.11 g, 97%); NMR Spectrum: (DMSO-d$_6$) 1.46 (s, 9H), 4.67 (d, 2H), 5.58 (t, 1H), 7.20 (m, 2H), 7.59 (m, 2H), 8.05 (d, 2H), 8.13 (d, 2H), 8.35 (s, 1H), 8.70 (br s, 1H), 8.93 (s, 1H), 9.96 (br s, 1H); Mass Spectrum: M+H$^+$ 445.

Method 30 t-Butyl (2-{[4-(3-cyano-5-{[2-(methylamino)ethoxy]methyl}pyridin-2-yl)benzoyl]amino}phenyl)carbamate

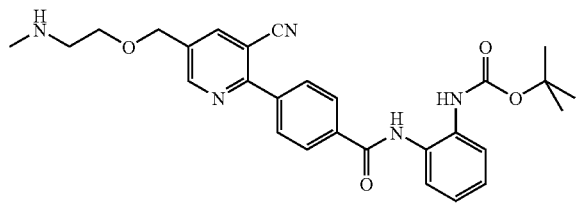

t-Butyl[2-({4-[3-cyano-5-(hydroxymethyl)pyridin-2-yl]benzoyl}amino)phenyl]carbamate (1.01 g, 2.27 mmol, prepared a described in Method 29) was dissolved with stirring in dichloromethane (50 ml). Methanesulfonyl chloride (0.44 ml, 5.69 mmol) was added followed by triethylamine (0.8 ml, 5.74 mmol) and the solution stirred for 3 hours at ambient temperature to form the mesylate.

Sodium hydride (545 mg of a 60% dispersion in mineral oil, 13.62 mmol) was added to a stirred solution of 2-(methylamino)ethanol (1.10 ml, 13.62 mmol) in DMF (20 ml) and the solution stirred for 1 hour at ambient temperature. The solution of the 'mesylate' in dichloromethane was added and the resulting solution was stirred for 24 hours at ambient temperature. The solution was concentrated under reduced pressure and the residue treated with water. This was extracted with ethyl acetate, the combined extracts washed with brine, dried over magnesium sulphate and filtered. The solution was concentrated under reduced pressure. The residue was purified by flash chromatography eluting with 2% methanol/dichloromethane to give t-butyl (2-{[4-(3-cyano-5-{[2-(methylamino)ethoxy]methyl}pyridin-2-yl)benzoyl]amino}phenyl)carbamate (465 mg, 41%); NMR Spectrum: (DMSO-$d_6$) 1.46 (s, 9H), 2.24 (s, 3H), 2.51 (m, 2H), 3.56 (m, 2H), 3.69 (s, 2H), 4.46 (m, 1H), 7.19 (m, 2H), 7.58 (m, 2H), 8.04 (d, 2H), 8.14 (d, 2H), 8.40 (s, 1H), 8.71 (br s, 1H), 8.92 (s, 1H), 9.96 (s, 1H); Mass Spectrum: M+H$^+$ 502.

Method 31 t-Butyl (2-{[4-(3-cyano-5-{[2-(isopropylamino)ethoxy]methyl}pyridin-2-yl)benzoyl]amino}phenyl)carbamate

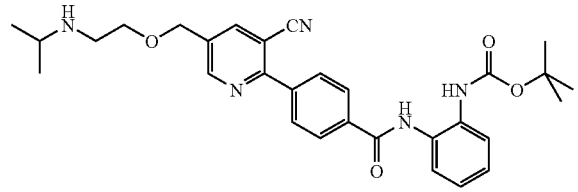

t-Butyl[2-({4-[3-cyano-5-(hydroxymethyl)pyridin-2-yl]benzoyl}amino)phenyl]carbamate (555 mg, 1.25 mmol) was stirred and dissolved in DMF (20 ml). Methanesulfonyl chloride (0.19 ml, 2.46 mmol) was added followed by triethylamine (0.38 ml, 2.73 mmol) and the solution stirred for 2 hours at ambient temperature.

Sodium hydride (166 mg of a 60% dispersion in mineral oil, 4.15 mmol) was added to a stirred solution of iso-propylaminoethanol (0.43 ml, 3.74 mmol) in DMF (10 ml) and the solution stirred for 1 hour at ambient temperature. The solution of the 'mesylate' in DMF was added and the resulting solution was stirred for 24 hours at ambient temperature. The reaction was poured into water (300 ml) and the resulting precipitate filtered then washed with water (X 3). The resulting solution was absorbed onto an SCX-2 column, which was washed with methanol (3 column volumes) and the product eluted with a 2M solution of ammonia in methanol (3 column volumes) then concentrated to give the product, t-butyl (2-{[4-(3-cyano-5-{[2-(isopropylamino)ethoxy]methyl}pyridin-2-yl)benzoyl]amino}phenyl)carbamate as a foam (170 mg, 26%); NMR Spectrum: (DMSO-$d_6$) 1.03 (d, 6H), 1.45 (s, 9H), 2.54 (m, 2H), 2.91 (m, 1H), 3.41 (m, 2H), 3.75 (s, 2H), 4.37 (m, 1H), 7.20 (m, 2H), 7.58 (m, 2H), 8.04 (d, 2H), 8.13 (d, 2H), 8.41 (s, 1H), 8.71 (br s, 1H), 8.94 (s, 1H), 9.96 (s, 1H); Mass Spectrum: M+H$^+$ 530.

The invention claimed is:
1. A compound of formula (I):

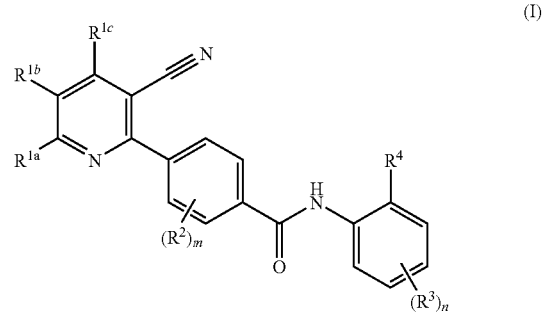

wherein:
R$^{1a}$ is selected from hydrogen, amino, nitro, (1-3C)alkyl, N-(1-3C)alkylamino, N,N-di-(1-3C)alkylamino, phenyl, or piperazinyl;
and wherein:
(i) if R$^{1a}$ is N-(1-3C)alkylamino or N,N-di-(1-3C)alkylamino group, the (1-3C)alkyl moiety is optionally substituted by hydroxy or (1-3C)alkoxy;
(ii) if R$^{1a}$ is phenyl, it is optionally substituted by halo, amino, N-(1-3)alkylamino, or N,N-di-(1-3C)alkylamino; and
(iii) if R$^{1a}$ is piperazinyl, it is optionally substituted by halo, amino, (1-3C)alkyl, N-(1-3)alkylamino, or N,N-di-(1-3C)alkylamino;
R$^{1b}$ is selected from:
(i) hydrogen, halo, nitro, cyano, hydroxy, trifluoromethyl, trifluoromethoxy, amino, carboxy, carbamoyl, mercapto, sulphamoyl, (1-6C)alkyl, hydroxy(1-6C)alkyl, (2-6C)alkenyl, (2-6C)alkynyl, (3-6C)cycloalkyl, (3-6C)cycloalkyl(1-6C)alkyl, (3-6C)cycloalkenyl, (3-6C)cycloalkenyl(1-6C)alkyl, (1-6C)alkoxy, (1-6C)alkanoyloxy, N-(1-6C)alkylamino, N,N-di-[(1-6C)alkyl]amino, N-[(3-6C)cycloalkyl]amino, N,N-di-[(3-6C)cycloalkyl]amino, N-[(3-6C)cycloalkyl(1-6C)alkyl]amino, N,N-di-[(3-6C)cycloalkyl(1-6C)alkyl]amino, N-[(3-6C)cycloalkyl]-N-[(1-6C)alkyl]amino, N-[(3-6C)cycloalkyl(1-6C)alkyl]-N-[(1-6C)alkyl]amino, N-(1-6C)alkanoylamino, N,N-di-[(1-6C)alkanoyl]amino, N-[(1-6C)alkoxy(1-6C)alkyl]amino, N,N-di-[(1-6C)

alkoxy(1-6C)alkyl]amino, N-[(1-6C)alkoxy(1-6C)alkyl]-N-[(1-6C)alkyl]amino, N-(1-6C)alkylcarbamoyl, N,N-di-[(1-6C)alkyl]carbamoyl, (1-6C)alkylthio, (1-6)alkylsulphinyl, (1-6C)alkylsulphonyl, (1-6C)alkoxycarbonyl, N-(1-6C)alkylsulphamoyl, N,N-di-[(1-6C)alkyl]sulphamoyl, aryl, aryl-(1-6C)alkyl, a carbon linked heterocyclyl group, or a heterocyclyl-(1-6C)alkyl group wherein the heterocyclyl moiety is carbon-linked to the alkyl group; or (ii) a group of sub-formula II:

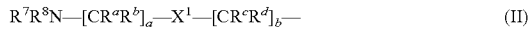   (II)

wherein:

X$^1$ is selected from a direct bond, —O— or —C(O)—;

integer a is 0, 1, 2, 3 or 4, with the proviso that if X$^1$ is —O—, integer a is at least 1;

integer b is 0, 1, 2, 3 or 4;

each R$^a$, R$^b$, R$^c$ and R$^d$ group present is independently selected from hydrogen, halo, hydroxy or (1-4C)alkyl;

R$^7$ and R$^8$ are independently selected from hydrogen, (1-6C)alkyl, hydroxy(1-6C)alkyl, halo(1-6C)alkyl, (2-6C)alkenyl, (3-6C)cycloalkyl, (3-6C)cycloalkyl(1-6C)alkyl, (1-6C)alkoxy(1-6C)alkyl, (1-6C)alkanoyl, (3-6C)cycloalkenyl, (3-6C)cycloalkenyl(1-6C)alkyl, aryl, aryl(1-6C)alkyl, heterocyclyl;

a heterocyclyl-(1-6C)alkyl group wherein the heterocyclyl moiety is carbon-linked to the alkyl group and is either selected from a substituted or unsubstituted thienyl, pyrimidinyl, pyridazinyl, furanyl, tetrahydrofuranyl, pyranyl, tetrahydropyranyl, pyridinyl, pyrazinyl, thiazolyl, or indolyl group, or from one the following particular substituent groups: 1,3-dimethyl-1H-pyrazol-5-yl, 3,5-dimethyl-1H-pyrazol-4-yl, and 1-methyl-1H-imidazol-4-yl;

a group of sub-formula III:

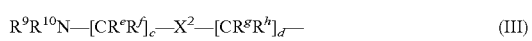   (III)

wherein:

X$^2$ is selected from a direct bond, —O— or —C(O)—;

integer c is 1, 2 or 3;

integer d is 0, 1, 2 or 3;

each R$^e$, R$^f$, R$^g$ and R$^h$ group present is independently selected from hydrogen, halo, hydroxy or (1-4C)alkyl;

R$^9$ and R$^{10}$ are independently selected from hydrogen, (1-6C)alkyl, hydroxy(1-6C)alkyl, halo(1-6C)alkyl, (3-6C)cycloalkyl, (3-6C)cycloalkyl(1-6C)alkyl, (1-6C)alkoxy(1-6C)alkyl, or R$^9$ and R$^{10}$ are linked so that, together with the nitrogen atom to which they are attached, they form a 4-, 5-, 6- or 7-membered non-aromatic heterocyclic ring, said heterocyclic ring optionally comprising, in addition to the nitrogen atom to which R$^9$ and R$^{10}$ are attached, one or two further heteroatoms selected from N, O or S, and wherein said heterocyclic ring is optionally substituted by hydroxy, halo, (1-4C)alkyl, carbamoyl, or —[CH$_2$]$_e$—NR$^{11}$R$^{12}$ (wherein integer e is 0, 1 or 2, and R$^{11}$ and R$^{12}$ are independently selected from hydrogen, (1-6C)alkyl, (3-6C)cycloalkyl or (3-6C)cycloalkyl(1-6C)alkyl);

or R$^7$ and R$^8$ are linked so that, together with the nitrogen atom to which they are attached, they form a 4 to 10-membered heterocyclic ring, said heterocyclic ring optionally comprising, in addition to the nitrogen atom to which R$^7$ and R$^8$ are attached, one or two further nitrogen atoms; or (iii) a group of the sub-formula IV:

   (IV)

wherein:

Y$^1$ is a direct bond or —[CR$^{13}$R$^{14}$]$_x$— where integer x is 1 to 4 and R$^{13}$ and R$^{14}$ are independently selected from hydrogen, halo and (1-4C)alkyl;

X$^3$ is selected from —O—, —S—, —SO—, —SO$_2$—, —C(O)—, —OC(O)— and —C(O)O—, with the proviso that Y$^1$ is not a direct bond if X$^3$ is —C(O)— and Q$^1$ is selected from (1-6C)alkyl, (3-6C)cycloalkyl, (3-6C)cycloalkyl(1-6C)alkyl, (3-6C)cycloalkenyl, (3-6C)cycloalkenyl(1-6C)alkyl, aryl, aryl-(1-6C)alkyl, heterocyclyl, heterocyclyl-(1-6C)alkyl, or R$^{15}$R$^{16}$N-(1-6C)alkyl (wherein R$^{15}$ and R$^{16}$ are each independently selected from hydrogen, (1-6C)alkyl, (1-6C)alkoxy, (1-6C)alkoxy(1-6C)alkyl, (1-6C)alkanoyl, (3-6C) cycloalkyl, (3-6C)cycloalkyl(1-6C)alkyl, (3-6C)cycloalkenyl, or (3-6C)cycloalkenyl(1-6C)alkyl);

and wherein any heterocyclyl ring within a R$^{1b}$ substituent group apart from those for which particular substituents are expressly stated above) is optionally substituted on carbon by one or more Z$^1$ substituent groups which may be the same or different, selected from:

(a) halo, nitro, cyano, hydroxy, trifluoromethyl, trifluoromethoxy, amino, carboxy, carbamoyl, mercapto, sulphamoyl, (1-6C)alkyl, hydroxy(1-6C)alkyl, (2-6C)alkenyl, (2-6C)alkynyl, (1-6C)alkoxy, (1-6C)alkanoyl, (1-6C)alkanoyloxy, (1-6C)alkoxy-(1-6C)alkyl, (1-6C)alkoxycarbonyl, halo(1-6C)alkyl, N-[(1-6C)alkyl]amino, N,N-di-[(1-6C)alkyl]amino, N-(1-6C)alkylcarbamoyl, N,N-di-[(1-6C)alkyl]carbamoyl, (1-6C)alkylthio, (1-6C)alkylsulphinyl, (1-6C)alkylsulphonyl, N-(1-6C)alkylsulphamoyl, N,N-di-[(1-6C)alkyl]sulphamoyl, aryl, aryl-(1-6C)alkyl, heterocyclyl, heterocyclyl-(1-6C)alkyl, (a) a group of the sub-formula V:

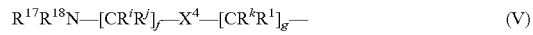   (V)

wherein

X$^4$ is selected from a direct bond, —O— or —C(O)—;

integer f is 0, 1, 2 or 3, with the proviso that integer f is at least 1 if X$^4$ is —O—;

integer g is 0, 1 or 2;

each R$^i$, R$^j$, R$^k$ and R$^l$ group present is independently selected from hydrogen, halo, hydroxy or (1-4C)alkyl;

R$^{17}$ and R$^{18}$ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl; or (c) a group of the sub-formula VI:

   (VI)

wherein:
Y² is a direct bond or —[CR¹⁹R²⁰]$_y$— wherein integer y is 1 to 4 and R¹⁹ and R²⁰ are independently selected from hydrogen, halo and (1-4C)alkyl;
X⁵ is selected from —O—, —S—, —SO—, —SO₂—, —C(O)—, —OC(O)— or —C(O)O—; and
Q² is selected from (1-6C)alkyl, (3-6C)cycloalkyl, (3-6C)cycloalkyl(1-6C)alkyl, (3-6C)cycloalkenyl, (3-6C)cycloalkenyl(1-6C)alkyl, aryl, aryl-(1-6C)alkyl, heterocyclyl, heterocyclyl-(1-6C)alkyl, R²¹R²²N-(1-6C)alkyl (wherein R²¹ and R²² are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl);

and wherein if any heterocyclyl group within a R¹ᵇ substituent group contains an unsubstituted nitrogen atom, then, unless any particular substituents are expressly stated in the definition above, the nitrogen atom may be optionally substituted by one or more Z² substituent groups, which may be the same or different, selected from:

(a) trifluoromethyl, carboxy, carbamoyl, (1-6C)alkyl, hydroxy(1-6C)alkyl, (2-6C)alkenyl, (1-6C)alkanoyl, (1-6C)alkoxy-(1-6C)alkyl, (1-6C)alkoxycarbonyl, halo(1-6C)alkyl, N-(1-6C)alkylamino-(1-6C)alkyl, N,N-di-[(1-6C)alkyl]amino-(1-6C)alkyl, (1-6C)alkylsulphonyl, aryl, aryl-(1-6C)alkyl, heterocyclyl, heterocyclyl-(1-6C)alkyl; or (b) a group of the formula VII:

R²³R²⁴N—[CR^m R^n]$_h$—     (VII)

wherein
integer h is 0, 1, 2, or 3;
each R^m and R^n group present is independently selected from hydrogen, halo, hydroxy or (1-4C)alkyl;
R²³ and R²⁴ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl; or (c) a group of the formula VIII:

Q³-X⁶—Y³—     (VIII)

wherein Y³ is a direct bond or —[CR²⁵R²⁶]$_z$— wherein z is 1 to 4 and R²⁵ and R²⁶ are independently selected from hydrogen, halo and (1-4C)alkyl;
X⁶ is selected from —O—, —S—, —SO—, —SO₂—, —C(O)—, —OC(O)— or —C(O)O— if Y³ is —[CR²³R²⁴]$_z$—, and if Y³ is a direct bond, X⁶ is selected from —S—, —SO—, —SO₂—, —C(O)—, and —OC(O)—; and
Q³ is selected from (1-6C)alkyl, (3-6C)cycloalkyl, (3-6C)cycloalkyl(1-6C)alkyl, aryl, aryl-(1-6C)alkyl, heterocyclyl, heterocyclyl-(1-6C)alkyl or R²⁷R²⁸N-(1-6C)alkyl (wherein R²⁷ and R²⁸ are each independently selected from hydrogen, (1-6C)alkyl, (1-6C)alkoxy, (1-6C)alkoxy(1-6C)alkyl, (1-6C)alkanoyl, (3-6C)cycloalkyl, (3-6C)cycloalkyl(1-6C)alkyl, (3-6C)cycloalkenyl, or (3-6C)cycloalkenyl(1-6C)alkyl);

and wherein any heterocyclyl group within a Z¹ or Z² substituent group optionally bears one or more substituent groups, which may be the same or different, selected from halo, cyano, trifluoromethyl, amino, carboxy, carbamoyl, mercapto, sulphamoyl, (1-6C)alkyl, hydroxy(1-6C)alkyl, halo(1-6C)alkyl, (2-6C)alkenyl, (2-6C)alkynyl, (1-6C)alkoxy, (1-6C)alkanoyl, (1-6C)alkanoyloxy, N-[(1-6C)alkyl]amino, and N,N-di-[(1-6C)alkyl]amino;

and wherein any non-aromatic heterocyclyl group within a R¹ᵇ substituent (including optional substituent groups Z¹ and Z²) optionally bears 1 or 2 oxo substituents;

and wherein any alkyl, alkenyl, alkynyl, alkoxy, alkanoyl, alkanoyloxy, cycloalkyl, or cycloalkenyl group within a R¹ᵇ substituent group (including optional substituent groups Z¹ and Z²) is, unless particular substituents are expressly stated above, optionally substituted by one or more Z³ substituent groups, which may be the same or different, selected from halo, cyano, mercapto, (1-6C)alkoxy, trifluoromethyl, or —NR²⁹R³⁰ wherein each of R²⁹ and R³⁰ is independently selected from hydrogen, (1-6C)alkyl, (1-6C)alkoxy, (3-6C)cycloalkyl, (3-6C)cycloalkyl(1-6C)alkyl;

and wherein any aryl group within a R¹ᵇ substituent group (including optional substituent groups Z¹ and Z²) is optionally substituted by one or more Z⁴ substituent groups, which may be the same or different, selected from halo, nitro, cyano, hydroxy, amino, (1-6C)alkyl, hydroxy(1-6C)alkyl, halo(1-6C)alkyl, (1-6C)alkoxy, (1-6C)alkanoyl, N-[(1-6C)alkyl]amino, N,N-di-[(1-6C)alkyl]amino, carbamoyl, N-(1-6C)alkylcarbamoyl, N,N-di-[(1-6C)alkyl]carbamoyl;

R¹ᶜ is selected from hydrogen, halo, nitro, cyano, hydroxy, trifluoromethyl, trifluoromethoxy, amino, carboxy, carbamoyl, mercapto, sulphamoyl, (1-3C)alkyl, (2-3C)alkenyl, (2-3C)alkynyl, (1-3C)alkoxy, (1-3C)alkanoyl, (1-3C)alkanoyloxy, N-(1-3C)alkylamino, N,N-di-[(1-3C)alkyl]amino, (1-3C)alkanoylamino, N-(1-3C)alkylcarbamoyl, N,N-di-(1-3C)alkylcarbamoyl, (1-3C)alkylthio, (1-3C)alkylsulphinyl, (1-3)alkylsulphonyl, (1-3C)alkoxycarbonyl, N-(1-3C)alkylsulphamoyl, and N,N-di-(1-3C)alkylsulphamoyl;

with the proviso that at least one of R¹ᵃ, R¹ᵇ and R¹ᶜ is hydrogen;

m is 0, 1, 2, 3 or 4;

R² is halo;

n is 0, 1, 2, 3 or 4;

R³ is selected from halo, nitro, cyano, hydroxy, trifluoromethyl, trifluoromethoxy, amino, carboxy, carbamoyl, mercapto, sulphamoyl, (1-3C)alkyl, (2-3C)alkenyl, (2-3C)alkynyl, (1-3C)alkoxy, (1-3C)alkanoyl, (1-3C)alkanoyloxy, N-(1-3C)alkylamino, N,N-di-[(1-3C)alkyl]amino, (1-3C)alkanoylamino, N-(1-3C)alkylcarbamoyl, N,N-Di(1-3C)alkylcarbamoyl, (1-3C)alkylthio, (1-3C)alkylsulphinyl, (1-3C)alkylsulphonyl, (1-3C)alkoxycarbonyl, N-(1-3C)alkylsulphamoyl, and N,N-di-(1-3C)alkylsulphamoyl; and R⁴ is amino or hydroxy;

or a pharmaceutically acceptable salt thereof.

2. The compound according to claim 1 or a pharmaceutically acceptable salt thereof, wherein said compound has the general structural formula VIII:

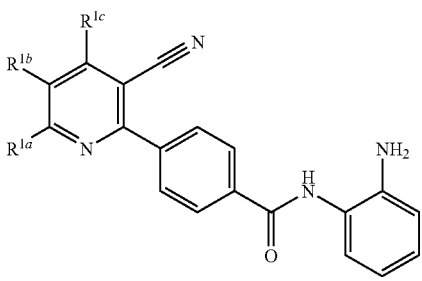

(VIII)

wherein $R^{1a}$, $R^{1b}$ and $R^{1c}$ are as defined in claim 1.

3. The compound according to claim 1 or a pharmaceutically acceptable salt thereof, wherein $R^{1a}$ is selected from hydrogen, amino, nitro, (1-3C)alkyl, N-(1-3C)alkylamino, phenyl, or piperazinyl, and wherein:
(i) if $R^{1a}$ is N-(1-3C)alkylamino, the (1-3C)alkyl moiety is optionally substituted by hydroxy;
(ii) if $R^{1a}$ is phenyl it is optionally substituted by halo; and
(iii) if $R^{1a}$ is piperazinyl it is optionally substituted by (1-3C)alkyl.

4. The compound according to claim 1 or a pharmaceutically acceptable salt thereof, wherein $R^{1b}$ is selected from:
(i) hydrogen, cyano, amino, (1-4C)alkyl, hydroxy(1-4C)alkyl; or
(ii) a group of sub-formula II:

$$R^7R^8N\text{—}[CR^aR^b]_a\text{—}X^1\text{—}[CR^cR^d]_b\text{—} \quad (II)$$

wherein:
$X^1$ is selected from a direct bond, or —O—;
integer a is 1, 2, or 3;
integer b is 0, 1, or 2;
each $R^a$, $R^b$, $R^c$ and $R^d$ group present is independently selected from hydrogen or (1-2C)alkyl;
$R^7$ and $R^8$ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;
an aryl group which is unsubstituted or substituted with one to three substituents selected from the group consisting of halo, cyano, hydroxy, amino, (1-4C)alkyl, or (1-4C)alkoxy;
an aryl(1-2C)alkyl group the aryl moiety of which is unsubstituted or substituted with one to three substituents selected from the group consisting of halo, cyano, hydroxy, amino, (1-4C)alkyl, or (1-4C)alkoxy;
a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C)alkoxy;
a heterocyclyl-(1-2C)alkyl group wherein the heterocyclyl moiety is carbon-linked to the alkyl group and is either selected from the group consisting of a furanyl, tetrahydrofuranyl, pyranyl, tetrahydropyranyl, pyridinyl, pyrazinyl, thiazolyl, indolyl group, each of which is unsubstituted or substituted with one to three substituents selected from the group consisting of halo, cyano, hydroxy, amino, (1-4C)alkyl, halo(1-4C)alkyl or (1-4C)alkoxy, or the heterocyclyl moiety is selected from 1,3-dimethyl-1H-pyrazol-5-yl, 3,5-dimethyl-1H-pyrazol-4-yl, and 1-methyl-1H-imidazol-4-yl;
a group of sub-formula III:

$$R^9R^{10}N\text{—}[CR^eR^f]_c\text{—}X^2\text{—}[CR^gR^h]_d\text{—} \quad (III)$$

wherein:
$X^2$ is selected from a direct bond, or —O—;
integer c is 1, 2 or 3;
integer d is 0, 1, or 2;
each $R^e$, $R^f$, $R^g$ and $R^h$ group present is independently selected from hydrogen or (1-2C)alkyl;
$R^9$ and $R^{10}$ are independently selected from hydrogen, (1-4C)alkyl, (3-6C)cycloalkyl, (3-6C)cycloalkyl(1-2C)alkyl, or $R^9$ and $R^{10}$ are linked so that, together with the nitrogen atom to which they are attached, they form a 4, 5-, or 6-membered non-aromatic heterocyclic ring, said heterocyclic ring optionally comprising, in addition to the nitrogen atom to which $R^9$ and $R^{10}$ are attached, one or two further heteroatoms selected from N, O or S, and wherein said heterocyclic ring is optionally substituted by hydroxy, halo, or (1-4C)alkyl;
or $R^7$ and $R^8$ are linked so that, together with the nitrogen atom to which they are attached, they form a 4 to 8-membered heterocyclic ring, said heterocyclic ring optionally comprising, in addition to the nitrogen atom to which $R^7$ and $R^8$ are attached, one or two further nitrogen atoms, and wherein said heterocyclic ring is optionally substituted on carbon by one to three substituents selected from:
(a) halo, cyano, hydroxy, trifluoromethyl, amino, (1-4C)alkyl, hydroxy(1-4C)alkyl, halo(1-4C)alkyl, N-[(1-4C)alkyl]amino, N,N-di-[(1-4C)alkyl]amino,
an aryl group which is optionally substituted with halo, cyano, hydroxy, amino, (1-4C)alkyl, or (1-4C)alkoxy;
an aryl-(1-2C)alkyl wherein the aryl moiety is optionally substituted with halo, cyano, hydroxy, amino, (1-4C)alkyl, or (1-4C)alkoxy;
a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C)alkoxy;
a heterocyclyl-(1-2C)alkyl group wherein the heterocyclyl moiety is a 4, 5, or 6-membered heterocyclyl group comprising up to three heteroatoms selected from N, O or S and is optionally substituted with halo, cyano, hydroxy, amino, (1-4C)alkyl, or (1-4C)alkoxy;
(b) a group of the sub-formula VI:

$$Q^2\text{-}X^5\text{—}Y^2\text{—} \quad (VI)$$

wherein:
$Y^2$ is a direct bond or —$[CR^{19}R^{20}]_y$— wherein integer y is 1 or 2 and $R^{19}$ and
$R^{20}$ are both hydrogen or (1-2C)alkyl;
$X^5$ is selected from —O— or —C(O)—; and
$Q^2$ is selected from
a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C)alkoxy;

a heterocyclyl-(1-2C)alkyl group wherein the heterocyclyl moiety is a 4, 5, or 6-membered heterocyclyl group comprising up to three heteroatoms selected from N, O or S, and is optionally substituted with one to three substituents selected from the group consisting of halo, cyano, hydroxy, amino, (1-4C)alkyl, or (1-4C)alkoxy;

and, if said heterocyclic ring comprises a nitrogen atom then said nitrogen is optionally substituted by one or more substituent groups, which may be the same or different, selected from:

(a) (1-4C)alkyl, hydroxy(1-4C)alkyl, (2-4C)alkenyl, (1-4C)alkanoyl, (1-4C)alkoxy-(1-4C)alkyl;
  an aryl group which is optionally substituted with halo, cyano, hydroxy, amino, (1-4C)alkyl, or (1-4C)alkoxy;
  an aryl-(1-2C)alkyl wherein the aryl moiety is optionally substituted with halo, cyano, hydroxy, amino, (1-4C)alkyl, or 1-4C)alkoxy;
  a 4, 5, or 6-membered heterocyclyl group comprising up to three heteroatoms selected from N, O or S, and which is unsubstituted or substituted with one to three substituents selected from the group consisting of halo, cyano, hydroxy, amino, (1-4C)alkyl, or (1-4C)alkoxy;
  a heterocyclyl-(1-2C)alkyl group wherein the heterocyclyl moiety is a 4, 5, or 6-membered heterocyclyl group comprising up to three heteroatoms selected from N, O or S, and is optionally substituted with halo, cyano, hydroxy, amino, (1-4C)alkyl, or (1-4C)alkoxy;

(b) a group of the formula VII:

$$R^{23}R^{24}N-[CR^mR^n]_h- \quad (VII)$$

wherein
  integer h is 0, 1, or 2;
  each $R^m$ and $R^n$ group present is hydrogen;
  $R^{23}$ and $R^{24}$ are each independently selected from hydrogen or (1-4C)alkyl; or (c) a group of the formula VIII:

$$Q^3-X^6-Y^3- \quad (VIII)$$

wherein $Y^3$ is a direct bond or $-[CR^{25}R^{26}]_z-$ wherein z is 1 to 2 and $R^{25}$ and $R^{26}$ are independently selected from hydrogen or (1-2C)alkyl;
  $X^6$ is selected from —O— or —C(O)—, if $Y^3$ is $-[CR^{23}R^{24}]_z-$, and if $Y^3$ is a direct bond, $X^6$ is selected from —S—, —SO—, —SO$_2$— or —C(O)—; and
  $Q^3$ is selected from (1-4C)alkyl, (3-6C)cycloalkyl, (3-6C)cycloalkyl(1-2C)alkyl,
    a 4, 5, or 6-membered heterocyclyl group comprising up to three heteroatoms selected from N, O or S, and which is unsubstituted or substituted with one to three substituents selected from the group consisting of halo, nitro, cyano, hydroxy, amino, (1-4C)alkyl, hydroxy(1-4C)alkyl, halo(1-4C)alkyl, (1-4C)alkoxy;
    a heterocyclyl-(1-2C)alkyl group wherein the heterocyclyl moiety is a 4, 5, or 6-membered heterocyclyl group comprising up to three heteroatoms selected from N, O or S, and is optionally substituted with halo, nitro, cyano, hydroxy, amino, (1-4C)alkyl, hydroxy(1-4C)alkyl, halo (1-4C)alkyl, (1-4C)alkoxy;

and wherein any non-aromatic heterocyclyl group within a $R^{1b}$ substituent group optionally bears 1 or 2 oxo substituents.

5. The compound according to claim 1 or a pharmaceutically acceptable salt thereof, wherein $R^{1b}$ is selected from:
(i) hydrogen, amino, (1-4C)alkyl; or
(ii) a group of sub-formula II:

$$R^7R^8N-[CR^aR^b]_a-X^1-[CR^cR^d]_b- \quad (II)$$

wherein:
$X^1$ is selected from a direct bond or —O—;
integer a is 1, or 2;
integer b is 0, 1, or 2;
each $R^a$, $R^b$, $R^c$ and $R^d$ group present is independently selected from hydrogen or (1-2C)alkyl;
$R^7$ and $R^8$ are independently selected from hydrogen; (1-6C)alkyl; hydroxy(1-4C)alkyl; (2-4C)alkenyl; (3-6C)cycloalkyl; (3-6C)cycloalkyl(1-2C)alkyl; (1-4C)alkoxy(1-4C)alkyl;
a phenyl(1-2C)alkyl group, the phenyl moiety of which is optionally substituted by (1-4C)alkoxy;
tetrahydrofuranyl;
a heterocyclyl-(1-2C)alkyl group wherein the heterocyclyl moiety is carbon-linked to the alkyl group and is either selected from the group consisting of a furan-2-yl, tetrahydrofuran-2-yl, tetrahydropyran-4-yl, pyridin-3-yl, pyrazin-2-yl, thiazol-2-yl, indo1-3-yl group, each of which is unsubstituted or substituted with one to three substituents selected from the group consisting of halo, (1-4C)alkyl, or halo(1-4C)alkyl, or the heterocyclyl moiety is selected from 1,3-dimethyl-1H-pyrazol-5-yl, 3,5-dimethyl-1H-pyrazol-4-yl, and 1-methyl-1H-imidazol-4-yl;
a group of sub-formula III:

$$R^9R^{10}N-[CR^eR^f]_c-X^2-[CR^gR^h]_d- \quad (III)$$

wherein:
$X^2$ is selected from a direct bond;
integer c is 1, or 2;
integer d is 0, or 1;
each $R^e$, $R^f$, $R^g$ and $R^h$ group present is independently selected from hydrogen or (1-2C)alkyl;
$R^9$ and $R^{10}$ are independently selected from hydrogen, (1-4C)alkyl, or $R^9$ and $R^{10}$ are linked so that, together with the nitrogen atom to which they are attached, they form a pyrrolidinyl, or piperidinyl ring;
or $R^7$ and $R^8$ are linked so that, together with the nitrogen atom to which they are attached, they form a 4 to 8-membered heterocyclic ring selected from the group consisting of azetidinyl, pyrrolidinyl, piperidinyl, piperazinyl, 3-azabicyclo[3.1.0]hexyl, hexahydropyrrolo[3,4-c]pyrrolyl, 7-azabicyclo[2.2.1]heptyl, and 2-azabicyclo[2.2.2]octyl, and wherein said heterocylylic ring is optionally substituted on carbon by one to three substituents selected from:

(a) halo, hydroxy, trifluoromethyl, (1-4C)alkyl, hydroxy (1-4C)alkyl, N-[(1-4C)alkyl]amino, N,N-di-[(1-4C) alkyl]amino,
a phenyl group which is optionally substituted with halo;
pyrrolidinyl, morpholinyl, piperazinyl optionally substituted with (1-4C)alkyl, or pyridinyl, (b) a group of the sub-formula VI:

$$Q^2-X^5-Y^2- \quad (VI)$$

wherein:
$Y^2$ is a direct bond;
$X^5$ is selected from —C(O)—; and
$Q^2$ is selected from pyrrolidinyl, or morpholinyl;
and, if said heterocyclic ring comprises a nitrogen atom then said nitrogen is optionally substituted by one or more substituent groups, which may be the same or different, selected from:
(a) (1-4C)alkyl, hydroxy(1-4C)alkyl, (2-4C)alkenyl, (1-4C)alkanoyl, (1-4C)alkoxy-(1-4C)alkyl;
a phenyl group which is optionally substituted with cyano;
a heterocyclyl group selected from pyrrolidinyl, morpholinyl, piperazinyl, pyrazinyl, pyrimidinyl, and pyridinyl, and wherein said ring is unsubstituted or substituted with cyano;
(b) a group of the formula VII:

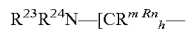 (VII)

wherein
integer h is 0, 1, or 2;
each $R^m$ and $R^n$ group present is hydrogen;
$R^{23}$ and $R^{24}$ are each independently selected from hydrogen or (1-4C)alkyl; or
(c) a group of the formula VIII:

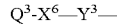 (VIII)

wherein $Y^3$ is a direct bond or —[$CR^{25}R^{26}$]$_z$— wherein z is 1 and $R^{25}$ and $R^{26}$ are both hydrogen;
$X^6$ is —C(O)—, if $Y^3$ is —[$CR^{23}R^{24}$]$_z$—, and if $Y^3$ is a direct bond, $X^6$ is selected from —SO$_2$— or —C(O)—; and
$Q^3$ is selected from (1-4C)alkyl, (3-6C)cycloalkyl, or pyrrolidinyl,
and wherein any non-aromatic heterocyclyl group within a $R^{1b}$ substituent group optionally bears 1 or 2 oxo substituents.

6. The compound according to claim 1 or a pharmaceutically acceptable salt thereof, wherein $R^{1b}$ is selected from hydrogen, cyano, amino, methyl, hydroxymethyl, 1-hydroxyethyl, (methylamino)methyl, (ethylamino)methyl, 1-(ethylamino)ethyl, (propylamino)methyl, (isopropylamino)methyl, (cyclopropylamino)methyl, (butylamino)methyl, (cyclobutylamino)methyl, (cyclopentylamino)methyl, (1-methylpropylamino)methyl, (2-methylpropylamino)methyl, (allylamino)methyl, (di-ethylamino) methyl, [(ethyl)(methyl)amino]methyl, [(isopropyl)(methyl)amino]methyl, [(propyl)(methyl)amino]methyl, [(butyl)(methyl)amino]methyl, [(cyclopropylmethyl)amino]methyl, [(cyclobutylmethyl)(methyl)amino]methyl, [(2-methoxyethyl)(methyl)amino]methyl, [(isopropyl)(2-methoxyethyl)amino]methyl, [(2-methoxyethyl)amino]methyl, [(ethyl)(2-methoxyethyl)amino]methyl, [(2-methoxy-1-methylethyl)amino]methyl, [(3-methoxypropyl)amino]methyl, [(3-isopropoxypropyl)amino]methyl, [(2-ethoxyethyl)amino]methyl, [(2-isopropoxyethyl)amino]methyl, [(3-ethoxypropyl)amino]methyl, [(2-propoxyethyl)amino]methyl, [(2-methoxy-2-methylpropyl)amino]methyl, [bis(2-methoxyethyl)amino]methyl, [(2-hydroxyethyl)(ethyl)amino]methyl, [(2-hydroxyethyl)(methyl)amino]methyl, {[2-(di-methylamino)ethyl]amino}methyl, {[2-(di-ethylamino)ethyl]amino}methyl, {[2-(di-methylamino)ethyl][methyl]amino}methyl, {[2-(di-ethylamino)ethyl][methyl]amino}methyl, {[2-(di-methylamino)-1-(methyl)ethyl]amino}methyl, azetidinylmethyl, pyrrolidinylmethyl, piperidinylmethyl, 1-piperidinylethyl, piperazinylmethyl, 7-azabicyclo[2.2.1]heptylmethyl, 2-azabicyclo[2.2.2]octylmethyl, {[2-(pyrrolidin-1-yl)ethyl]amino}methyl, {[2-(piperidin-1-yl)ethyl]amino}methyl, (3-fluoropyrrolidin-1-yl)methyl, (4-fluoropiperidin-1-yl)methyl, (3-hydroxypyrrolidin-1-yl)methyl, (3-hydroxypiperidin-1-yl)methyl, (4-hydroxypiperidin-1-yl)methyl, (4-trifluoromethylpiperidin-1-yl)methyl, [2,5-dimethylpyrrolidin-1-yl]methyl, (4-methylpiperidin-1-yl)methyl, (4-hydroxymethylpiperidin-1-yl)methyl, (3,3-dimethylpiperidin-l-yl)methyl, [6-(hydroxymethyl)-3-azabicyclo[3.1.0]hex-3-yl]methyl, (3-methylaminopyrrolidin-l-yl)methyl, [3-(dimethylamino)pyrrolidin-1-yl]methyl, [3-(diethylamino)pyrrolidin-1-yl]methyl, (3-phenylpyrrolidin-1-yl)methyl, (3-phenylpiperidin-1-yl)methyl, (4-phenylpiperidin-l-yl)methyl, [3-(4-fluorophenyl)piperidin-1-yl]methyl, (3-pyridin-2-ylpyrrolidin-l-yl)methyl, (4-morpholin-4-ylpiperidin-1-yl)methyl, [4-(2-oxopyrrolidin-1-yl)piperidin-1-yl]methyl, (4-pyrrolidin-1-ylpiperidin-1-yl)methyl, (4-pyridin-4-ylpiperidin-1-yl)methyl, [(4-methylpiperazin-1-yl)piperidin-1-yl]methyl, [4-(morpholin-4-ylcarbonyl)piperidin-1-yl]methyl, (4-methylpiperazin-1-yl)methyl, (4-ethylpiperazin-1-yl)methyl, [4-(2-hydroxyethyl)piperazin-1-yl]methyl, (4-isopropylpiperazin-1-yl)methyl, {4-[2-(dimethylamino)ethyl]piperazin-1-yl]methyl, (4-allylpiperazin-1-yl)methyl, (4-acetylpiperazin-1-yl)methyl, (5-butyrylhexahydropyrrolo[3,4-c]pyrrol-2(1H)-yl)methyl, [4-(2-methoxyethyl)piperazin-1-yl]methyl, [4-(methylsulfonyl)piperazin-1-yl]methyl, [4-(ethylsulfonyl)piperazin-1-yl]methyl, [4-(2-cyanophenyl)piperazin-1-yl]methyl, [4-(pyridin-2-yl)piperazin-1-yl]methyl, [4-(3-cyanopyridin-2-yl)piperazin-1-yl]methyl, [4-(3-cyanopyrazin-2-yl)piperazin-1-yl]methyl, (4-pyrimidin-2-ylpiperazin-1-yl)methyl, (4-pyrazin-2-ylpiperazin-1-yl)methyl, [4-(2-oxo-2-pyrrolidin-1-ylethyl)piperazin-1-yl]methyl, [4-(cyclopropylcarbonyl)piperazin-1-yl]methyl, {[(1,3-dimethyl-1H-pyrazol-5-yl)methyl]amino}methyl, {[2-(3,5-dimethyl-1H-pyrazol-4-yl)ethyl]amino}methyl, [methyl(tetrahydrofuran-2-ylmethyl)amino]methyl, [(5-methylpyrazin-2-yl)methyl]amino}methyl, [6-(trifluoromethyl)pyridin-3-yl]methyl}amino)methyl, [(4-methyl-1,3-thiazol-2-yl)methyl]amino}methyl, [2-(1-methyl-1H-imidazol-4-yl)ethyl]amino}methyl, [(tetrahydrofuran-2-ylmethyl)amino]methyl, [(5-methyl-2-furyl)methyl]amino}methyl, (tetrahydro-2H-pyran-4-ylmethyl)amino]methyl, (tetrahydro-2H-pyran-4-ylamino)methyl, {[2-(2-methyl-1H-indol-3-yl)ethyl]amino}methyl, (2-methoxybenzyl)amino]methyl, [(3-methoxybenzyl)amino]methyl, {[2-(isopropylamino)ethoxy]methyl, [2-(ethylamino)ethoxy]methyl, and [2-(methylamino)ethoxy]methyl.

7. The compound according to claim 1 or a pharmaceutically acceptable salt thereof, wherein $R^{1c}$ is selected from hydrogen, amino, (1-3C)alkyl, N-(1-3C)alkylamino, and N,N-di-[(1-3C)alkyl]amino.

8. The compound according to claim 1 or a pharmaceutically acceptable salt thereof, wherein said compound has the general formula IX:

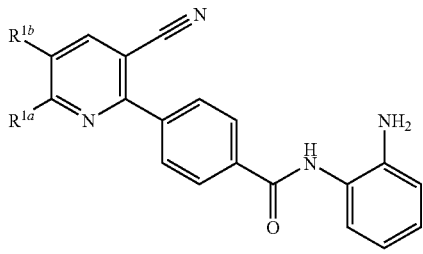

wherein $R^{1a}$ and $R^{1b}$ are as defined in claim 1.

9. The compound according to claim 8 or a pharmaceutically acceptable salt thereof, wherein $R^{1a}$ is hydrogen or (1-3C) alkyl.

10. The compound according to claim 1 or a pharmaceutically acceptable salt thereof, wherein said compound has the general formula X shown below:

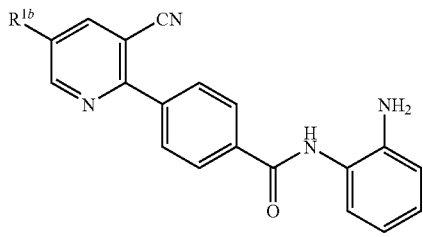

wherein $R^{1b}$ is as defined in claim 1.

11. The compound according to claim 2 or a pharmaceutically acceptable salt thereof, wherein $R^{1b}$ is hydrogen and $R^{1c}$ is hydrogen.

12. The compound according to claim 2 or a pharmaceutically acceptable salt thereof, wherein $R^{1b}$ is hydrogen and $R^{1a}$ is selected from hydrogen or (1-3C)alkyl.

13. The compound according to claim 1 which is any one of the following:

N-(2-aminophenyl)-4-(3-cyanopyridin-2-yl)benzamide;
N-(2-aminophenyl)-4-{3-cyano-6-[(2-hydroxyethyl)amino]-4-methylpyridin-2-yl}benzamide;
N-(2-aminophenyl)-4-[3-cyano-5-(piperidin-1-ylmethyl)pyridin-2-yl]benzamide;
N-(2-aminophenyl)-4-{3-cyano-5-[(4-methylpiperidin-1-yl)methyl]pyridin-2-yl}benzamide;
N-(2-aminophenyl)-4-{3-cyano-5-[(diethylamino)methyl]pyridin-2-yl}benzamide;
N-(2-aminophenyl)-4-[3-cyano-4-methyl-6-(4-methylpiperazin-1-yl)pyridin-2-yl]benzamide;
N-(2-aminophenyl)-4-[3-cyano-5-(pyrrolidin-1-ylmethyl)pyridin-2-yl]benzamide;
N-(2-aminophenyl)-4-{3-cyano-5-[(3-phenylpyrrolidin-1-yl)methyl]pyridin-2-yl}benzamide;
N-(2-aminophenyl)-4-{3-cyano-5-[(4-isopropylpiperazin-1-yl)methyl]pyridin-2-yl}benzamide;
N-(2-aminophenyl)-4-[3-cyano-5-(piperazin-1-ylmethyl)pyridin-2-yl]benzamide;
N-(2-aminophenyl)-4-{3-cyano-5-[(4-methylpiperazin-1-yl)methyl]pyridin-2-yl}benzamide;
N-(2-aminophenyl)-4-{3-cyano-5-[(4-ethylpiperazin-1-yl)methyl]pyridin-2-yl}benzamide;
N-(2-aminophenyl)-4-{3-cyano-5-[(3-pyridin-2-ylpyrrolidin-1-yl)methyl]pyridin-2-yl}benzamide;
N-(2-aminophenyl)-4-(3-cyano-5-{[(2R,5R)-2,5-dimethylpyrrolidin-1-yl]methyl}pyridin-2-yl1)benzamide;
N-(2-aminophenyl)-4-{3-cyano-5-[(4-hydroxypiperidin-1-yl)methyl]pyridin-2-yl}benzamide;
N-(2-aminophenyl)-4-(3-cyano-5-{[4-(trifluoromethyl)piperidin-1-yl]methyl}pyridin-2-yl1)benzamide;
N-(2-aminophenyl)-4-{3-cyano-5-[(4-morpholin-4-ylpiperidin-1-yl)methyl]pyridin-2-yl}benzamide;
N-(2-aminophenyl)-4-{3-cyano-5-[(3,3-dimethylpiperidin-1-yl)methyl]pyridin-2-yl}benzamide;
N-(2-aminophenyl)-4-[5-(azetidin-1-ylmethyl)-3-cyanopyridin-2-yl]benzamide;
N-(2-aminophenyl)-4-(3-cyano-5-{[4-(2-oxopyrrolidin-1-yl)piperidin-1-yl]methyl}pyridin-2-yl1)benzamide;
N-(2-aminophenyl)-4-{3-cyano-5-[(4-pyrrolidin-1-ylpiperidin-1-yl)methyl]pyridin-2-yl}benzamide;
N-(2-aminophenyl)-4-(3-cyano-5-{[(cyclobutylmethyl)(methyl)amino]methyl}pyridin-2-yl1)benzamide;
N-(2-aminophenyl)-4-(3-cyano-5-{[(2-methoxyethyl)(methyl)amino]methyl}pyridin-2-yl)benzamide;
N-(2-aminophenyl)-4-(3-cyano-5-{[(3S)-3-(dimethylamino)pyrrolidin-1-yl]methyl}pyridin-2-yl1)benzamide;
N-(2-aminophenyl)-4-(3-cyano-5-{ [(isopropyl)(2-methoxyethyl)amino]methyl} pyridin-2-yl)benzamide;
N-(2-aminophenyl)-4-{3-cyano-5-[(4-pyridin-4-yl piperidin-1-yl)methyl]pyridin-2-yl}benzamide;
N-(2-aminophenyl)-4-[5-(7-azabicyclo [2.2.1]hept-7-ylmethyl)-3-cyanopyridin-2-yl]benzamide;
N-(2-aminophenyl)-4-(3-cyano-5-{[(cyclopropylmethyl)amino]methyl}pyridin-2-yl)benzamide;
N-(2-aminophenyl)-4-[5-(2-azabicyclo [2.2.2]oct-2-ylmethyl)-3-cyanopyridin-2-yl]benzamide;
N-(2-aminophenyl)-4-[3-cyano-6-methyl-5-(1-piperidin-1-ylethyl)pyridin-2-yl]benzamide;
N-(2-aminophenyl)-4-(3-cyano-5-{[4-(4-methylpiperazin-1-yl)piperidin-1-yl]methyl}pyridin-2-yl)benzamide;
N-(2-aminophenyl)-4-(3-cyano-5-{[isopropyl(methyl)amino]methyl}pyridin-2-yl)benzamide;
N-(2-aminophenyl)-4-(3-cyano-5-{[ethyl(2-methoxyethyl)amino]methyl}pyridin-2-yl)benzamide;
N-(2-aminophenyl)-4-(3-cyano-5-{[methyl(propyl)amino]methyl}pyridin-2-yl)benzamide;
4-{5-[(4-allylpiperazin-1-yl)methyl]-3-cyanopyridin-2-yl}-N-(2-aminophenyl)benzamide;
N-(2-aminophenyl)-4-(3-cyano-5-{[4-(2-methoxyethyl)piperazin-1-yl]methyl}pyridin-2-yl)benzamide;
N-(2-aminophenyl)-4-[3-cyano-5-({[2-(dimethylamino)ethyl]amino}methyl)pyridin-2-yl]benzamide;
N-(2-aminophenyl)-4-[3-cyano-5-({[2-(diethylamino)ethyl]amino}methyl)pyridin-2-yl]benzamide;
N-(2-aminophenyl)-4-(3-cyano-5-{[(2-pyrrolidin-1-ylethyl)amino]methyl}pyridin-2-yl)benzamide;
N-(2-aminophenyl)-4-(3-cyano-5-{[(2-piperidin-1-ylethyl)amino]methyl}pyridin-2-yl)benzamide;
N-(2-aminophenyl)-4-(3-cyano-5-{[4-(3-cyanopyridin-2-yl)piperazin-1-yl]methyl}pyridin-2-yl)benzamide;
N-(2-aminophenyl)-4-[3-cyano-5-({4-[2-(dimethylamino)ethyl]piperazin-1-yl}methyl)pyridin-2-yl]benzamide;
N-(2-aminophenyl)-4-{3-cyano-5-[(4-pyridin-2-ylpiperazin-1-yl)methyl]pyridin-2-yl1}benzamide;
N-(2-aminophenyl)-4-(3-cyano-5-{[[2-(dimethylamino)ethyl](methyl)amino]methyl}pyridin-2-yl)benzamide;

N-(2-aminophenyl)-4-(3-cyano-5-{[[2-(diethylamino)ethyl](methyl)amino]methyl}pyridin-2-yl)benzamide;
N-(2-aminophenyl)-4-{3-cyano-5-[(propylamino)methyl]pyridin-2-yl}benzamide;
N-(2-aminophenyl)-4-{5-[(butylamino)methyl]-3-cyanopyridin-2-yl}benzamide;
N-(2-aminophenyl)-4-{5-[(sec-butylamino)methyl]-3-cyanopyridin-2-yl}benzamide;
N-(2-aminophenyl)-4-{3-cyano-5-[(cyclobutylamino)methyl]pyridin-2-yl}benzamide;
N-(2-aminophenyl)-4-{3-cyano-5-[(isopropylamino)methyl]pyridin-2-yl}benzamide;
N-(2-aminophenyl)-4-{3-cyano-5-[(isobutylamino)methyl]pyridin-2-yl}benzamide;
4-{5-[(allylamino)methyl]-3-cyanopyridin-2-yl}-N-(2-aminophenyl)benzamide;
N-(2-aminophenyl)-4-{3-cyano-5-[(cyclopentylamino)methyl]pyridin-2-yl}benzamide;
N-(2-aminophenyl)-4-{3-cyano-5-[(ethylamino)methyl]pyridin-2-yl}benzamide;
N-(2-aminophenyl)-4-{3-cyano-5-[(4-pyrazin-2-yl piperazin-1-yl)methyl]pyridin-2-yl1}benzamide;
N-(2-aminophenyl)-4-[3-cyano-5-({[2-(dimethylamino)-1-methylethyl]amino1methyl)pyridin-2-yl]benzamide;
N-(2-aminophenyl)-4-(3-cyano-5-{[3-(methylamino)pyrolidin-1-yl]methyl}pyridin-2-yl)benzamide;
N-(2-aminophenyl)-4-(3-cyano-5-{[4-(2-cyanophenyl)piperazin-1-yl]methyl}pyridin-2-yl)benzamide;
N-(2-aminophenyl)-4-(3-cyano-5-{[4-(3-cyanopyrazin-2-yl)piperazin-1-yl]methyl}pyridin-2-yl)benzamide;
N-(2-aminophenyl)-4-{3-cyano-5-[1-(ethylamino)ethyl]-6-methylpyridin-2-yl}benzamide;
N-(2-aminophenyl)-4-{3-cyano-5-[(methylamino)methyl]pyridin-2-yl}benzamide;
N-(2-aminophenyl)-4-(3-cyano-5-{[(3R)-3-hydroxypyrrolidin-1-yl]methyl}pyridin-2-yl)benzamide;
N-(2-aminophenyl)-4-(3-cyano-5-{[(3R)-3-fluoropyrrolidin-1-yl]methyl}pyridin-2-yl)benzamide;
N-(2-aminophenyl)-4-(3-cyano-5-{[(2-hydroxyethyl)(methyl)amino]methyl}pyridin-2-yl)benzamide;
N-(2-aminophenyl)-4-(3-cyano-5-{[4-(ethylsulfonyl) piperazin-1-yl]methyl}pyridin-2-yl)benzamide;
N-(2-aminophenyl)-4-{3-cyano-5-[(4-pyrimidin-2-ylpiperazin-1-yl)methyl]pyridin-2-yl1}benzamide;
445-amino-3-cyano-6-methylpyridin-2-yl)-N-(2-aminophenyl)benzamide;
N-(2-aminophenyl)-4-[3-cyano-5-({[(1R)-1-methylpropyl]amino1methyl)pyridin-2-yl]benzamide;
N-(2-aminophenyl)-4-[3-cyano-5-({[(1S)-1-methylpropyl]amino1methyl)pyridin-2-yl]benzamide;
N-(2-aminophenyl)-4-(3-cyano-5-{[4-(methylsulfonyl)piperazin-1-yl]methyl}pyridin-2-yl)benzamide;
N-(2-aminophenyl)-4-[3-cyano-5-({[2-(2-methyl-1H-indol-3-yl)ethyl]amino1methyl)pyridin-2-yl]benzamide;
N-(2-aminophenyl)-4-(3-cyano-5-{[2-(isopropylamino)ethoxy]methyl}pyridin-2-yl)benzamide;
N-(2-aminophenyl)-4-(3-cyano-5-{[2-(ethylamino)ethoxy]methyl}pyridin-2-yl)benzamide;
N-(2-aminophenyl)-4-(3-cyano-5-{[2-(methylamino)ethoxy]methyl}pyridin-2-yl)benzamide;
N-(2-aminophenyl)-4-(3-cyano-5-methylpyridin-2-yl)benzamide;
N-(2-aminophenyl)-4-[3-cyano-4-(dimethylamino)pyridin-2-yl]benzamide;
N-(2-aminophenyl)-4-[3-cyano-6-(ethylamino)-4-methylpyridin-2-yl]benzamide;
N-(2-aminophenyl)-4-(3-cyano-4,6-dimethylpyridin-2-yl)benzamide;
N-(2-aminophenyl)-4-(3-cyano-6-methylpyridin-2-yl)benzamide;
N-(2-aminophenyl)-4-(3-cyano-5-{[4-(2-oxo-2-pyrrolidin-1-ylethyl)piperazin-1-yl]methyl}pyridin-2-yl)benzamide;
N-(2-aminophenyl)-4-(3-cyano-5-{[4-(2-hydroxyethyl)piperazin-1-yl]methyl}pyridin-2-yl)benzamide;
N-(2-aminophenyl)-4-(3-cyano-5-{R1R,5S)-6-(hydroxymethyl)-3-azabicyclo[3.1.0]hex-3-yl]methyl}pyridin-2-yl)benzamide;
N-(2-aminophenyl)-4-{3-cyano-5-[(4-hydroxymethylpiperidin-1-yl)methyl]pyridin-2-yl1}benzamide;
4-{5-[(4-acetylpiperazin-1-yl)methyl]-3-cyanopyridin-2-yl}-N-(2-aminophenyl)benzamide;
N-(2-aminophenyl)-4-{3-cyano-5-[(3-hydroxypiperidin-1-yl)methyl]pyridin-2-yl}benzamide;
N-(2-aminophenyl)-4-{5-[(5-butyrylhexahydropyrrolo[3,4-c]pyrrol-2(1H)-yl)methyl]-3-cyanopyridin-2-yl}benzamide;
N-(2-aminophenyl)-4-(3-cyano-5-{[(2-hydroxyethyl)(ethyl)amino]methyl}pyridin-2-yl)benzamide;
N-(2-aminophenyl)-4-(3-cyano-5-{[(2-methoxyethyl)amino]methyl}pyridin-2-yl)benzamide;
N-(2-aminophenyl)-4-(3-cyano-5-{[ethyl(methyl)amino]methyl}pyridin-2-yl)benzamide;
N-(2-aminophenyl)-4-{3-cyano-5-[(3-phenylpiperidin-1-yl)methyl]pyridin-2-yl}benzamide;
N-(2-aminophenyl)-4-{3-cyano-5-[(4-phenylpiperidin-1-yl)methyl]pyridin-2-yl}benzamide;
N-(2-aminophenyl)-4-(3-cyano-5-{[3-(4-fluorophenyl)piperidin-1-yl]methyl}pyridin-2-yl)benzamide;
N-(2-aminophenyl)-4-(3-cyano-5-{[4-(morpholin-4-ylcarbonyl)piperidin-1-yl]methyl}pyridin-2-yl)benzamide;
N-(2-aminophenyl)-4-(3-cyano-5-{[3-(diethylamino)pyrrolidin-1-yl]methyl}pyridin-2-yl)benzamide;
N-(2-aminophenyl)-4-(5-{[butyl(methyl)amino]methyl}-3-cyanopyridin-2-yl)benzamide;
N-(2-aminophenyl)-4-(3-cyano-6-nitropyridin-2-yl)benzamide;
N-(2-aminophenyl)-4-[3-cyano-6-(4-fluorophenyl)pyridin-2-yl]benzamide;
4-(6-amino-3,5-dicyanopyridin-2-yl)-N-(2-aminophenyl)benzamide;
N-(2-aminophenyl)-4-(3-cyano-5-{[4-(cyclopropylcarbonyl)piperazin-1-yl]methyl}pyridin-2-yl)benzamide;
N-(2-aminophenyl)-4-{3-cyano-5-[(methylamino)methyl]pyridin-2-yl}benzamide;
N-(2-aminophenyl)-4-[3-cyano-5-({[(1,3-dimethyl-1H-pyrazol-5-yl)methyl]amino1methyl)pyridin-2-yl]benzamide;
N-(2-aminophenyl)-4-[3-cyano-5-({[2-(3,5-dimethyl-1H-pyrazol-4-yl)ethyl]amino 1methyl)pyridin-2-yl]benzamide;
N-(2-aminophenyl)-4-(3-cyano-5-{[(2-methoxy-1-methylethyl)amino]methyl}pyridin-2-yl)benzamide;
N-(2-aminophenyl)-4-(3-cyano-5-{[(3-methoxypropyl)amino]methyl}pyridin-2-yl)benzamide;
N-(2-aminophenyl)-4-(3-cyano-5-{[(2-methoxybenzyl)amino]methyl}pyridin-2-yl)benzamide;
N-(2-aminophenyl)-4-(3-cyano-5-{[(3-methoxybenzyl)amino]methyl}pyridin-2-yl)benzamide;
N-(2-aminophenyl)-4-(3-cyano-5-{[(3-isopropoxypropyl)amino]methyl}pyridin-2-yl)benzamide;

N-(2-aminophenyl)-4-{3-cyano-5-[({[6-(trifluoromethyl)pyridin-3-yl]methyl}amino)methyl]pyridin-2-yl}benzamide;

N-(2-aminophenyl)-4-[3-cyano-5-({[(4-methyl-1,3-thiazol-2-yl)methyl]amino1methyl)pyridin-2-yl]benzamide;

N-(2-aminophenyl)-4-[3-cyano-5-({[2-(1-methyl-1H-imidazol-4-yl)ethyl]amino}methyl)pyridin-2-yl]benzamide;

N-(2-aminophenyl)-4-(3-cyano-5-{[(tetrahydrofuran-2-ylmethyl)amino]methyl}pyridin-2-yl1)benzamide;

N-(2-aminophenyl)-4-(3-cyano-5-{[(2-ethoxyethyl)amino]methyl}pyridin-2-yl)benzamide;

N-(2-aminophenyl)-4-(3-cyano-5-{[(2-isopropoxyethyl)amino]methyl}pyridin-2-yl)benzamide;

N-(2-aminophenyl)-4-(3-cyano-5-{[(3-ethoxypropyl)amino]methyl}pyridin-2-yl)benzamide;

N-(2-aminophenyl)-4-(3-cyano-5-{[(2-propoxyethyl)amino]methyl}pyridin-2-yl)benzamide;

N-(2-aminophenyl)-4-[3-cyano-5-({[(5-methyl-2-furyl)methyl]amino}methyl)pyridin-2-yl]benzamide;

N-(2-aminophenyl)-4-(3-cyano-5-{[(tetrahydro-2H-pyran-4-ylmethyl)amino]methyl}pyridin-2-yl1)benzamide;

N-(2-aminophenyl)-4-{3-cyano-5-[(tetrahydro-2H-pyran-4-ylamino)methyl]pyridin-2-yl}benzamide;

N-(2-aminophenyl)-4-(3-cyano-5-{[(2-methoxy-2-methylpropyl)amino]methyl}pyridin-2-yl1)benzamide;

N-(2-aminophenyl)-4-(3-cyano-5-{[methyl(tetrahydrofuran-2-ylmethyl)amino]methyl}pyridin-2-yl1)benzamide;

N-(2-aminophenyl)-4-(5-{[bis(2-methoxyethyl)amino]methyl}-3-cyanopyridin-2-yl)benzamide;

or a pharmaceutically acceptable salt thereof.

14. A pharmaceutical composition comprising a compound or a pharmaceutically acceptable salt thereof according to any one of claims 1 to 13 in association with a pharmaceutically-acceptable diluent or carrier.

* * * * *